(12) United States Patent
Schweizer et al.

(10) Patent No.: US 7,951,905 B2
(45) Date of Patent: May 31, 2011

(54) SYNTHESIS OF CARBOHYDRATE-TEMPLATED AMINO ACIDS AND METHODS OF USING SAME

(75) Inventors: Frank Schweizer, Winnipeg (CA); Kaidong Zhang, Winnipeg (CA); Neil Owens, Winnipeg (CA); George Zhanel, Winnipeg (CA)

(73) Assignee: University of Manitoba, Winnipeg (CA)

( * ) Notice: Subject to any disclaimer, the term of this patent is extended or adjusted under 35 U.S.C. 154(b) by 253 days.

(21) Appl. No.: 11/857,367

(22) Filed: Sep. 18, 2007

(65) Prior Publication Data

US 2008/0275213 A1    Nov. 6, 2008

Related U.S. Application Data

(60) Provisional application No. 60/944,596, filed on Jun. 18, 2007, provisional application No. 60/867,214, filed on Nov. 27, 2006, provisional application No. 60/826,005, filed on Sep. 18, 2006.

(51) Int. Cl.
*C07K 2/00* (2006.01)
(52) U.S. Cl. ...................................................... 530/300
(58) Field of Classification Search ........................ None
See application file for complete search history.

(56) References Cited

OTHER PUBLICATIONS

Nie et al. "Synthesis of a Ring-Oxygenated Variant of the 2-Carboxy-6-hydroxyoctahydroindole Core of Aeruginosin 298-A from Glucose," J. Org. Chem., 2005, 70, 8687-8692.*
International Preliminary Report on Patentability, issued in Application No. PCT/IB2007/003752, date of issuance of report Mar. 24, 2009.
Colombo et al., "Stereoselective synthesis of C-glycosyl α-amino acids," *J. Org. Chem.*, 56:3897-3900, 1991.
Dondni and Marra, "Methods for anomeric carbon-linked and fused sugar amino acid synthesis: the gateway to artificial glycopeptides," *Chem. Rev.*, 100:4395-4421, 2000.
Cipolla et al., "Synthesis of a spiro d-proline analogue bearing d-fructose," *Letters in Drug Design and Discovery*, 2:239-244, 2005.
Knorr et al., "New coupling reagents in peptide chemistry," *Tetrahedron Lett.*, 30:1927-1930, 1989.
Owens et al., Tuning of the Prolyl *trans/cis*-amide rotamer population by use of *c*-glucosylproline hybrids, *J. Org. Chem.*, 72:4635-4643, 2007.
Schweizer and Inazu, "Chain extension of sugar delta-lactones with the enolate of tert-butyl bromoacetate and elaboration into functionalized C-ketosides, C-glycosides, and C-glucosyl glycines," *Organic Letters*, 3:4115-4118, 2001.
Strom et al., "The pharmacophore of short cationic antibacterial peptides," *J. Med. Chem.*, 46:1567-70, 2003.
Wong et al., "A Library Approach to the Discovery of Small Molecules That Recognize RNA: Use of a 1,3-Hydroxyamine Motif as Core," J. Am. Chem. Soc., 120:8319-8327, 1998.
Zhang and Schweizer, "Synthesis of spirocyclic glucose-proline hybrids (GlcProHs)," *Synlett*, 20:3111-3115, 2005.
Zhang et al., "Synthesis of Sugar-Lysine Chimera with Integrated gluco-Configured 1,3-Hydroxyamine Motif," *Synlett*, 2:239-242, 2007.
Dondoni et al., "Stereoselective addition of 2-furyllithium and 2-thiazolyllithium to sugar nitrones, synthesis of carbon-linked glycoglycines," *J. Org. Chem.*, 62:5484-5496, 1997.
Dondoni et al., "Three component staudinger-type stereoselective synthesis of c-glycosyl-b-lactams and their use as precursors for c-glycosyl isoserines and dipeptides. A polymer-assisted solution phase approach," *Adv. Synth. Catal.*, 346:1355-1360, 2004.
Jarvest et al., "Potent synthetic inhibitors of tyrosyl tRNA synthetase derived from c-pyranosyl analogues of SB-219383," *Bioorg. & Med. Chem. Lett.*, 11:715-718, 2001.
Simchen et al., "Synthese α-c-glucosylierter α-aminocarbonsaure-derivate," *Synthesis*, 6:525-527, 1990.
PCT International Search Report and Written Opinion, issued in International Application No. PCT/IB2007/003752, dated Jul. 21, 2008.

* cited by examiner

*Primary Examiner* — Christina Bradley
(74) *Attorney, Agent, or Firm* — Fulbright & Jaworski LLP

(57) ABSTRACT

The present invention generally relates to tetrahydropyranyl-derivatized amino acids, their syntheses and their incorporation into peptides and peptidomimetics. The tetrahydropyran moiety constrains the side chain of an amino acid, thereby providing a molecule that may act as a sugar- or amino acid-mimetic as well as a scaffold for combinatorial synthesis.

5 Claims, 7 Drawing Sheets amino acid, showing the alpha-carbon and the beta-carbon of the side chain tetrahydropyran amino acid, showing the alpha-carbon and the beta, gamma, delta and epsilon backbone groups of the side chain epsilon group tetrahydropyranyl-derivatized amino acids, further defined as tetrahydropyranyl-derivatized amino acid chimeras a tetrahydropyranyl-derivatized amino acid, further defined as a spirocyclic tetrahydropyranyl-derivatized proline a tetrahydropyranyl-derivatized amino acid, further defined as a fused bicyclic tetrahydropyranyl-derivatized proline

SYNTHESIS OF CARBOHYDRATE-TEMPLATED AMINO ACIDS AND METHODS OF USING SAME

This application claims priority to U.S. provisional patent application Ser. Nos. 60/826,005, filed on Sep. 18, 2006; 60/867,214, filed on Nov. 27, 2006; and 60/944,596, filed Jun. 18, 2007, each of which is incorporated herein by reference.

BACKGROUND OF THE INVENTION

1. Field of the Invention

The present invention generally relates to the fields of organic synthesis, carbohydrate chemistry and peptidomimetics.

2. Description of Related Art

In vivo, peptides are subjected to numerous cellular processes such as proteolytic cleavage, degradation, (de)glycosylation and the like, all of which impact the half-life of the peptide. These are important considerations when the peptide is acting as a pharmaceutical compound, as a longer half-life means longer effectiveness and fewer administrations.

For example, amino acids containing basic side chains (e.g., lysine, ornithine and arginine) occur frequently in antimicrobial peptides (AMPs). Although the mode of action of AMPs is not fully understood, most AMPs appear to manifest their biological action by enhancing the permeability of lipid membranes of pathogenic cells. This typically involves initial electrostatic interactions between the positively charged basic side chains to the negatively charged lipid membrane of pathogens, followed by adoption of an amphipathic α-helical or β-sheet structure (Hancock, 1998; Hancock and Scott, 2000). Although more potent antibiotics exist, the ability to kill target cells rapidly, unusually broad activity spectra against some of the more serious antibiotic resistant pathogens and relative difficulty with which mutants develop resistance in vitro make AMPs attractive targets for drug development (Hancock, 1998; Hancock and Scott, 2000). However, in vivo studies of many cationic peptide antibiotics have been disappointing most likely due to the fact that many AMPs exhibit poor bioavailability, susceptibility to proteolytic cleavage and low antimicrobial activity (Latham, 1999).

Other amino acids have been manipulated in an effort to minimize in vivo degradation processes, such as proline. Proline plays an important role in the formation of secondary structures in peptides and proteins because it induces a reversal in backbone conformation resulting in the formation of reverse turns and disruption of helices and sheets in proteins. Besides the occurrence of proline in β-turns, proline-rich sequences also exist as extended helices (Kakinoki et al, 2005) (polyproline-I and polyproline-II) and antimicrobial peptides (Reddy et al., 2004). In addition, proline occurs in many peptide-based lead compounds, such as AMPs and peptides with cancer-selective toxicity. Hydroxylated proline residues occur in nature in the form of collagenous peptides, virotoxin cyclic heptapeptides (Buku et al., 1980) and other peptides (Nakajima and Volcani, 1969; Taylor et al., 1994) and the role of hydroxylated proline residues on the conformational stability of the collagen triple helix has been extensively investigated (Vitagliano et al., 2001). Over the years a plethora of proline analogs such as $C^\beta$-, $C^\gamma$- and $C^\delta$-substituted prolines (Beausoleil and Lubell, 1996; Delaney and Madison, 1982; Samanen et al., 1990; Quancard et al., 2004), azaprolines (Che and Marshall, 2004), pseudoprolines (Tam and Miao, 1999), silaproline (Cavelier et al., 2002), proline-amino acid chimera (Sharm and Lubell, 1996) and fused bicyclic proline (Jeannotte and Lubell, 2004) analogues have been developed to study the structural and biological properties of proline surrogates in peptides (Cluzeau and Lubell, 2005; Blankley et al., 1987; Dumy et al., 1997; Li and Moeller, 1996). However, in vivo studies of many proline containing peptides exhibit poor bioavailability susceptibility to proteolytic cleavage.

SUMMARY OF THE INVENTION

The present invention is based on the discovery that amino acids may be conformationally constrained via incorporation into a tetrahydropyranyl scaffold, thus producing tetrahydropyran-derivatized amino acids. See FIG. 1 through FIG. 7 for non-limiting examples of tetrahydropyranyl-derivatized amino acids. As can be appreciated by these figures, the cyclic nature of the tetrahydropyran constrains an amino acid, such as the side chain of the amino acid, while the polyfunctional nature of the scaffold may allow for introduction of chemical diversity and artificial post-translational modifications such as hydroxylation and glycosylation. In this regard, the tetrahydropyran may be hydroxylated; for example, the tetrahydropyran may be based on a monosaccharide, such as glucose, mannose, or galactose. The tetrahydropyranyl-derivatized amino acids described herein may behave as glycomimetics or peptidomimetics, such as prolinemimetics. The tetrahydropyranyl-derivatized amino acids of the present invention may be incorporated into peptide or peptidomimetic syntheses. Such peptides may exhibit higher degrees of activity, stability and/or bioavailability than their parent peptides and peptidomimetics.

Accordingly, the present invention contemplates a tetrahydropyranyl-derivatized amino acid, wherein at least one backbone atom of the amino acid side chain is derivatized such that said atom is part of the tetrahydropyranyl ring. See, e.g., FIG. 1, FIG. 2 and FIG. 7.

In certain embodiments, sugar-amino acid chimeras of formula (Ia) are excluded from the tetrahydropyranyl-derivatized amino acids of the present invention:

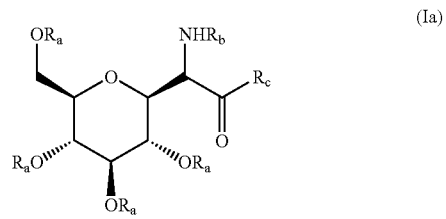
(Ia)

when $R_a$ is —H or a hydroxy protecting group, $R_b$ is —H or an amine protecting group, and $R_c$ is —OH, protected hydroxy, —OR, —Si(OR)$_3$, —NH$_2$, protected amine, or —NHR, wherein R is an alkyl group.

In certain embodiments, the present invention contemplates a tetrahydropyranyl-derivatized amino acid wherein at least one substituent of the tetrahydropyran ring comprises a terminal functional group of the amino acid side chain. The phrase "terminal functional group of an amino acid side chain" refers to a functional group that is found at the terminus of an amino acid side chain. Non-limiting examples of terminal functional groups of amino acid side chains include —CH$_3$ (alanine) or other hydrocarbon alkyl groups (isoleucine, valine, leucine), phenyl (phenylalanine), —SH (cysteine), —S—CH$_3$ (methionine), —C(O)NH$_2$ (asparagine, glutamine), —C$_6$H$_4$OH (tyrosine), —COOH (aspartic acid, glutamic acid), —NH$_2$ (lysine), —NHC(NH$_2$)—NH (arginine), indolyl (tryptophan), imidazolyl (histidine). As unnatural amino acids are also contemplated by the present invention, terminal functional groups of unnatural amino acids are also contemplated, such as —$NH_2$ (diaminobutyric acid and ornithine) and —SH (homocysteine). It is specifically contemplated that a terminal functional group of an amino acid may comprise additional atoms of an amino acid side chain as well. For example, with respect to phenylalanine, a substituent of the tetrahydropyranyl ring may be phenyl, or —$CH_2$-phenyl, or, with respect to homocysteine, —$CH_2SH$ and —SH are both contemplated as a substituent. Salts of terminal functional groups are also specifically contemplated (e.g., —$NHC(NH_2)=NH_2+$). Any of these terminal functional groups may also be protected with one or more protecting groups.

In certain embodiments regarding the tetrahydropyranyl ring position which is derivatized to constitute a backbone atom of an amino acid side chain, the backbone atom of the amino acid side chain is the beta-carbon. A non-limiting example of such a tetrahydropyranyl-derivatized amino acid in FIG. 1. In certain embodiments, more than one tetrahydropyranyl ring position constitutes more than one backbone atom of an amino acid side chain. For example, if an amino acid side chain comprises a gamma, delta, and/or epsilon group (or any additional group) in its backbone, more than one tetrahydropyranyl ring position may constitute any one or more of these groups. See FIG. 1. For example, at least one backbone atom of the side chain that is part of the tetrahydropyranyl ring may constitute the backbone atom any of the following: the beta-position of the side chain; the beta- and gamma-positions of the side chain; the beta-, gamma- and delta-positions of the side chain; the beta-, gamma-, delta- and epsilon-positions of the side chain; or the gamma- and delta-positions of the side chain. In certain embodiments, the tetrahydropyranyl-derivatized amino acid comprises a gamma, delta, and/or epsilon backbone group in its side chain, wherein one or more tetrahydropyranyl ring position(s) constitutes one or more backbone atom position(s) of said gamma, delta, or epsilon group, as consecutively numbered from the beta-carbon position.

In any embodiment regarding tetrahydropyranyl rings discussed herein, the tetrahydropyran may be further defined as a monosaccharide (sugar). Non-limiting examples of monosaccharides include glucose, mannose, and galactose. The hydroxy groups of these sugars may be unprotected or protected by a hydroxy protecting group.

In certain embodiments, a tetrahydropyranyl-derivatized amino acid is further defined as a compound of formula (I):

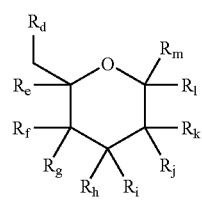

(I)

wherein: $R_d$-$R_m$ are each independently —H, alkyl, alkylthio, aryl, aralkyl, —$C(O)NH_2$, —$CO_2H$, —SH, —$N_3$, —$OR_{11}$, —$N(R_{13})C(NH(R_{13}))=NH+$, —$NHR_{12}$, or —$C_\alpha(NHR_{13})C(O)R_{14}$, wherein: $R_{11}$ is —H, alkyl, aryl, or a hydroxy protecting group; $R_{12}$ is —H, alkyl, aryl, or an amine or guanidine protecting group; $R_{13}$ is —H or an amine protecting group; $R_{14}$ is —$OR_{15}$, —$NHR_{16}$, or —N(H)—$CR_{17}R_{18}$; wherein: $R_{15}$ is —H, alkyl, aryl, or a carboxyl protecting group; $R_{16}$ is —H, alkyl, aryl, or an amine protecting group; $R_{17}$ is —$(X_5)_n(X_6)_p(X_7)_q(X_8)_rCO_2R_{19}$, wherein: $X_5$-$X_8$ are each independently Trp, Phe, Tyr, Lys, Arg, Leu, Val, Ile, or SLysC; n, p, q and r are each independently 0-4, such that n+p+q+r=2-4; and $R_{19}$ is —H, alkyl, aryl, or a carboxyl protecting group; and $R_{18}$ is —$C(O)OR_{20}$, or —$C(O)NHR_{21}$, wherein: $R_{20}$ is —H, alkyl, aryl, or a carboxyl protecting group; and $R_{21}$ is —H, alkyl, aryl, or an amine protecting group; or $R_l$ and $R_m$ taken together form the following substituent:

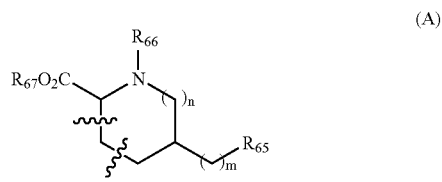

(A)

wherein: $R_{65}$ is —H, —$OR_{88}$, —$N_3$, —$NHR_{89}$, —$NHC(NHR_{89})=NH_2+$, —$N(R_{89})C(NH(R_{90}))NH_2+$, —$SR_{91}$, or —$NR_{89}R_{90}$, wherein: $R_{88}$ is —H, alkyl, aryl, or a hydroxy protecting group; $R_{89}$ and $R_{90}$ are each independently —H, an amine protecting group, wherein $R_{89} \neq R_{90}$; and $R_{91}$ is alkyl, aryl, cysteine, or a thiol protecting group; $R_{66}$ is —H, alkyl, aryl, or an amine protecting group; $R_{67}$ is —H, alkyl, aryl, or a carboxyl protecting group; and n and m are each independently 0 or 1 such that when n is 1, m is 0 and when n is 0, m is 1; or $R_k$ and $R_j$ together form the following substituent:

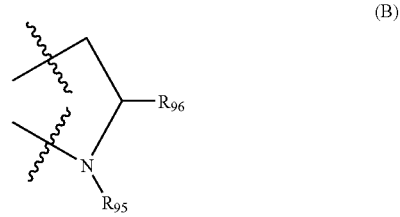

(B)

wherein: $R_{95}$ is —H, alkyl, aryl, an amine protecting group, or —$COR_{98}$, wherein $R_{98}$ is alkyl, aryl, —$C_\alpha H(Y)NHR_{99}$, or —$CH(CH_3)NHR_{99}$, wherein: $C_\alpha$ is the alpha-carbon of the amino acid; $R_{99}$ is —H or an amine protecting group; and Y is the side chain of the amino acid; or $R_{95}$ together with $R_{96}$ forms a 2-oxazolidinonyl group; $R_{96}$ is —$CH_2$-halo, —$CH_2OH$ or —$C(O)R_{99}$, wherein $R_{99}$ is —$NHCH_3$ or —$OR_{100}$, wherein $R_{100}$ is —H, alkyl, aryl, or a carboxyl protecting group; or $R_{96}$ together with $R_{95}$ forms a 2-oxazolidinonyl group; provided that when $R_l$ and $R_m$ do not form the substituent of formula (A) and $R_k$ and $R_j$ do not form the substituent of formula (B), then: at least one of $R_1$-$R_{10}$ is —$C_\alpha(NHR_{13})C(O)R_{14}$, wherein: the tetrahydropyranyl ring carbon to which $C_\alpha$ is bound constitutes the beta-carbon of the amino acid side chain; and if the tetrahydropyranyl-derivatized amino acid further comprises a gamma, delta, and/or epsilon group in its side chain, then one or more tetrahydropyranyl ring position(s) constitutes one or more backbone atom position(s) of said gamma, delta, or epsilon group, as consecutively numbered along the tetrahydropyran ring starting from the beta-carbon position; and at least one of $R_1$-$R_{10}$ is alkyl, alkylthio, aryl, aralkyl, —$C(O)NH_2$, —$CO_2H$, —SH, —$OR_{11}$, —$NHC(NHR_{13})=NH_2+$, or —$NHR_{12}$.

Also contemplated by the present invention are methods of synthesis, such as a method of synthesizing a tetrahydropyranyl-derivatized amino acid, comprising derivatizing the carbon adjacent to the oxygen in the tetrahydropyran ring such that said carbon becomes the beta-carbon of an amino acid. In certain embodiments regarding any method of synthesis of the present invention, sugar-amino acid chimeras of formula (Ia) are excluded:

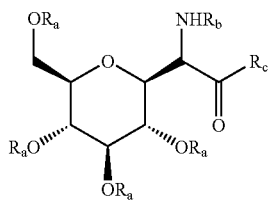

(Ia)

when $R_a$ is —H or a hydroxy protecting group, $R_b$ is —H or an amine protecting group, and $R_c$ is —OH, protected hydroxy, —OR, —Si(OR)$_3$, —NH$_2$, protected amine, or —NHR, wherein R is an alkyl group.

Other methods of synthesis contemplated by the present invention comprise a method of peptide or peptidomimetic synthesis, comprising incorporating a tetrahydropyranyl-derivatized amino acid into the peptide or peptidomimetic. In certain embodiments regarding peptide or peptidomimetic synthesis, sugar-amino acid chimeras of formula (Ia) are excluded:

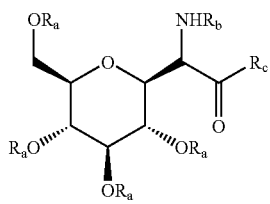

(Ia)

when $R_a$ is —H or a hydroxy protecting group, $R_b$ is —H or an amine protecting group, and $R_c$ is —OH, protected hydroxy, —OR, —Si(OR)$_3$, —NH$_2$, protected amine, or —NHR, wherein R is an alkyl group. Methods of peptide and peptidomimetic synthesis are well-known to those of skill in the art: incorporation of a tetrahydropyranyl-derivatized amino acid may be performed in such syntheses using comparable methods. For example, a tetrahydropyranyl-derivatized amino acid may be used as a substitute for an amino acid in peptide or peptidomimetic synthesis, or may be inserted as an additional residue in a peptide or peptidomimetic. Additional examples of this incorporation are described herein. Peptides and/or peptidomimetics comprising at least one tetrahydropyranyl-derivatized amino acid are also encompassed by the present invention.

In certain embodiments, a tetrahydropyranyl-derivatized amino acid is further defined as a sugar-amino acid chimera. Sugar-amino acid chimeras of the present invention refer to tetrahydropyranyl-derivatized amino acids comprising at least the following features: the tetrahydropyran is further defined as a sugar; a substituent of the tetrahydropyran ring is the —C$_\alpha$(NH$_2$)COOH group of the amino acid (including both D and L forms of this group, salt forms of this group, and amine- and/or carboxyl-protected forms of this group); the beta-carbon of the amino acid constitutes a position of the tetrahydropyranyl ring; and a substituent of the tetrahydropyranyl ring comprises a terminal functional group of the amino acid side chain. In certain embodiments, a sugar-amino acid chimera is a compound of formula (II):

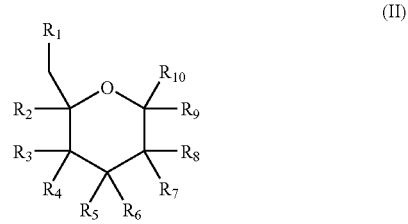

(II)

wherein: $R_1$-$R_{10}$ are each independently —H, alkyl, alkylthio, aryl, aralkyl, —C(O)NH$_2$, —CO$_2$H, —SH, —N$_3$, —OR$_{11}$, —NHC(NHR$_{13}$)=NH$_2$+, —NHR$_{12}$, or —C$_\alpha$(NHR$_{13}$)C(O)R$_{14}$, wherein: $R_{11}$ is —H, alkyl, aryl, or a hydroxy protecting group; $R_{12}$ is —H, alkyl, aryl, or an amine or guanidine protecting group; $R_{13}$ is —H or an amine protecting group; $R_{14}$ is —OR$_{15}$, —NHR$_{16}$, or —N(H)—CR$_{17}$R$_{18}$, wherein: $R_{15}$ is —H, alkyl, aryl, or a carboxyl protecting group; $R_{16}$ is —H, alkyl, aryl, or an amine protecting group; $R_{17}$ is —(X$_5$)$_n$(X$_6$)$_p$(X$_7$)$_q$(X$_8$)$_r$CO$_2$R$_{19}$, wherein: $X_5$-$X_8$ are each independently an amino acid, such as Trp, Phe, Tyr, Lys, Arg, Leu, Val, Ile, or SLysC (wherein SLysC refers to a sugar-lysine chimera); n, p, q and r are each independently 0-4 (that is 0, 1, 2, 3, or 4; numbers 5 and higher are also specifically contemplated); and $R_{19}$ is —H, alkyl, aryl, or a carboxyl protecting group; and $R_{18}$ is —C(O)OR$_{20}$, or —C(O)NHR$_{21}$, wherein: $R_{20}$ is —H, alkyl, aryl, or a carboxyl protecting group; and $R_{21}$ is —H, alkyl, aryl, or an amine protecting group; provided that: at least one of $R_1$-$R_{10}$ is —C$_\alpha$(NHR$_{13}$)C(O)R$_{14}$, wherein: the tetrahydropyranyl ring carbon to which C$_\alpha$ is bound constitutes the beta-carbon of the amino acid side chain; and if the tetrahydropyranyl-derivatized amino acid further comprises a gamma, delta, and/or epsilon group (or any additional group) in its side chain, then one or more tetrahydropyranyl ring position(s) constitutes one or more backbone atom position(s) of said gamma, delta, or epsilon group (or any additional group), as consecutively numbered along the tetrahydropyran ring starting from the beta-carbon position; and at least one of $R_1$-$R_{10}$ is alkyl, alkylthio, aryl, aralkyl, —C(O)NH$_2$, —CO$_2$H, —SH, —OR$_{11}$, —NHC(NHR$_{13}$)=NH$_2$+, or —NHR$_{12}$. In certain embodiments, n+p+q+r=2-4. By —(X$_5$)$_n$(X$_6$)$_p$(X$_7$)$_q$(X$_8$)$_r$CO$_2$R$_{19}$, it is meant that the amino acids are joined together by peptide bonds such that the terminal amino acid comprises a carboxyl group (that is, —COO$^-$ or CO$_2$R$_{19}$). Moreover, any adjacent pair of $R_1$-$R_{10}$ (e.g., $R_9$ and $R_{10}$) may together form a substituent comprising a proline residue.

In particular, a sugar-amino acid chimera of the present invention may be further defined as a compound of formula (III):

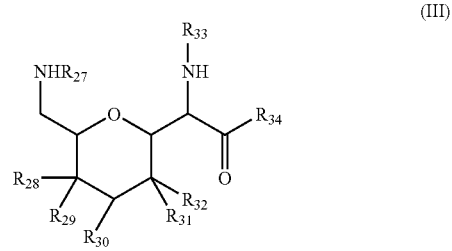

(III)

wherein: $R_{27}$ is —H, alkyl, aryl, or an amine protecting group (such as Boc); $R_{28}$-$R_{32}$ are each independently —H, —$NH_2$, —$NHC(NH_2)=NH_2+$, or —$OR_{22}$, wherein $R_{22}$ is —H, alkyl, aryl, or a hydroxy protecting group (such as a benzyl group or a carbamate); $R_{33}$ is —H, alkyl, aryl, an amine protecting group (such as Fmoc), or —$R_{23}R_{24}$, wherein: $R_{23}$ is —$C(O)(X_1)_h(X_2)_j(X_3)_k(X_4)_m NH_2$, wherein $X_1$-$X_4$ are each independently an amino acid, such as Trp, Phe, Tyr, Lys, Arg, Leu, Val, Ile, or SLysC (wherein SLysC is a sugar-lysine chimera) and h, j, k and n are each independently 0-4 (or 5 or higher); and $R_{24}$ is —$C(O)OR_t$ or —$C(O)NHR_z$, wherein: $R_t$ is —H, alkyl, aryl, or a carboxyl protecting group; and $R_z$ is —H, alkyl, aryl, or an amine protecting group; $R_{34}$ is —$OR_{25}$, —$NHR_{26}$, or —$N(H)$—$CR_{41}R_{42}$, wherein: $R_{25}$ is —H, alkyl, aryl, or a hydroxy protecting group; $R_{26}$ is —H, alkyl, aryl, or an amine protecting group; $R_{41}$ is —$NH(X_5)_n(X_6)_p(X_7)_q(X_8)_r CO_2H$, wherein $X_5$-$X_8$ are each independently an amino acid, such as Trp, Phe, Tyr, Lys, Arg, Leu, Val, Ile, or SLysC and n, p, q and r are each independently 0-4 (or 5 or higher); and $R_{42}$ is —$C(O)OR_{43}$ or —$C(O)NHR_{44}$, wherein: $R_{43}$ is —H, alkyl, aryl, or a carboxyl protecting group; and $R_{44}$ is —H, alkyl, aryl, or an amine protecting group. In certain embodiments, h+j+k+m=2-4. In certain embodiments, n+p+q+r=2-4. By —$C(O)(X_1)_h(X_2)_j(X_3)_k(X_4)_m NH_2$, it is meant that the carboxyl end of the amino acid is joined to the rest of the molecule and the amino acids are joined together by peptide bonds such that the terminal amino acid terminates in an amino group (which may be in a salt or protected form). By —$NH(X_5)_n(X_6)_p(X_7)_q(X_8)_r CO_2H$, it is meant that the amino end of an amino acid is bound to the rest of the molecule and the terminal amino acid terminates in a carboxyl group (which may be in a protected, unprotected, or protected form, or as a primary amide (—$C(O)NH_2$)).

In certain embodiments, a sugar-amino acid chimera of the present invention is further defined as a compound of formula (IV):

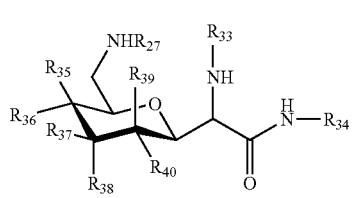

(IV)

wherein: $R_{27}$, $R_{33}$ and $R_{34}$ are defined as above; one of $R_{35}$ and $R_{36}$ is —H and the other is —OH; one of $R_{37}$ and $R_{38}$ is —H and the other is —OH; and one of $R_{39}$ and $R_{40}$ is —H and the other is —OH. Any of these —OH's may be protected by a hydroxy group as well.

In certain embodiments, a sugar-amino acid of the present invention is further defined as one or more of the following compounds:

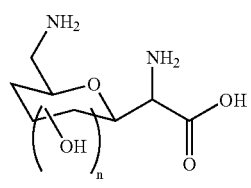

sugar-lysine chimera

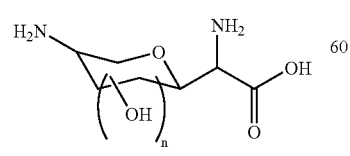

sugar-lysine chimera

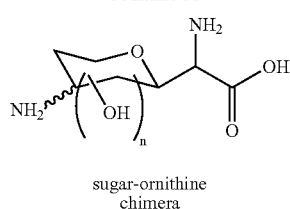

sugar-ornithine chimera

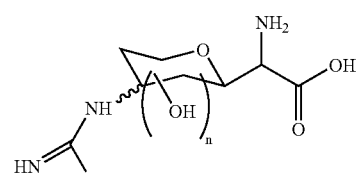

sugar-arginine chimera

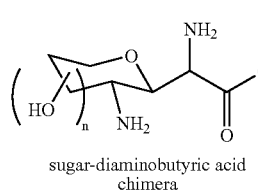

sugar-diaminobutyric acid chimera

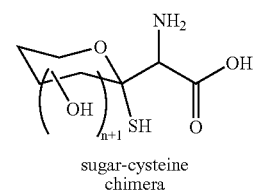

sugar-cysteine chimera

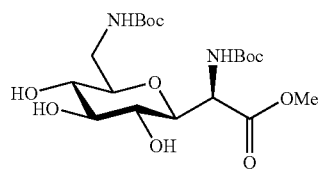

-continued

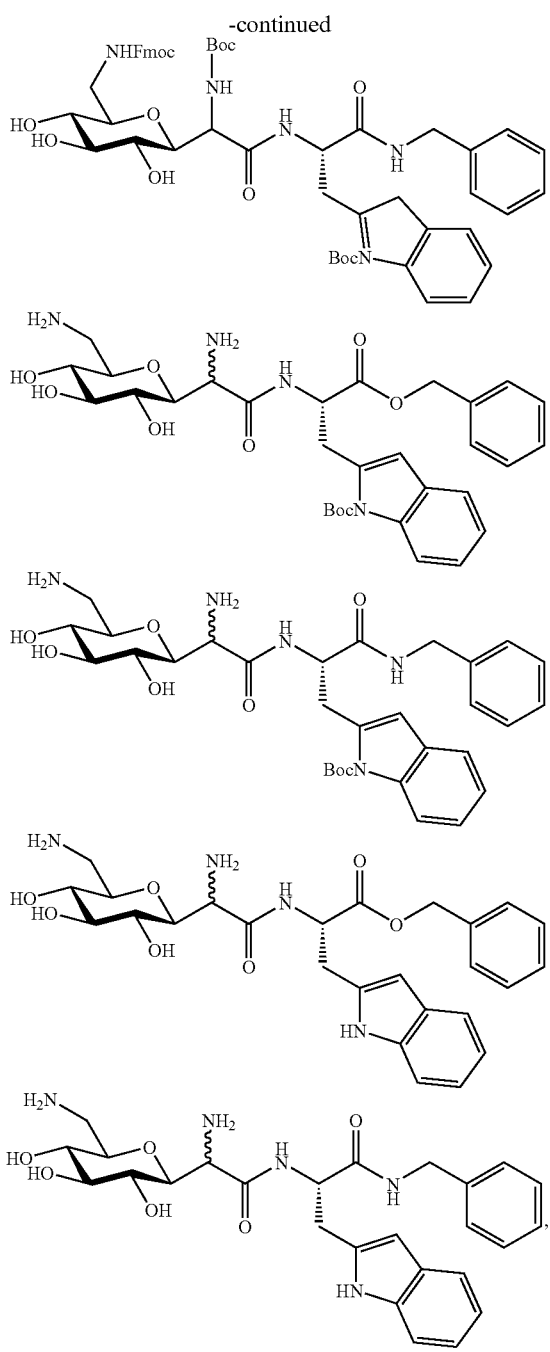

wherein n is 3.

In certain embodiments, methods of preparing a tetrahydropyranyl-derivatized amino acid, wherein the tetrahydropyranyl-derivatized amino acid is further defined as a sugar-lysine chimera, are contemplated, comprising:

a) reacting a fully hydroxy protected delta lactone with an enolate of an alpha halo ester, thereby generating an exocyclic epoxide;
b) opening the reductive ring of the exocyclic epoxide with a nucleophile, thereby providing a protected C-glycosyl alpha hydroxy ester wherein the C1-carbon of the C-glycosyl group is hydroxylated;
c) converting the C-glycosyl alpha hydroxy methyl ester into a benzylester;
d) installing a first amino function by activating the hydroxy function at the C1-carbon of the C-glycosyl group as a sulfonate ester followed by displacement by a nitrogen-containing nucleophile;
e) installing a second amino function by deblocking the sugar protecting groups and then activating the hydroxymethyl group as sulfonate ester followed by nucleophilic displacement by an azide;
f) converting the molecule to an acid form by ester hydrolysis;
g) reducing the azide, thereby producing a sugar-lysine chimera; and
h) optionally separating any set of diastereomers formed during any step of the method.

In certain embodiments regarding a method of synthesizing a sugar-lysine chimera, one or both of the following compounds may be formed as an intermediate: a compound of formula (VIII):

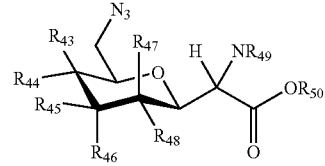

(VIII)

wherein: one of $R_{43}$ and $R_{44}$ is —H and the other is —OH; one of $R_{45}$ and $R_{46}$ is —H and the other is —OH; one of $R_{47}$ and $R_{48}$ is —H and the other is —OH; $R_{49}$ is an amine protecting group; and $R_{50}$ is a carboxyl protecting group; and/or a compound of formula (IX):

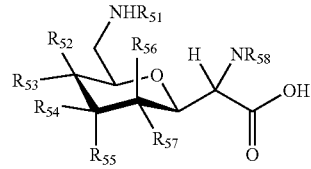

(IX)

wherein: $R_{51}$ and $R_{58}$ are each an amine protecting group; and one of $R_{52}$ and $R_{53}$ is —H and the other is —OH; one of $R_{54}$ and $R_{55}$ is —H and the other is —OH; one of $R_{56}$ and $R_{57}$ is —H and the other is —OH.

In certain embodiments regarding a method of synthesizing a sugar-lysine chimera one or more of the following compounds may be formed as an intermediate:

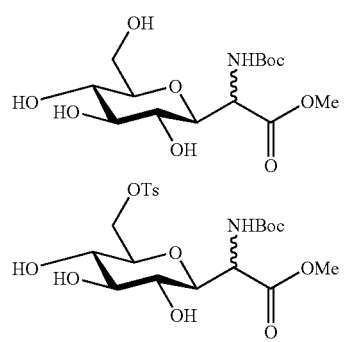

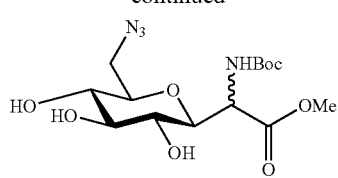

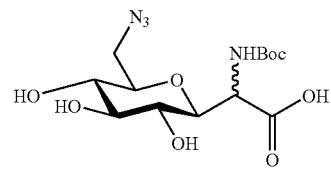

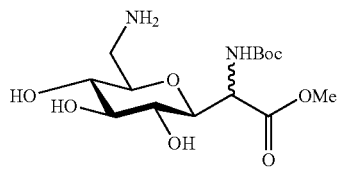

Also contemplated by methods of the present invention are methods of peptide or peptidomimetic synthesis, wherein a sugar-amino acid chimera, such as a sugar-lysine chimera, is incorporated into the peptide or peptidomimetic. Typically in these syntheses, functional groups (such as amine groups) of sugar-lysine chimeras will be orthogonally protected by protecting groups that will facilitate peptide synthesis, as known to those of skill in the art. In certain of these methods, the sugar-amino acid chimeras of formula (Ia) are excluded:

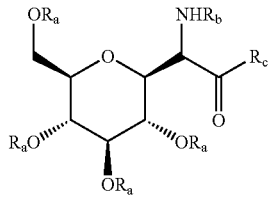

(Ia)

when $R_a$ is —H or a hydroxy protecting group, $R_b$ is —H or an amine protecting group, and $R_c$ is —OH, —OR, —Si(OR)$_3$, protected hydroxy, —NH$_2$, protected amine, or —NHR, wherein R is an alkyl group. The peptide or peptidomimetic may, in certain embodiments, be an antimicrobial peptide, wherein the incorporation of the sugar-amino acid chimera comprises replacing one or more amino acids within the wild type amino acid sequence of said antimicrobial peptide with the sugar-amino acid chimera. The sugar-amino acid chimera may be a sugar-lysine chimera, or any other sugar-amino acid chimera wherein the amino acid side chain is positively charged. Antimicrobial peptides are well-known to those of skill in the art. Non-limiting examples of antimicrobial peptides include: KSL, indolicidin, gramicidin S, buforin, pyrrhocoricin and drosocin.

In certain embodiments, a tetrahydropyranyl-derivatized amino acid of the present invention may be further defined as a spirocyclic sugar-proline of formula (V):

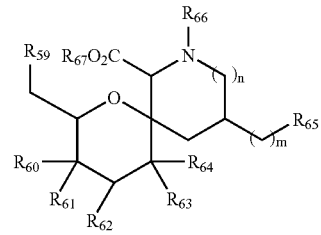

(V)

wherein: $R_{59}$-$R_{63}$ is —H, alkyl, aryl, —OR$_{68}$, —N$_3$, or —NHR$_{45}$, wherein: $R_{68}$ is —H, alkyl, aryl, or a hydroxy protecting group (such as a siloxy group, a carbamate, a methoxymethyl group, or a benzyl group); $R_{45}$ is —H, alkyl, aryl, or an amine protecting group (such as benzyl, Fmoc, Boc, or Cbz); $R_{64}$ is —H, alkyl, aryl, —OR$_{85}$, —NHC(NHR$_{86}$)=NH$_2$+, —N(R$_{86}$)C(NH(R$_{87}$))=NH+, —N$_3$, —NH$_2$, or —NHR$_{86}$, wherein: $R_{85}$ is alkyl, aryl, or a hydroxy protecting group; and $R_{86}$ and $R_{87}$ are each independently —H or an amine protecting group; $R_{65}$ is —H, —OR$_{88}$, —N$_3$, —NHR$_{89}$, —NHC(NHR$_{89}$)=NH$_2$+, —N(R$_{89}$)C(NH(R$_{90}$))NH$_2$+, —SR$_{91}$, or —NR$_{89}$R$_{90}$, wherein: $R_{88}$ is —H, alkyl, aryl, or a hydroxy protecting group; $R_{89}$ and $R_{90}$ are each independently —H, an amine protecting group; and $R_{91}$ is alkyl, aryl, cysteine, or a thiol protecting group; $R_{66}$ is —H, alkyl, aryl, or an amine protecting group (such as Boc, Fmoc, or Cbz); $R_{67}$ is —H, alkyl, aryl, or a carboxyl protecting group; and n and m are each independently 0 or 1. In certain embodiments, when n is 1, m is 0; and/or when n is 0, m is 1. In certain embodiments, $R_{86} \neq R_{87}$. In certain embodiments, $R_{89} \neq R_{90}$. In certain embodiments, $R_{86}$ and $R_{89}$ are each independently Mtr, Mts, Tos, Pbf, Pmc, or Mbs. In certain embodiments, $R_{87}$ and $R_{90}$ are each independently Boc or Cbz. In certain embodiments, any one or more of $R_{59}$-$R_{64}$ is a terminal functional group of an amino acid side chain. The sugar may be any tetrahydropyranyl-based sugar known to those of skill in the art, such as glucosyl, mannosyl, or galactosyl.

In certain embodiments, a spirocyclic sugar-proline is further defined as any one or more of the following compounds:

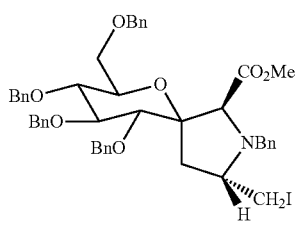

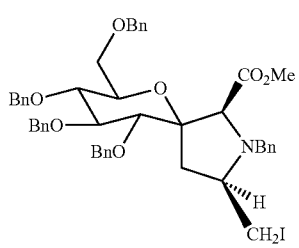

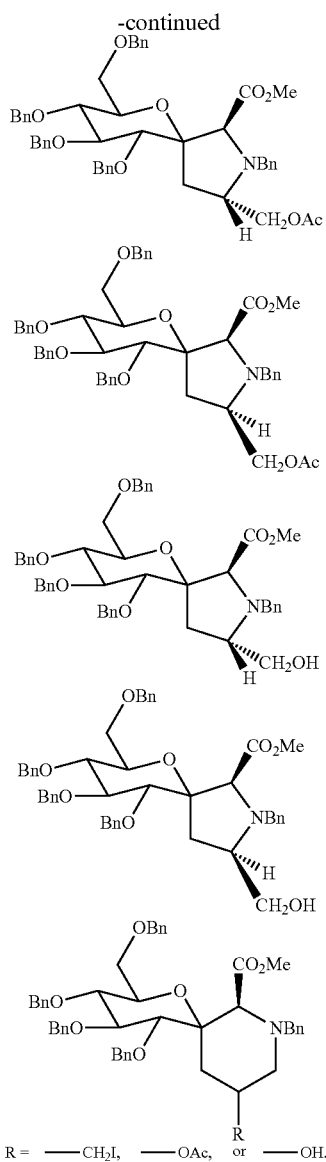

R = —CH₂I,   —OAc,   or   —OH.

Moreover, spirocyclic tetrahydropyranyl-derivatized prolines of the present invention may be constructed such that the tetrahydropyranyl moiety comprises a substituent that mimics a a terminal functional group of an amino acid side chain. For example, when the tetrahydropyran is further defined as a sugar, a spirocyclic sugar-proline-amino acid may be generated. An example of a tri-sectional compound is shown in FIG. 7, wherein the tetrahydropyranyl group features a terminal functional group of the side chain of ornithine. The tetrahydropyran may therefore comprise any terminal functional group of any amino acid, as described above in the context of the sugar-amino acid chimeras. In certain embodiments, a hydroxy or protected hydroxy group of an amino acid side chain is specifically excluded in this context. Such polyfunctional compounds may also be incorporated into peptide and peptidomimetic syntheses.

Certain methods of the present invention contemplate a method of synthesizing a tetrahydropyranyl-derivatized amino acid, wherein the tetrahydropyranyl-derivatized amino acid is further defined as a spirocyclic sugar-proline. In certain embodiments, a method of synthesizing a spirocyclic sugar-proline comprises:

a) reacting a fully hydroxy protected sugar-derived delta lactone (such as a fully benzylether protected delta lactone) with an enolate of an alpha halo ester thereby producing an exocyclic epoxide having a reductive ring;

b) opening the reductive ring with an allylic C-nucleophile thereby producing a C-ketoside bearing a glycosyl alpha hydroxy ester;

c) oxidizing the alpha hydroxy ester to an alpha keto ester;

d) reductively aminating the keto;

e) forming a pyrrolidine ring by iodine or bromine induced cyclization, thereby producing a spirocyclic sugar-proline comprising an iodomethylene or bromomethylene substituent;

f) optionally reacting the iodomethylene or bromoethylene with a nucleophile; and g) optionally deblocking one or more of the hydroxy sugar protecting groups.

The nucleophile of step b) may be any nucleophile as known to those of skill in the art, such as an acetate anion, a carboxylate anion, a hydroxide anion, a sulfur nucleophile, an amine, azide, or a peptidyl amine. Reductive amination is well-known to those of skill in the art. In certain embodiments, reductive amination is carried out using an amine selected from the group consisting of ammonia, an aryl amine (e.g., benzylamine), an allylamine, an aminoester, or a peptidyl amine. The introduced amine may be further protected by an amine protecting group, such as Boc, Fmoc, Cbz, or benzyl. A deblocked hydroxy group on the sugar may then be further reacted as desired.

In certain methods of synthesizing a spirocyclic sugar-proline, one or more of the following compounds may be formed as an intermediate:

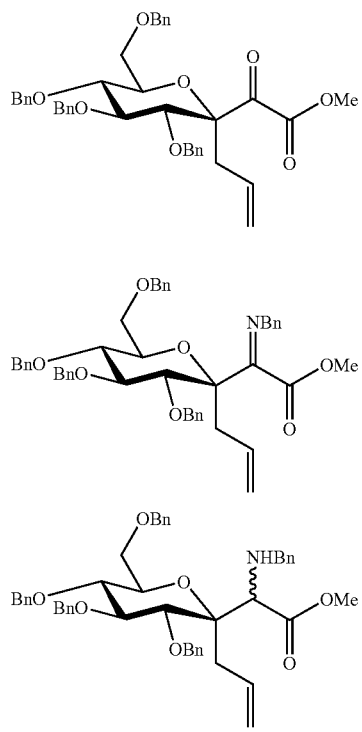

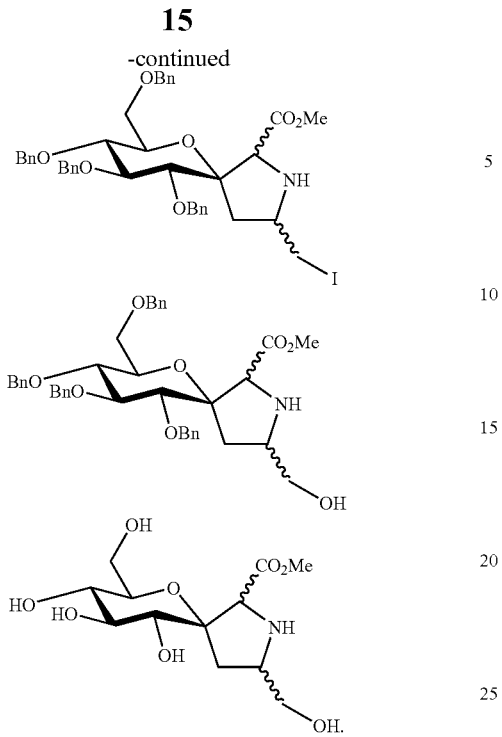

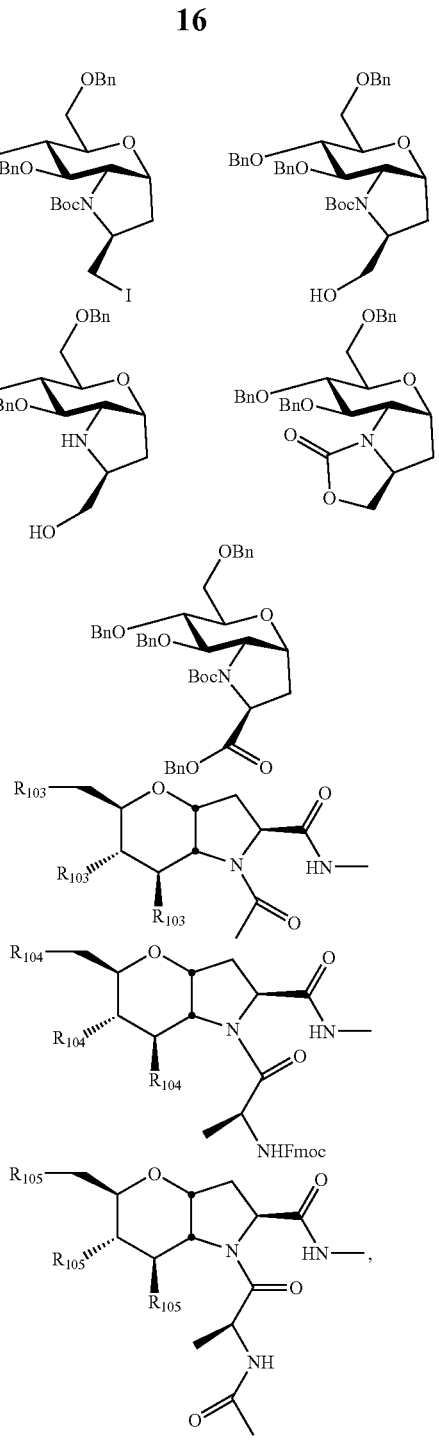

Other general aspects of the present invention contemplate a method of peptide or peptidomimetic synthesis, wherein a spirocyclic sugar-proline is incorporated into the peptide or peptidomimetic. Typically in these syntheses, functional groups (such as amine groups) of spirocyclic sugar-prolines will be orthogonally protected by protecting groups that will facilitate peptide synthesis, as known to those of skill in the art.

In certain embodiments, a tetrahydropyranyl-derivatized amino acid of the present invention is further defined as a fused bicyclic sugar-proline of formula (VI):

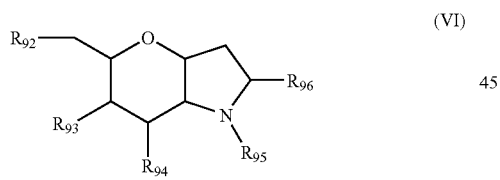

(VI)

wherein: $R_{92}$-$R_{94}$ are each independently —$OR_{97}$, wherein $R_{97}$ is —H or a hydroxy protecting group; $R_{95}$ is —H, alkyl, aryl, an amine protecting group, or —$COR_{98}$, wherein $R_{98}$ is alkyl, aryl, —$C_\alpha H(Y)NHR_{99}$, or —$CH(CH_3)NHR_{99}$, wherein: $C_\alpha$ is the alpha-carbon of the amino acid; $R_{99}$ is —H or an amine protecting group; and Y is the side chain of the amino acid; or $R_{95}$ together with $R_{96}$ forms a 2-oxazolidinonyl group; $R_{96}$ is —$CH_2$-halo, —$CH_2OH$ or —$C(O)R_{99}$, wherein $R_{99}$ is —NH-alkyl, such as —$NHCH_3$, or —$OR_{100}$, wherein $R_{100}$ is —H, alkyl, aryl, or a carboxyl protecting group (such as benzyl); or $R_{96}$ together with $R_{95}$ forms a 2-oxazolidinonyl group. The sugar may be any tetrahydropyranyl-based sugar known to those of skill in the art, such as glucosyl, mannosyl, or galactosyl.

In certain embodiments, the fused bicyclic sugar-proline is further defined as one or more of the following compounds:

wherein $R_{101}$, $R_{103}$, $R_{104}$ and $R_{105}$ are each independently —$OR_{106}$, wherein $R_{106}$ is —H or a hydroxy protecting group.

Also contemplated by the present invention are methods of synthesizing fused bicyclic sugar-prolines. In certain embodiments, a method of synthesizing a fused bicyclic sugar-proline comprises:
  a) protecting the $C_2$-amino-substituted function of a fully hydroxy protected, C1-vinyl substituted sugar;
  b) installing a pyrrolidine ring under amino-iodocyclization conditions to form a fused bicyclic sugar-pyrrolidine;
  c) converting the fused bicyclic sugar-pyrrolidine into a fused tricyclic carbamate;

d) hydrolyzing the carbamate to provide an amino alcohol;
e) protecting the amino group of the amino alcohol to provide an amino-protected fused bicyclic sugar-proline;
f) optionally oxidizing the alcohol of the amino alcohol to form a carboxylic acid; and
g) optionally protecting the carboxylic acid of step f).

In certain embodiments regarding methods of synthesizing fused bicyclic sugar-prolines, a compound of formula (VII) may be formed as an intermediate:

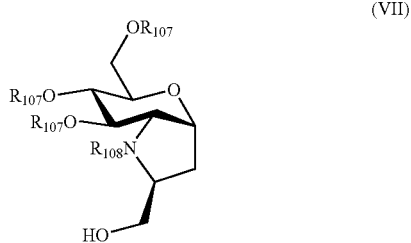

(VII)

wherein: $R_{107}$ is a hydroxy protecting group, such as acetyl; and $R_{108}$ is —H or an amine protecting group.

Other general aspects of the present invention contemplate a method of peptide or peptidomimetic synthesis, wherein a fused bicyclic sugar-proline is incorporated into the peptide or peptidomimetic. Typically in these syntheses, functional groups (such as amine groups) of fused bicyclic sugar-prolines will be orthogonally protected by protecting groups that will facilitate peptide synthesis, as known to those of skill in the art. In certain methods of peptide synthesis, the method comprises:

a) coupling the carboxylic acid of step f) above with methylamine to form an amide;
b) deblocking the protected amine; and
c) coupling the amine with an amine-protected amino acid, such as Fmoc-Ala-Cl or Fmoc-Gly-OH;
d) optionally deblocking of the amine-protected amino acid; and
e) optionally deblocking one or more of the hydroxy groups of the sugar.

In certain embodiments, a fused bicyclic sugar-proline of the present invention as incorporated into a peptide or peptidomimetic may alter the cis/trans ratio of the peptide or peptidomimetic relative to the cis/trans ratio of the peptide or peptidomimetic without the fused bicyclic sugar-proline.

In certain embodiments, a first fused bicyclic sugar-proline affects the cis/trans ratio of a peptide or peptidomimetic relative to the cis/trans ratio of the peptide or peptidomimetic having a second fused bicyclic sugar-proline substituted for the first fused bicyclic sugar-proline, wherein the first fused bicyclic sugar-proline comprises different —OR groups on the sugar than the —OR' groups of the sugar of the second fused bicyclic sugar-proline, wherein R and R' are —OH or protected hydroxy. In certain embodiments, the solvent in which the peptide synthesis takes place affects the cis/trans ratio of the peptide. The solvent may be, for example, water, DMSO, $d_6$-DMSO, $CH_3OH$, $CD_3OD$, $CHCl_3$, $CDCl_3$, or any combination thereof.

Any tetrahydropyranyl-derivatized amino acid and/or peptide or peptidomimetic comprising a tetrahydropyranyl-derivatized amino acid may be comprised in a pharmaceutically acceptable composition. Pharmaceutical compositions of the present invention comprise an effective amount of one or more tetrahydropyranyl-derivatized amino acids or additional agents dissolved or dispersed in a pharmaceutically acceptable carrier. The term "effective," as that term is used in the specification and/or claims (e.g., "an effective amount,") means adequate to accomplish a desired, expected, or intended result. The phrases "pharmaceutical or pharmacologically acceptable" refer to molecular entities and compositions that do not produce an adverse, allergic or other untoward reaction when administered to an animal, such as, for example, a human, as appropriate. The preparation of a pharmaceutical composition that contains at least one tetrahydropyranyl-derivatized amino acid or additional active ingredient will be known to those of skill in the art in light of the present disclosure, as exemplified by Remington's Pharmaceutical Sciences, 18th Ed. Mack Printing Company, 1990, incorporated herein by reference. A pharmaceutically acceptable composition may comprise one or more pharmaceutically acceptable salts; such salts are well-known to those of skill in the art. Non-limiting examples of pharmaceutically acceptable salts and their methods of preparation and use are presented in *Handbook of Pharmaceutical Salts: Properties, Selection and Use* (2002), which is incorporated herein by reference. It should be recognized that the particular anion or cation forming a part of any salt of this invention is typically not critical, so long as the salt, as a whole, is pharmacologically acceptable.

A tetrahydropyranyl-derivatized amino acid may be contacted with a cell, or may be administered to a subject. A tetrahydropyranyl-derivatized amino acid may be administered in an amount effective to treat a subject, such as a subject suffering from a bacterial or fungal infection, to produce a therapeutic benefit. A subject may be a mammal, such as a human.

The terms "contacted" and "exposed," when applied to a cell, are used herein to describe the process by which a compound of the present invention is administered or delivered to a target cell or are placed in direct juxtaposition with the target cell. The terms "administered" and "delivered" are used interchangeably with "contacted" and "exposed."

"Treatment" and "treating" as used herein refer to administration or application of a therapeutic agent, such as a tetrahydropyranyl-derivatized amino acid, to a subject or performance of a procedure or modality on a subject for the purpose of obtaining a therapeutic benefit of a disease or health-related condition.

The term "therapeutic benefit" or "therapeutically effective" as used throughout this application refers to anything that promotes or enhances the well-being of the subject with respect to the medical treatment of a condition. This includes, but is not limited to, a reduction in the frequency or severity of the signs or symptoms of a disease.

The term "amino acid" refers to any of the naturally occurring amino acids, as well as synthetic analogs (e.g., D-stereoisomers of the naturally occurring amino acids, such as D-threonine) and derivatives thereof. L-stereoisomers are also specifically encompassed by the present invention. α-Amino acids comprise a carbon atom to which is bonded an amino group, a carboxyl group, a hydrogen atom, and a distinctive group referred to as a "side chain." The side chains of naturally occurring amino acids are well known in the art and include, for example, hydrogen (e.g., as in glycine), alkyl (e.g., as in alanine, valine, leucine, isoleucine, proline), heteroatom-substituted alkyl (e.g., as in threonine, serine, methionine, cysteine, aspartic acid, asparagine, glutamic acid, glutamine, arginine, and lysine), arylalkyl (e.g., as in phenylalanine and tryptophan), heteroatom-substituted arylalkyl (e.g., as in tyrosine), and heteroatom-substituted arylalkyl (e.g., as in histidine). Unnatural amino acids are also known in the art, as set forth in, for example, Williams (1989); Evans et al. (1990); Pu et al. (1991); Williams et al (1991); and all references cited therein. The present invention includes the side chains of unnatural amino acids as well. Amino acids comprising an additional methylene group in their backbone are often called β-amino acids; such amino acids are also encompassed by the present invention.

As used herein, the term "peptide" refers to a compound comprising two or more amino acid residues wherein the amino group of one amino acid is linked to the carboxyl group of another amino acid by a peptide bond. A peptide can be, for example, derived or removed from a native protein by enzymatic or chemical cleavage, or can be prepared using conventional peptide synthesis techniques (e.g., solid phase synthesis) or molecular biology techniques (see Sambrook, 1989).

As used herein, the term "peptidomimetic" refers to molecules which are not peptides, but which mimic aspects of their structures. Peptidomimetics are well-known to those of skill in the art. For example, peptidomimetic may mimic or antagonize the biological action of a natural parent peptide molecule. Certain peptidomimetics comprise chemical bonds that are not susceptible to enzymatic cleavage, as opposed to their parent peptide molecules.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
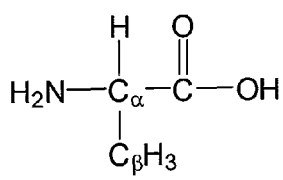
FIG. 1. Non-limiting examples of tetrahydropyranyl-derivatized amino acids. The tetrahydropyran may be further defined as a monosaccharide.
Figure 1:
Figure 1:
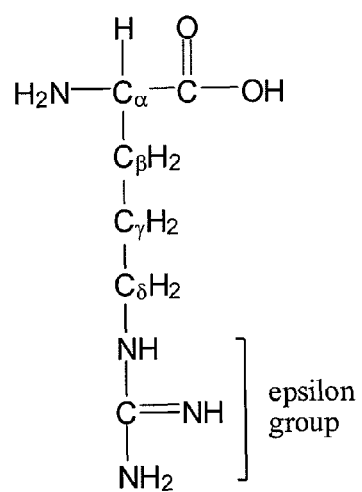
Figure 1:
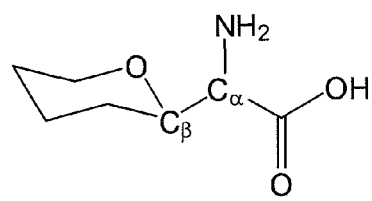
Figure 1:
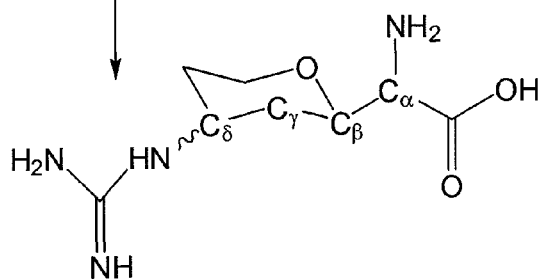
Figure 2:
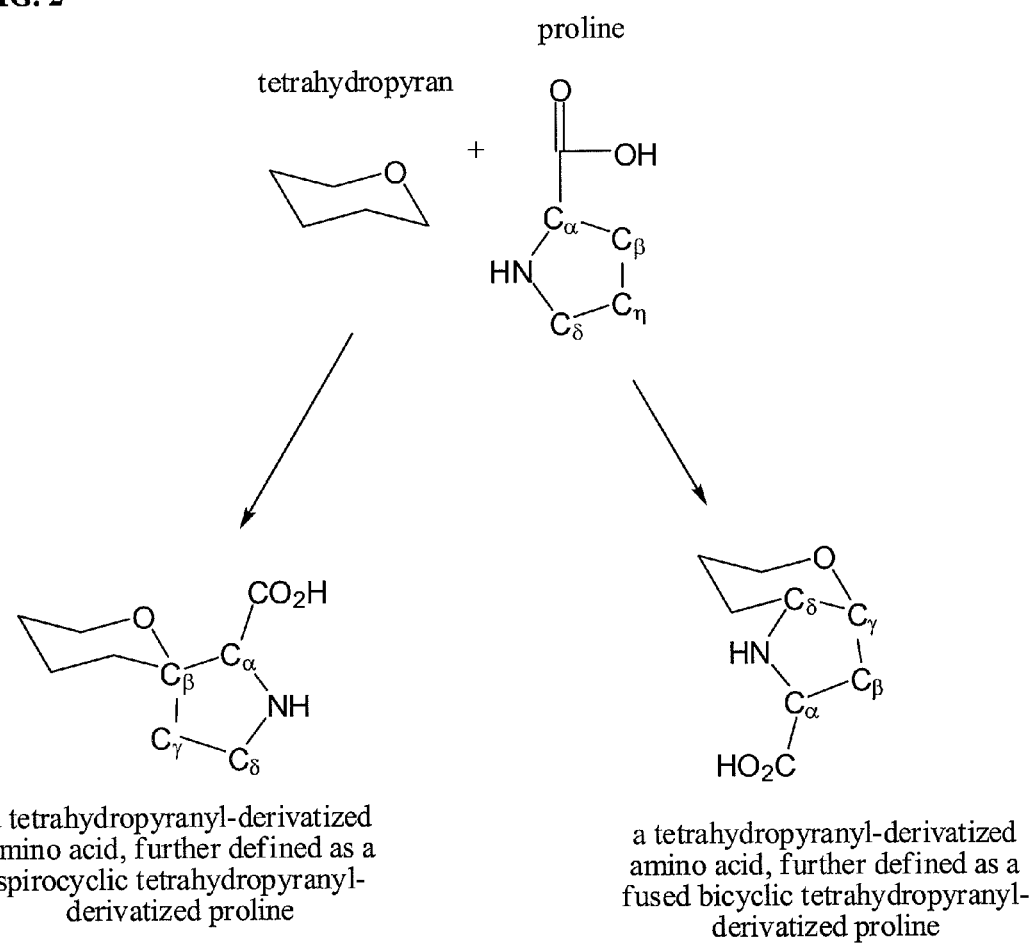
FIG. 2. Non-limiting examples of tetrahydropyranyl-derivatized amino acids. The tetrahydropyran may be further defined as a monosaccharide.

The present invention overcomes the deficiencies of the prior art by providing tetrahydropyranyl-derivatized amino acids, such as sugar-amino acid hybrids that, through templating the amino acid side chain to a tetrahydropyranyl (e.g., sugar) moiety, constrain the amino acid side chain. These polyfunctional hybrids may be incorporated into peptides and peptidomimetics, such as antimicrobial peptides. They may also act as sugar mimetics or as scaffolds for combinatorial synthesis.

A. Post-translational Hydroxylation and Glycosylation

Peptides and proteins often undergo post-translational modifications that may significantly affect their properties. For example, post-translational hydroxylation of lysine (Taylor et al., 2000), arginine (Taylor et al., 2000) and other amino acids (Reddy et al., 1998; Baldwin et al, 1993; Postels and Koenig, 1994) enhances the biological activity of certain antimicrobial peptides (AMPs) (Taylor et al., 2000). Post-translational glycosylation of the antimicrobial peptide drosocin (Bulet et al., 1993; Bulet et al., 1996) provided analogs with increased antibacterial activity.

Polyhydroxylated amino acids may induce novel secondary structures in small peptides. For instance, incorporation of unprotected sugar amino acids into small peptides such as gramicidin S (Grotenbreg et al., 2004) and opioid peptides (Chakraborty et al., 1998) prohibited the formation of the targeted secondary structural motif. Instead, unusual turn structures stabilized by intramolecular hydrogen bonds between sugar hydroxyl groups and the peptidic amide backbone were observed.

The tetrahydropyranyl-derivatized amino acids of the present invention offer novel opportunities for hydroxylation and glycosylation effects of peptides to be studied. For example, compound 1, shown below

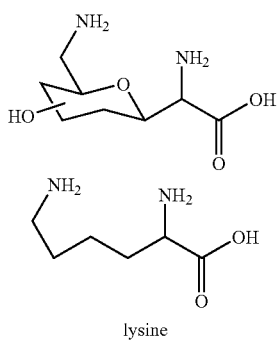

lysine contains the gluco-configured RNA 1,3-hydroxyamine binding motif (Wong et al., 1998) of aminoglycoside antibiotics that has been proposed to interact as bidentate RNA hydrogen bond acceptor to the phosphodiester backbone or Hoogsteen face of guanosine:

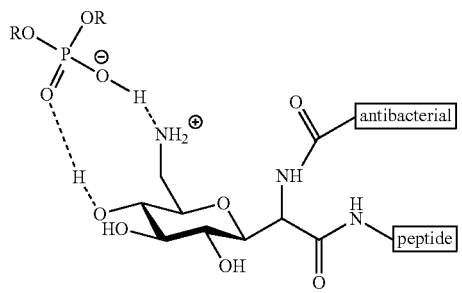

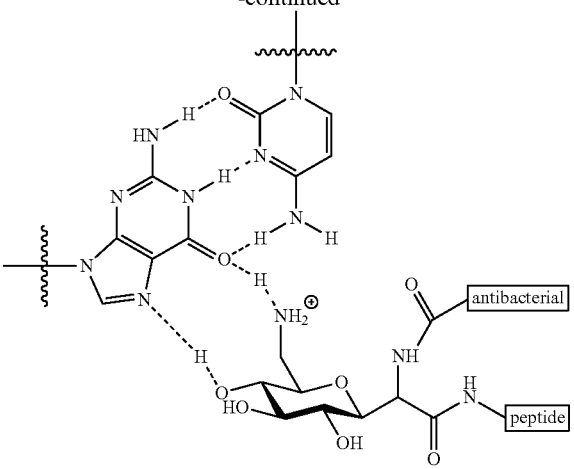

Incorporation of 1 into short antibacterial peptides may introduce novel and synergistic effects which could improve the biological, pharmacological, and/or chemical properties of antibacterial peptides.

The peptides into which tetrahydropyranyl-derivatized amino acids of the present invention may be incorporated are not limited to antimicrobial peptides. Compounds of the present invention may be incorporated into any peptide or peptidomimetic of biological interest. Derivatization or decoration of the polyol scaffold may be used as a tool to tailor the chemical, physical, biological, and/or conformational properties of peptides and peptidomimetics into which tetrahydropyranyl-derivatized amino acids of the present invention are incorporated.

B. Proline cis/trans Equilibria

Unlike other natural amino acids, proline features a side chain that is fused onto the peptide backbone. This trait restricts the rotation about its ø dihedral angle, thereby reducing the energy difference between the prolyl amide cis- and trans-isomers, making them nearly isoenergetic. Thus, while most peptide amide bonds exist almost exclusively in the trans form, proline has a much greater propensity to form cis amide bonds. This feature causes proline to play a key role in inducing a reversal in peptide backbone conformation (Wilmot and Thornton, 1988). In another important role, proline cis-trans isomerization becomes the rate-determining step in the folding pathways of peptides and proteins (Fischer and Schmid, 1990). Variation of the trans/cis ratio may aid in understanding the behavior of peptides and proteins. However, different proline analogs are required to induce a desired bias in Kt/c. Moreover, none of the present building blocks have strategic functional groups positioned for further derivatization in order to alter the amide equilibrium.

Fused bicyclic sugar prolines of the present invention overcome deficiencies in the art in that these single moieties may be used to study both cis and trans equilibria shifts, even after incorporation into a peptide. In particular, glucose, with its stable chair conformation, provides a useful scaffold to template proline since it freezes the orientation of four proline atoms ($C_\beta$, $C_\gamma$, $C_\delta$, N), while the sugar hydroxyl groups amend themselves to derivatization of the building block as potential sites for influencing the peptide backbone conformation.

C. Chemical Definitions

As used herein, the term "amino" means —$NH_2$; the term "nitro" means —$NO_2$; the term "halo" designates —F, —Cl, —Br or —I; the term "mercapto" or "thiol" means —SH; the term "cyano" means —CN; the term "azido" means —$N_3$; the term "silyl" means —$SiH_3$, and the term "hydroxy" means —OH.

The term "alkyl" includes straight-chain alkyl, branched-chain alkyl, cycloalkyl (alicyclic), cyclic alkyl, heteroatom-unsubstituted alkyl, heteroatom-substituted alkyl, heteroatom-unsubstituted $C_n$-alkyl, and heteroatom-substituted $C_n$-alkyl. In certain embodiments, lower alkyls are contemplated. The term "lower alkyl" refers to alkyls of 1-6 carbon atoms (that is, 1, 2, 3, 4, 5 or 6 carbon atoms). The term "heteroatom-unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The groups, —$CH_3$ (Me), —$CH_2CH_3$ (Et), —$CH_2CH_2CH_3$ (n-Pr), —$CH(CH_3)_2$ (iso-Pr), —$CH(CH_2)_2$ (cyclopropyl), —$CH_2CH_2CH_2CH_3$ (n-Bu), —$CH(CH_3)$ $CH_2CH_3$ (sec-butyl), —$CH_2CH(CH_3)_2$ (iso-butyl), —$C(CH_3)_3$ (tert-butyl), —$CH_2C(CH_3)_3$ (neo-pentyl), cyclobutyl, cyclopentyl, and cyclohexyl, are all non-limiting examples of heteroatom-unsubstituted alkyl groups. The term "heteroatom-substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all non-limiting examples of heteroatom-substituted alkyl groups: trifluoromethyl, —$CH_2F$, —$CH_2Cl$, —$CH_2Br$, —$CH_2OH$, —$CH_2SH$, —$CH_2OCH_3$, —$CH_2OCH_2CF_3$, —$CH_2OC(O)CH_3$, —$CH_2NH_2$, —$CH_2NHCH_3$, —$CH_2N(CH_3)_2$, —$CH_2CH_2Cl$, —$CH_2CH_2OH$, $CH_2CH_2OC(O)CH_3$, —$CH_2CH_2NHCO_2C$ $(CH_3)_3$, and —$CH_2Si(CH_3)_3$.

The term "aryl" includes heteroatom-unsubstituted aryl, heteroatom-substituted aryl, heteroatom-unsubstituted $C_n$-aryl, heteroatom-substituted $C_n$-aryl, heteroaryl, heterocyclic aryl groups, carbocyclic aryl groups, biaryl groups, and single-valent radicals derived from polycyclic fused hydrocarbons (PAHs). The term "heteroatom-unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted $C_6$-$C_{10}$-aryl has 6 to 10 carbon atoms. Non-limiting examples of heteroatom-unsubstituted aryl groups include phenyl (Ph), methylphenyl, (dimethyl)phenyl, —$C_6H_4CH_2CH_3$, —$C_6H_4CH_2CH_2CH_3$, —$C_6H_4CH(CH_3)_2$, —$C_6H_4CH(CH_2)_2$, —$C_6H_3(CH_3)CH_2CH_3$, —$C_6H_4CH=CH_2$, —$C_6H_4CH=CHCH_3$, —$C_6H_4C\equiv CH$, —$C_6H_4C\equiv CCH_3$, naphthyl, and the radical derived from biphenyl. The term "heteroatom-substituted $C_n$-aryl" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-heteroaryl has 1 to 10 carbon atoms. Non-limiting examples of heteroatom-substituted aryl groups include the groups: —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OC$ $(O)CH_3$, —$C_6H_4NH_2$, —$C_6H_4NHCH_3$, —$C_6H_4N(CH_3)_2$, —$C_6H_4CH_2OH$, —$C_6H_4CH_2OC(O)CH_3$, —$C_6H_4CH_2NH_2$, —$C_6H_4CF_3$, —$C_6H_4CN$, —$C_6H_4CHO$, —$C_6H_4CHO$, —$C_6H_4C(O)CH_3$, —$C_6H_4C(O)C_6H_5$, —$C_6H_4CO_2H$, —$C_6H_4CO_2CH_3$, —$C_6H_4CONH_2$, —$C_6H_4CONHCH_3$, —$C_6H_4CON(CH_3)_2$, furanyl, thienyl, pyridyl, pyrrolyl, pyrimidyl, pyrazinyl, quinolyl, indolyl, and imidazoyl.

The term "aralkyl" includes heteroatom-unsubstituted aralkyl, heteroatom-substituted aralkyl, heteroatom-unsubstituted $C_n$-aralkyl, heteroatom-substituted $C_n$-aralkyl, heteroaralkyl, and heterocyclic aralkyl groups. In certain embodiments, lower aralkyls are contemplated. The term "lower aralkyl" refers to aralkyls of 7-12 carbon atoms (that is, 7, 8, 9, 10, 11 or 12 carbon atoms). The term "heteroatom-unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted $C_7$-$C_{10}$-aralkyl has 7 to 10 carbon atoms. Non-limiting examples of heteroatom-unsubstituted aralkyls are: phenylmethyl (benzyl, Bn) and phenylethyl. The term "heteroatom-substituted $C_n$-aralkyl" refers to a radical, having a single saturated carbon atom as the point of attachment, further having a total of n carbon atoms, 0, 1, or more than one hydrogen atom, and at least one heteroatom, wherein at least one of the carbon atoms is incorporated an aromatic ring structures, further wherein each heteroatom is independently selected from the group consisting of N, O, F, Cl, Br, I, Si, P, and S. For example, a heteroatom-substituted $C_2$-$C_{10}$-heteroaralkyl has 2 to 10 carbon atoms.

The term "alkylthio" includes straight-chain alkylthio, branched-chain alkylthio, cycloalkylthio, cyclic alkylthio, heteroatom-unsubstituted alkylthio, heteroatom-substituted alkylthio, heteroatom-unsubstituted $C_n$-alkylthio, and heteroatom-substituted $C_n$-alkylthio. In certain embodiments, lower alkylthios are contemplated. The term "lower alkylthio" refers to alkylthios of 1-6 carbon atoms (that is, 1, 2, 3, 4, 5 or 6 carbon atoms). The term "heteroatom-unsubstituted $C_n$-alkylthio" refers to a group, having the structure —SR, in which R is a heteroatom-unsubstituted $C_n$-alkyl, as that term is defined above. The group, —$SCH_3$, is an example of a heteroatom-unsubstituted alkylthio group. The term "heteroatom-substituted $C_n$-alkylthio" refers to a group, having the structure —SR, in which R is a heteroatom-substituted $C_n$-alkyl, as that term is defined above.

Modifications or derivatives of the compounds, agents, and active ingredients disclosed throughout this specification are contemplated as being useful with the methods and compositions of the present invention. Derivatives may be prepared and the properties of such derivatives may be assayed for their desired properties by any method known to those of skill in the art.

In certain aspects, "derivative" refers to a chemically modified compound that still retains the desired effects of the compound prior to the chemical modification. "Tetrahydropyranyl-derivatized amino acid derivatives," therefore, refers to a chemically modified compound that still retains the desired effects of the parent tetrahydropyranyl-derivatized amino acid prior to its chemical modification. Such effects may be enhanced (e.g., slightly more effective, twice as effective, etc.) or diminished (e.g., slightly less effective, 2-fold less effective, etc.) relative to the parent tetrahydropyranyl-derivatized amino acid, but may still be considered a tetrahydropyranyl-derivatized amino acid derivative. Such derivatives may have the addition, removal, or substitution of one or more chemical moieties on the parent molecule. Non-limiting examples of the types modifications that can be made to the compounds and structures disclosed herein include the addition or removal of lower unsubstituted alkyls such as methyl, ethyl, propyl, or substituted lower alkyls such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom. Amino acid derivatives are also contemplated in this regard.

Prodrugs and solvates of the compounds of the present invention are also contemplated herein. That is, any tetrahydropyranyl-derivatized amino acid may be a prodrug. The term "prodrug" as used herein, is understood as being a compound which, upon administration to a subject, such as a mammal, undergoes chemical conversion by metabolic or chemical processes to yield a compound any of the formulas herein, or a salt and/or solvate thereof (Bundgaard, 1991; Bundgaard, 1985). For example, certain tetrahydropyranyl-derivatized amino acids may be hydroxylated in vivo, such that the hydroxylated product is the active agent. Solvates of the compounds of the present invention are preferably hydrates.

As used herein, the term "nucleophile" or "nucleophilic" generally refers to atoms bearing lone pairs of electrons. Such terms are well known in the art and include —$NH_2$, thiolate, carbanion and hydroxyl.

The term "functional group" generally refers to how persons of skill in the art classify chemically reactive groups. Examples of functional groups include hydroxyl, amine, sulfhydryl, amide, carboxyls, carbonyls, etc.

Compounds of the present invention may contain one or more asymmetric centers and thus can occur as racemates and racemic mixtures, single enantiomers, diastereomeric mixtures and individual diastereomers. In certain embodiments, a single diastereomer is present. All possible stereoisomers of the compounds of the present invention are contemplated as being within the scope of the present invention. However, in certain aspects, particular diastereomers are contemplated. The chiral centers of the compounds of the present invention can have the S- or the R-configuration, as defined by the IUPAC 1974 Recommendations. In certain aspects, certain compounds of the present invention may comprise S- or R-configurations at particular carbon centers.

Solvent choices for the methods of the present invention will be known to one of ordinary skill in the art. Solvent choices may depend, for example, on which one(s) will facilitate the solubilizing of all the reagents or, for example, which one(s) will best facilitate the desired reaction (particularly when the mechanism of the reaction is known). Solvents may include, for example, polar solvents and non-polar solvents. Solvents choices include, but are not limited to, tetrahydrofuran, dimethylformamide, dimethylsulfoxide, dioxane, methanol, ethanol, hexane, methylene chloride and acetonitrile. More than one solvent may be chosen for any particular reaction or purification procedure. Water may also be admixed into any solvent choice. Further, water, such as distilled water, may constitute the reaction medium instead of a solvent.

Persons of ordinary skill in the art will be familiar with methods of purifying compounds of the present invention. One of ordinary skill in the art will understand that compounds of the present invention can generally be purified at any step, including the purification of intermediates as well as purification of the final products. In preferred embodiments, purification is performed via silica gel column chromatography or HPLC.

In view of the above definitions, other chemical terms used throughout this application can be easily understood by those of skill in the art. Terms may be used alone or in any combination thereof.

D. Protecting Groups

When a chemical reaction is to be carried out selectively at one reactive site in a multifunctional compound, other reactive sites may be temporarily blocked. A "protecting group," as used herein, is defined as a group used for the purpose of this temporary blockage. Compounds of the present invention are specifically contemplated in both their unprotected and protected forms.

There are a number of methods well known to those skilled in the art for accomplishing such a step. For protecting agents and their installation and removal, see, e.g., Greene and Wuts, 1999, herein incorporated by reference in its entirety. The function of a protecting group is to protect one or more functional groups (e.g., —$NH_2$, —OH, —SH, —COOH) during subsequent reactions which would not proceed well, either because the free (in other words, unprotected) functional group would react and be functionalized in a way that is inconsistent with its need to be free for subsequent reactions, or the free functional group would interfere in the reaction. The same protecting group may be used to protect one or more of the same or different functional group(s). Also, different protecting groups can be used to protect the same type of functional group within a compound of the present invention.

When a protecting group is no longer needed, it may be removed by methods well known to those skilled in the art. Agents used to remove the protecting group (that is, deblocking) may be called deprotecting agents. Protecting groups are readily removable (as is known to those skilled in the art) by methods employing deprotecting agents that are well known to those skilled in the art. It is well known that certain deprotecting agents remove some protective groups and not others, while other deprotecting agents remove several types of protecting groups from several types of functional groups. Thus, a first deprotecting agent may be used to remove one type of protecting group, followed by the use of a second deprotecting agent to remove a second type of protecting group, and so on. Persons of ordinary skill in the art will be familiar with the proper ordering of protective group removal using deprotecting agents. See e.g., Greene and Wuts (1999). Particular non-limiting examples of protecting groups are discussed below.

1. Amine Protecting Groups

Amine protecting groups are well known to those skilled in the art. See, for example, Greene and Wuts (1999) Chapter 7.

Non-limiting examples of amine protecting groups include t-butoxycarbonyl (Boc), benzyloxycarbonyl (Cbz), formyl, trityl, acetyl, trichloroacetyl, dichloroacetyl, chloroacetyl, trifluoroacetyl, difluoroacetyl, fluoroacetyl, benzyl chloroformate, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluoyl)prop-2-yloxycarbonyl, cyclopentanyloxycarbonyl, 1-methylcyclopentanyloxycarbonyl, cyclohexanyloxycarbonyl, 1-methylcyclohexanyloxycabonyl, 2-methylcyclohexanyloxycarbonyl, 2-(4-toluoylsulfonyl)ethoxycarbonyl, 2-(methylsulfonyl)ethoxycarbonyl, 2-(triphenylphosphino)ethoxycarbonyl, fluorenylmethoxycarbonyl (Fmoc), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxyl)benzyloxycarbonyl, isobornyloxycarbonyl, 1-piperidyloxycarbonyl, 4-methoxy-2,3,6-trimethylbenzenesulfonyl (Mtr), mesitylene-2-sulfonyl (Mts), tosyl (4-toluenesulfonyl) (Tos), 2,2,4,6,7-pentamethyldihydrobenzofuran-5-sulfonyl (Pbf), 2,2,5,7,8-pentamethylchroman-6-sulfonyl (Pmc), 4-methoxybenzenesulfonyl (Mbs) and 9-fluorenylmethyl carbonate, for example.

2. Thiol Protecting Groups

Thiol protecting groups are well known to those skilled in the art. See, for example, Greene and Wuts (1999) Chapter 6. Non-limiting examples of thiol protecting groups include acetamidomethyl, benzamidomethyl, 1-ethoxyethyl, benzoyl, triphenylmethyl, t-butyl, benzyl, adamantyl, cyanoethyl, acetyl, and trifluoroacetyl.

3. Hydroxy Protecting Groups

Alcohol protecting groups are well known to those skilled in the art. See, for example, Greene and Wuts (1999) Chapter 2. Non-limiting examples of hydroxy protecting groups include benzyl, methoxymethyl, (phenyldimethylsilyl)methoxymethyl, benzyloxymethyl, t-butoxymethyl, tetrahydropyranyl, and —OSiR$_3$, —OCOR and —OCONHR, wherein R is alkyl, phenyl or benzyl.

4. Carboxylic Acid (Carboxyl) Protecting Groups

Carboxylic acid protecting groups are well known to those skilled in the art. See, for example, Greene and Wuts (1999) Chapter 5. Non-limiting examples of carboxylic acid protecting groups include trifluoroacetyl, dimethylacetal, methoxymethylester, phenylacetoxymethyl ester and tetrahydropyranyl ester.

5. Guanidine Protecting Groups

Guanidine protecting groups are well known to those skilled in the art. Non-limiting examples of guanidine protecting groups include nitro, tosyl, benzyloxycarbonyl, adamantyloxycarbonyl, isobornyloxycarbonyl, mesitylene-2-sulfonyl (Mts), 2,2,5,7,8-pentamethylcroman-6-sulphonyl, 4-methoxy-2,3,6-trimethylbenzene and 2,2,4,6,7-pentamethyldihydrobenzofuran-5-sulfonyl group (Pbf).

E. Examples

The following examples are included to demonstrate certain preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of Certain Sugar-Amino Acid Chimeras of the Present Invention and Peptide Synthesis Incorporating Same: Glycosidic-Lysine Chimera (GlcLysC)

Figure 3:
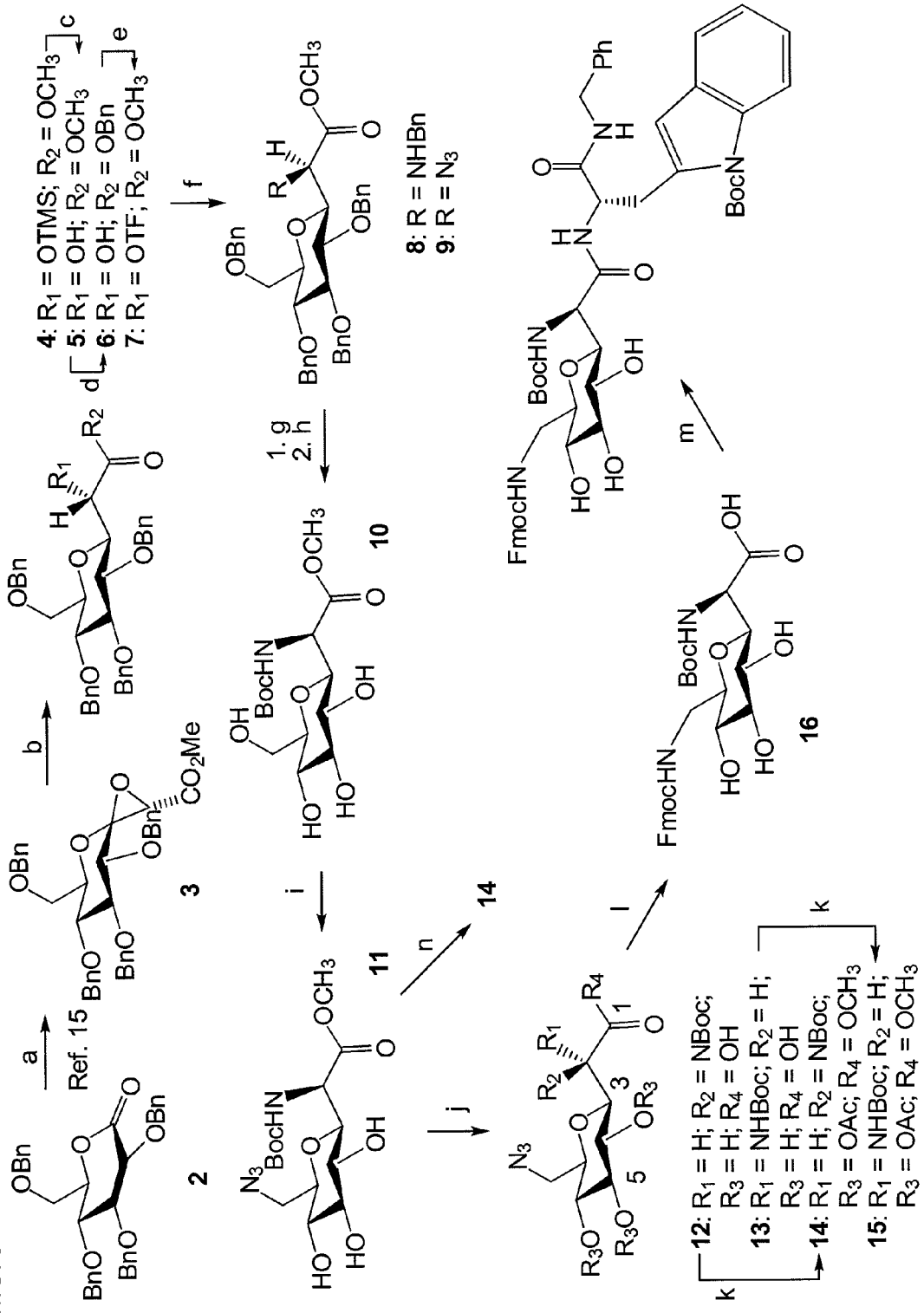
FIG. 3. A non-limiting method of generating a sugar-lysine chimera of the present invention. Reagents and conditions: (a) LiHMDS, $CH_2BrCOOMe$, THF, $-78°$ C.→r.t., 2 h, 80%; (b) $Bu_3SnH$, TMSOTf, $CH_2Cl_2$, $0°$ C., 30 min. 88%; (c) THF, TFA 2. eq. 2 h quant.; (d) (i) LiOH (3.0 eq.), THF, $H_2O$, 12 hr; (ii) $Cs_2CO_3$, BnBr, DMF, 4 hr. 89%; (e) $Tf_2O$, pyridine, $CH_2Cl_2$, $0°$ C. 1 hr, quant.; (f) $NaN_3$, $CH_2Cl_2$, 15-crown-5, rt, 24 hr, 81% or $BnNH_2$, $CH_2ClCH_2Cl$, $50°$ C., 24 hr, 56%; (g) $Pd(OH)_2$, MeOH, HCl (1.3 eq.), quant.; (h) MeOH, $Boc_2O$ (2 eq.), $Et_3NH$, 12 hr, 90%; (i) (i) TsCl (2.2 eq.), pyridine, rt, 12 hr; then work-up and $NaN_3$, DMF, $80°$ C., 12 hr, 65%; (j) LiOH (5 eq.), THF, $H_2O$, 8h; (k) (i) $Cs_2CO_3$, DMF, MeI work-up; (ii) $Ac_2O$, pyridine, 12h, quant.; (l) $Pd(OH)_2$, $H_2$, MeOH, 30 min. then FmocOPfp (2 eq.), $NaHCO_3$ (4 eq.), rt, acetone/$H_2O$: 3:1, 2 hr, 63%; (m) TBTU, H-Trp(Boc)-NHBn, DIEA, DMF, 80%; (n) $Ac_2O$/pyridine.

FIG. 3 depicts one method of generating a sugar-lysine chimera of the present invention, although variations of this method are possible, as known to those of skill in the art. The sugar-lysine chimera was then incorporated into the amphiphilic antimicrobial dipeptide sequence kW. Examples 2-11 describe the preparations of certain compounds of FIG. 3.

The synthesis started with the readily available D-gluco-configured lactone 2 (Gueyrard et al., 2005) (FIG. 3) which reacts with the enolate of α-bromo acetic acid methylester generated from lithium bis-(trimethylsilyl)amide (LiN(SiMe$_3$)$_2$) in tetrahydrofuran (THF) at −78° C., to produce the exocyclic epoxide 3 in 80% yield as a single stereoisomer (Zhang and Schweizer, 2005). Trimethylsilyltrifluoromethanesulfonate (TMSOTf)-promoted reductive ring opening of epoxide 3 with tributyltin hydride in dichloromethane at 0° C. afforded a mixture containing silylether 4 and alcohol 5 (ratio: 4:5=3.5:1) in a combined yield of 88%. Compounds 4 and 5 were obtained as a single diastereoisomer. The silylether 4 was hydrolyzed quantitatively into alcohol 5 by exposure to trifluoroacetic acid containing wet THF. The stereochemistry at C-2 of alcohol 5 was determined by conversion of 5 into the known benzylester 6 (Schweizer and Inazu, 2001). This was achieved in a two-step procedure. At first, methylester 5 was hydrolyzed to the corresponding acid with lithium hydroxide in wet THF. Subsequently, esterfication of the acid using cesium carbonate and benzylbromide in DMF afforded benzylester 6 as a single product in 89% yield. Hydroxyester 5 served as starting material to install an amino function at C-2. Initially, the hydroxyl group was activated as a trifluoromethanesulfonate ester 7 using trifluoromethanesulfonic anhydride in pyridine. Subsequently, the displacement reaction of triflate 7 was studied with two nucleophiles benzylamine and sodium azide. Both reactions provided the corresponding aminoester 8 and azide 9 in 56% and 81% yield, respectively. Catalytic hydrogenation of 8 and 9 using Pearlman's catalyst followed by protection of the amino function as tert-butyloxycarbamate provided protected amino ester 10 in 90% yield. Compound 10 served as starting material to introduce a second amino function into the carbohydrate scaffold. This was achieved by selective tosylation of the primary hydroxy position using p-toluenesulfonic chloride in pyridine followed by nucleophilic displacement of the tosylate with sodium azide to produce compound 11 in 65% isolated yield. Exposure of ester 11 to basic conditions (LiOH, THF/H$_2$O) resulted in partial epimerization at the C-2 position, affording an inseparable mixture of acids 12 and 13. Acids 12 and 13 were converted into the epimeric sugar lysine hybrids 14 and 15 (ratio 14/15:4/1) by esterfication (Cs$_2$CO$_3$, MeI, DMF) followed by acetylation of the hydroxyl groups (Ac$_2$O, pyridine). At this stage it was possible to separate the epimeric diastereomers by flash chromatography. The major diastereomer was identical to compound 14 previously obtained by acetylation of ester 11.

Compounds 14 and 15 exhibit characteristic $^1$H-NMR-data that confirm their structure. For instance, compound 14 shows the expected downfield shifts of H-4, H-5 and H-6 ($\delta_{H4,H5,H6}$>5.00 ppm) that are characteristic for O-acetylation at C-4, C-5 and C-6. By comparison, protons H-8a and H-8b in compound 15 appear high field ($\delta_{H8a,b}$=3.20–3.33 ppm), clearly indicating the installation of the azido function at C-8. In addition, the observed vicinal coupling constant between H-3 and H-4 of 9.3 Hz demonstrates the diaxial relationship of these protons and proves that no epimerization occurred at C-3 during treatment with LiOH. Analogously, the epimeric sugar lysine hybrid 15 exhibits chemical shifts and vicinal diaxial coupling constants ($\delta_{H4,H5,H6}$>5.00 ppm; $J_{H3,H4}$=9.9 Hz) that confirm its C-2 epimeric structure.

To demonstrate the use of GlcLysCs in peptide coupling reactions, azido acid 14 was converted into Fmoc-protected amino acid 16. This was achieved by catalytic hydrogenation followed by selective protection of the amino function using 9-fluorenylmethyl pentafluorophenyl carbonate (FmocOPfp) to produce 16 in 63% isolated yield. The lysine analog 16 is orthogonally protected to be used in solution-phase peptide coupling. To study the influence of the constrained sugar moiety and the presence of the gluco-configured 1,3-hydroxyamine motif on the bioactivity of small antibacterial peptides, GlcLysC was incorporated into the amphiphilic antimicrobial dipeptide sequence kW (Strom et al., 2003). This was achieved by coupling of 16 to H-Trp(Boc)NHBn using 2-(1H-benzotriazole-1yl)-1,1,3,3-tetra-methyluronium tetrafluoroborate (TBTU) as coupling reagent in DMF to produce dipeptide 17 in 80% isolated yield. During this coupling, ester formation was not observed as evidenced by MS analysis of the crude product or exposure to basic conditions ($K_2CO_3$, MeOH) as previously reported by Knorr et al. (1989).

Example 2

Synthesis of Compound 5 of Example 1

To a mixture of epoxide 3 (480 mg, 0.79 mmol) and tributyltin hydride (0.84 mL, 3.15 mmol) in dichloromethane (15 mL) was added dropwise trimethylsilyltrifluoromethanesulfonate (TMSOTf, 0.42 mL, 2.36 mmol) at 0° C. The mixture is stirred for 30 minutes at 0° C. before saturated sodium bicarbonate solution (15 mL) was added to quench the reaction. The organic layer was separated and the aqueous phase was extracted with dichloromethane (3×10 mL). The combined organic layer was dried ($Na_2SO_4$), concentrated and purified by flash column silica gel chromatography (hexanes:ethyl acetate, from 7:1 to 2:1) to afford 4 (388 mg) and 5 (96 mg) as a colorless syrup (96 mg). The trimethyl silyl ether 4 was converted to 5 (337 mg, quant.) by treatment with trifluoroacetic acid (0.19 mL, 5 equiv) in aqueous tetrahydrofuran (THF/$H_2O$: 5/1) overnight.

$^1$H NMR (300 MHz, CDCl$_3$, r.t., TMS): δ=2.85 (br, OH), 3.46-3.54 (m, 1H, H-7), 3.59 (dd, 1H, H-6, J=8.6 Hz, J=8.4 Hz), 3.63-3.72 (m, 3H, H-8a, H-8b H-3), 3.73-3.87 (m, 5H, OCH$_3$, H-4, H-5), 4.47-4.59 (m, 2H+H-2), 4.61 (d, 1H, J=11.0 Hz), 4.77 (d, 1H, J=11.0 Hz), 4.85 (d, 1H, J=10.8 Hz), 4.89-4.98 (m, 3H), 7.19-7.39 (m, 20H). $^{13}$C NMR (100 MHz, CDCl$_3$, r.t.): δ=52.67 (OCH$_3$), 68.98, 69.59, 73.35, 75.08, 75.16, 75.56, 77.78, 78.28, 79.51, 79.52, 86.88, 127.47-128.56 (aromatic carbons), 138.11, 138.23, 138.35, 138.58, 173.30 (C-1). MS (ES, [M+Na]$^+$); Anal. Calcd for C$_{37}$H$_{40}$NaO$_8$: 635.26, Found: 635.13. Anal. Calcd for C$_{37}$H$_{40}$O$_8$: C, 72.53; H, 6.58. Found: C, 72.71; H, 6.97.

Example 3

Synthesis of Compound 6 of Example 1

LiOH (24 mg, 1.02 mmol) was added to a mixture of compound 5 (104 mg, 0.17 mmol) in THF/$H_2O$ (3 mL, 1:1). The mixture was stirred at room temperature for 12 h and formic acid in $H_2O$ was added to quench the reaction until pH turned acidic. After extraction with ethyl acetate (5×20 mL), the organic layer was evaporated and the crude was dissolved in DMF (3 mL). Cs$_2$CO$_3$ (72 mg, 0.22 mmol) was added 30 minutes prior to addition of BnBr (40 μL, 0.34 mmol). The mixture was stirred at room temperature for 2 h and $H_2O$ was added. The aqueous phase was extracted with ethyl acetate (3×20 mL) and the combined organic phases were dried (Na$_2$SO$_4$) and concentrated. Flash column chromatography (hexanes:ethyl acetate, 4:1) yielded 6 (104 mg, 0.15 mmol, 89%).

$^1$H NMR (300 MHz, CDCl$_3$, r.t., TMS) δ=3.30-3.36 (br., m, 2H, H-7 and OH), 3.48 (dd, 1H, H-8a, J=1.7 Hz, J=11.1 Hz), 3.59-3.64 (m, 2H, H-6, H-8b), 3.67 (dd, H-3, J=1.9 Hz, J=8.6 Hz), 3.74 (dd, 1H, H-5, J=8.8 Hz, J=9.1 Hz), 3.83 (dd, 1H, H-4, J=9.1 Hz, J=8.6 Hz), 4.52-4.58 (m, 3H), 4.61 (d, 1H, J=10.7 Hz), 4.78 (d, 1H, J=10.9 Hz), 4.84 (d, 1H, J=10.9 Hz), 4.90-4.97 (m, 3H), 5.10 (d, 1H, J=12.0 Hz), 5.33 (d, 1H, J=12.0 Hz), 7.19-7.38 (m, 25H). $^{13}$C NMR (100 MHz, CDCl$_3$, r.t.): δ=67.3, 68.6, 69.6, 73.3, 75.1, 75.2, 75.6, 77.7, 78.1, 79.5, 79.6, 86.8, 127.6-128.6 (aromatic carbons), 135.3, 138.1, 138.2, 138.3, 138.6, 172.7. MS (ES, [M+H]$^+$); Anal. Calcd or C$_{43}$H$_{45}$O$_8$: 689.30, Found 689.44. Anal. Calcd for C$_{43}$H$_{44}$O$_8$: C, 74.98; H, 6.44. Found: C, 75.23; H, 6.81.

Example 4

Synthesis of Compound 8 of Example 1

Compound 5 (44 mg, 0.07 mmol) was dissolved in dry CH$_2$Cl$_2$ (2 mL) and cooled to 0° C. Pyridine (66 μL, 0.8 mmol) was added. The reaction mixture was stirred for 5 minutes, and then trifluoromethanesulfonic anhydride (48 μL, 0.28 mmol) was slowly added. The reaction mixture was stirred at 0° C. for 1 hour. $H_2O$ (5 mL) was added and followed by extraction with CH$_2$Cl$_2$. The organic layer was dried with Na$_2$SO$_4$, concentrated and redissolved in 1,2-dichloroethane (2 mL). NH$_2$Bn (78 μL, 0.7 mmol) was added and the reaction mixture was stirred at 50° C. for 24 h. The crude was concentrated and purified by flash column chromatography (hexane:ethyl acetate, 4:1) to yield 8 (28 mg, 0.04 mmol, 56%).

$^1$H NMR (300 MHz, CDCl$_3$, r.t., TMS) δ=3.10-2.90 (br., 1H, NH) 3.43-3.47 (m, 1H, H-7), 3.62 (s, 3H), 3.64 (dd, 1H, J=9.2 Hz, J=10.1 Hz), 3.69-3.80 (m, 7H), 3.94 (d, 1H, J=13.2 Hz), 4.53 (d, 1H, J=12.1 Hz), 4.62 (d, 1H, J=12.1 Hz), 4.65 (d, 1H, J=10.8 Hz), 4.75 (d, 1H, J=10.6 Hz), 4.83 (d, 1H, J=10.8 Hz), 4.86-4.90 (m, 2H), 4.94 (d, 1H, J=11.1 Hz), 7.15-7.37 (m, 25H). $^{13}$C NMR (100 MHz, CDCl$_3$, r.t.): δ=51.93, 52.44, 60.32, 68.79, 73.38, 74.64, 75.10, 75.64, 78.14, 78.35, 79.48, 81.35, 87.42, 127.1-139.6 (aromatic carbons), 171.7. MS (ES, [M+Na]$^+$); Anal. Calcd for C$_{44}$H$_{47}$NNaO$_7$: 724.33. Found: 724.45 Anal. Calcd for C$_{44}$H$_{47}$NO$_7$: C, 75.30; H, 6.75; N, 2.00. Found: C, 75.12; H, 6.93; N, 2.18.

Example 5

Synthesis of Compound 9 of Example 1

Compound 5 (50 mg, 0.08 mmol) was dissolved in dry $CH_2Cl_2$ (2 mL) and cooled to 0° C. Pyridine (66 µL, 0.8 mmol) was added. The reaction mixture was stirred for 5 minutes, and then trifluoromethanesulfonic anhydride (55 µL, 0.32 mmol) was slowly added. The reaction mixture was stirred under 0° C. for 1 h. $H_2O$ (5 mL) was added and followed by extraction with $CH_2Cl_2$ (3×5 mL). The organic layer was dried with $Na_2SO_4$, concentrated and re-dissolved in anhydrous $CH_2Cl_2$ (2 mL). $NaN_3$ (16 mg, 0.24 mmol) and 15-crown-5 (40 µL, 0.2 mmol) was added. The reaction mixture was stirred at room temperature for 24 h and then $H_2O$ was added. The aqueous phase was extracted with $CH_2Cl_2$ (3×20 mL) and the combined organic phases were dried ($Na_2SO_4$) and concentrated. Flash column chromatography (hexanes:ethyl acetate, 4:1) yielded azide 9 (42 mg, 0.066 mmol, 81%).

$^1$H NMR (300 MHz, $CDCl_3$, r.t., TMS) δ=3.52-3.56 (m, 4H, 3H+H-7), 3.64 (dd, 1H, H-6, J=9.6 Hz, J=8.6 Hz), 3.71-3.77 (m, 3H, H-5, H-8a,b), 3.80 (dd, 1H, H-4, J=9.4 Hz, J=8.6 Hz), 3.92 (dd, 1H, H-3, J=9.4 Hz, J=1.9 Hz), 4.37 (d, 1H, H-2, J=1.9 Hz), 4.55 (d, 1H, J=12.1 Hz), 4.57-4.65 (m, 2H), 4.69 (d, 1H, J=10.6 Hz), 4.83 (d, 1H, J=10.9 Hz), 4.88 (d, 1H, J=10.9 Hz), 4.93-4.97 (m, 2H), 7.23-7.36 (m, 20H). $^{13}$C NMR (100MHz, $CDCl_3$, r.t.): δ=52.6, 62.8, 68.9, 73.5, 74.7, 75.1, 75.6, 77.3, 78.2, 79.6, 79.7, 87.1, 127.6-128.5 (aromatic carbons), 137.9, 138.0, 138.2, 138.3, 167.8. MS (ES, [M+Na]$^+$); Anal. Calcd for $C_{37}H_{39}N_3NaO_7$: 660.27, Found: 660.03. Anal. Calcd for $C_{37}H_{39}N_3O_7$: C, 69.68; H, 6.16; N, 6.59. Found: C, 75.12; H, 6.93; N, 2.18.

Example 6

Synthesis of Compound 10 of Example 1

Compound 8 (223 mg, 0.32 mmol) was dissolved in MeOH (6 mL) and HCl (0.5 mmol). Pearlman's catalyst (160 mg) was added and the mixture was hydrogenated for 6 hrs at atmospheric pressure. The mixture was filtered, concentrated, and redissolved in MeOH (2 mL). Triethylamine (0.5 mL) and $Boc_2O$ (550 mg, 2.5 mmol) were added and the mixture was stirred at room temperature for 12 h. The crude was concentrated and chromatographed using 14% methanol in ethyl acetate to afford 10 (100 mg, 0.28 mmol, 90%) as a syrup.

$^1$H NMR (300 MHz, $CD_3OD$, r.t., TMS) δ=1.46 (s, 9H), 3.07 (dd, 1H, H-6, J=9.3 Hz, J=9.2 Hz), 3.23-3.36 (m, 2H, H-5, H-7), 3.43-3.59 (m, 3H, H-3, H-4, H-8a), 3.74 (s, 3H), 3.89 (dd, 1H, H-8b, J=11.8 Hz, J=1.9 Hz), 4.66 (d, 1H, H-2, J=<1 Hz). $^{13}$C NMR (100 MHz, $CD_3OD$, r.t.): δ=28.7, 52.6, 55.4, 63.6, 71.6, 72.0, 79.7, 80.8, 82.2, 82.6, 158.2, and 173.0. MS (ES, [M+H]$^+$): Anal. Calcd for $C_{14}H_{26}NO_9$: m/z calc. 352.15, Found: 352.29. HRMS Calcd for $C_{14}H_{26}NO_9$ [M+H]$^+$:352.1608. Found: 352.1607.

Example 7

Synthesis of Compound 11 of Example 1

To compound 10 (100 mg, 0.29 mmol) in dry pyridine (8 mL) was added tosyl chloride (128 mg, 0.68 mmol) and the reaction was stirred for 2 hours at 0° C., then raised to room temperature for 6 more hours. The solvent was removed in vacuo and then purified by gradient flash column silica gel chromatography (ethyl acetate to ethyl acetate: methanol, 20:1) to afford a crude mixture containing the 6-O-tosyl-β-D-glucopyranoside (92 mg, 0.18 mmol, 64%). The tosylate was dissolved in dry DMF (3 mL) sodium azide (118 mg, 1.82 mmol) was added and the mixture was heated to 80° C. overnight. The solvent was removed in vacuo and the residue was purified by gradient flash column silica gel chromatography (ethyl acetate:methanol, 20:1) to afford compound 11 (65 mg, 95%). A small sample of 11 (5 mg) was acetylated in a 1:1 mixture containing pyridine and acetic anhydride (0.5 mL).

$^1$H NMR (300 MHz, $CDCl_3$, r.t., TMS): δ=1.44 (s, 9H), 3.28-3.64 (m, 6H, H-3, H-5, H-6, H-7, H-8a, H-8b), 3.66-3.79 (m, 4H), 4.00-4.16 (br, 3×OH), 4.77 (d, 1H, H-2, J=8.4 Hz), 5.63 (d, 1H, J=8.4 Hz). $^{13}$C NMR (100 MHz, $CDCl_3$, r.t.): δ=28.30, 51.27, 52.63 ($OCH_3$), 53.86, 70.40, 70.58, 77.90, 79.46, 80.63, 80.84, 155.68, 169.59. HRMS (ES, [M+Na]$^+$): Anal. Calcd for $C_{14}H_{24}N_4NaO_8$ 399.1486, Found: 399.1484.

Example 8

Synthesis of Compounds 12-15 of Example 1

Ester 11 (60 mg, 0.16 mmol) was treated with lithium hydroxide (7 mg, 0.31 mmol) for 8 hours at room temperature in aqueous THF (1:1), and then acidified with formic acid (100 µL). The solution was extracted with ethyl acetate (6×10 mL) and the combined organic layer solvent was dried ($Na_2SO_4$) and concentrated to afford inseparable mixture of crude acids 12 and 13 (59 mg, quant.), which was treated with $Cs_2CO_3$ (61 mg, 0.18 mmol) and MeI (30 µl, 0.48 mmol) in DMF. The reaction was worked up with $H_2O$ and extracted with ethyl acetate (4×15 mL); the combined organic phases were dried ($Na_2SO_4$) and concentrated. The crude was acetylated by dissolving it in a 1:1 mixture containing acetic anhydride (0.5 mL) and pyridine (0.5 mL). The crude mixture was purified by the flash chromatography (ethyl acetate:hexanes, 1:2) to afford compound 14 (61 mg, 80%) and 15 (15 mg, 20%). Compound 14 was identical to the product obtained by acetylation of compound 11.

14: $^1$H NMR (300 MHz, $CDCl_3$, r.t., TMS) δ=1.45 (s, 9H), 2.00 (s, 3H), 2.02 (s, 3H), 2.05 (s, 3H), 3.20-3.33 (m, 2H), 3.64-3.70 (m, 1H, H-7), 3.77 (s, 3H), 3.87 (dd, 1H, H-3, J=9.9 Hz, J=1.7 Hz), 4.66 (dd, 1H, H-2, J=1.7 Hz, 9.2 Hz), 5.02 (dd, 1H, H-6, J=9.3 Hz, J=9.7 Hz), 5.16 (dd, 1H, H-5, J=9.3 Hz, J=9.1 Hz), 5.25 (dd, 1H, H-4, J=9.1 Hz, J=9.9 Hz), 5.46 (d, 1H, N—H, J=9.2 Hz). $^{13}$C NMR (100 MHz, $CDCl_3$, r.t.): δ=20.57, 20.58, 20.66, 28.27 (3 carbons), 50.83, 52.73, 53.47, 68.77, 69.03, 74.21, 77.77, 78.76, 80.46, 168.78, 168.80, 169.39, 169.51, 170.29. MS (ES, [M+Na]$^+$); Anal. Calcd for $C_{20}H_{30}N_4NaO_{11}$: 525.18, Found: 525.32. Anal. Calcd for $C_{20}H_{30}N_4O_{11}$: C, 47.81%, H, 6.02%, N: 11.15%. Found: C, 48.08%, H, 6.15%, N: 10.77%.

15: $^1$H NMR (300 MHz, $CDCl_3$, r.t., TMS) δ=1.44 (s, 9H), 1.98 (s, 3H), 2.03 (s, 3H), 2.04 (s, 3H), 3.13-3.29 (m, 2H, H-8a, H-8b), 3.64-3.71 (m, 1H, H-7), 3.78 (s, 3H), 4.16 (dd, 1H, H-3, J=9.9 Hz, J=2.3 Hz), 4.70 (dd, 1H, H-2, J=10.5 Hz, 2.3 Hz), 5.00 (dd, 1H, H-6, J=9.5 Hz, J=9.5 Hz), 5.06 (dd, 1H, H-4, J=9.9 Hz, J=9.5 Hz), 5.20 (dd, 1H, H-5, J=9.5 Hz, J=9.5 Hz), 5.13 (d, 1H, N—H, J=10.5 Hz). $^{13}$C NMR (100 MHz, $CDCl_3$, r.t.): δ=21.23, 21.34 (2 carbons), 28.88 (3 carbons), 51.30, 53.02, 53.46, 68.12, 69.84, 74.59, 78.04, 78.47, 79.82, 167.63, 168.12, 168.84, 169.37, 169.72. MS (ES, [M+Na]$^+$); Anal. Calcd for $C_{20}H_{30}N_4O_{11}$: 525.18, Found: 525.27. Anal.

Calcd for C$_{20}$H$_{30}$N$_4$O$_{11}$ C: 47.81%, H, 6.02%, N: 11.15%. Found: C: 47.98%, H, 6.25%, N: 11.55%.

Example 9

Synthesis of Compound 16 of Example 1

Acid 12 (46 mg, 0.12 mmol) was dissolved in MeOH (4 mL) and hydrogenated for 20 min. using 20% wt Pd/C. The solution was filtered and the solvent was evaporated in vacuo. The solid residue was dissolved in aqueous acetone (3 mL, 1:1) and treated with 9-fluorenylmethyl pentafluorophenyl carbonate (91 mg, 0.24 mmol) and sodium bicarbonate (31 mg, 0.37 mmol) for 4 hours at room temperature. Water (10 mL) was added and the aqueous layer was extracted with ethyl acetate (6×10 mL). Finally, the solvent was dried (Na$_2$SO$_4$) and concentrated. The crude product was purified by flash column chromatography (methanol:ethyl acteate, 1:1) to afford compound 16 (45 mg, 63%).

$^1$H NMR (300 MHz, CD$_3$OD, r.t., TMS): δ=1.43 (s, 9H), 2.98-3.13 (m, 2H, H-6+H-8a), 3.18 (m, 1H, H-7), 3.22-3.44 (m, 2H, H-3, H-5), 3.62-3.80 (m, 2H, H-4, H-8b), 4.23 (t, 1H, J=6.8 Hz), 4.32-4.48 (m, 3H), 7.28-7.87 (m, 8H). $^{13}$C NMR (100 MHz, CDCl$_3$, r.t.): δ=28.88, 43.42, 48.54, 56.37, 67.78, 72.04, 73.14, 79.03, 80.38, 80.76, 82.97, 120.94-128.78 (aromatic carbons), 142.61-145.43 (aromatic carbons), 157.71, 159.12, 169.46. MS (ES, [M−H]$^−$); Anal. Calcd for C$_{28}$H$_{33}$N$_2$O$_{10}$: 557.21, Found: 557.09. HRMS (ES, [M−H]$^−$); Anal. Calcd for C$_{28}$H$_{33}$N$_2$O$_{10}$: 557.2135, Found: 581.2133.

Example 10

Synthesis of Compound 17 of Example 1

To the mixture of Fmoc-Trp(Boc)-OH (205 mg, 0.39 mmol) and benzylamine (165 μL, 1.51 mmol) in DMF (5 mL) was added TBTU (249 mg, 0.77 mmol) and N,N-diisopropylethylamine (340 μL, 1.95 mmol). The reaction was stirred for 2 hours at room temperature. The solvent was removed in vacuo and the residue was purified by flash column silica gel chromatography (2:1, hexane:ethyl acetate) to yield the Fmoc-Trp(Boc)-NHBn (151 mg, 63%). The solution of Fmoc-Trp(Boc)-NHBn (151 mg, 0.25 mmol) and piperidine (0.5 mL) in DMF (2 mL) was stirred for 1 hour at room temperature. The solvent was removed in vacuo and the crude product was purified by flash column silica gel chromatography (from ethyl acetate to 5% methanol in ethyl acetate) to afford the NH$_2$-Trp(Boc)-NHBn (81 mg, 80%). Compound 16 (23 mg, 0.04 mmol) was dissolved in DMF (2 mL) and NH$_2$-Trp(Boc)-NHBn (72 mg, 0.18 mmol), TBTU (33 mg, 0.10 mmol), and N,N-diisopropylethylamine (37 μL, 0.21 mmol). The mixture was stirred for 4 hours at room temperature before removing the solvent under reduced pressure. The crude product was purified by flash chromatography using ethyl acetate as eluent to afford 17 (24 mg, 63%).

$^1$H NMR (300 MHz, CDCl$_3$, r.t., TMS): δ=1.38 (s, 9H), 1.63 (s, 9H), 3.04-3.34 (m, 6H), 3.37-3.61 (m, 5H), 3.71-3.83 (m, 1H), 4.03-4.37 (m, 5H), 4.45 (dd, 1H, J=6.7 Hz, J=2.2 Hz), 4.75-4.85 (m, 1H), 5.45-5.56 (br., 1H, NH), 6.12-6.29 (br., 1H, NH), 6.29-6.46 (br., 1H, NH), 6.73-6.91 (m, 2H), 6.96-7.03 (br., 1H, NH), 7.08-8.18 (m, 16H). HRMS (ES, [M+Na]$^+$); Anal. Calcd for C$_{51}$H$_{59}$N$_5$NaO$_{12}$: 956.4052, Found: 956.4054.

Example 11

Spectroscopic Data for Compound 4 of Example 1

4: $^1$H NMR (300 MHz, CDCl$_3$, r.t., TMS): δ=0.20 (s, 9H, TMS), 3.46-3.54 (m, 1H, H-7), 3.64 (dd, H-6, J=9.2 Hz, J=9.6 Hz), 3.68-3.85 (m, 8H, OCH$_3$, H-8a, H-8b, H-3, H-4, H-5), 4.55 (d, 1H, J=12.2 Hz), 4.62 (d, 1H, J=12.2 Hz), 4.63-4.74 (m, 3H), 4.86 (d, 1H, J=10.9 Hz), 4.88 (d, 1H, J=10.9 Hz), 4.96 (d, 1H, J=11.4 Hz), 5.00 (d, 1H, J=11.4 Hz), 7.22-7.41 (m, 20H). $^{13}$C NMR (100 MHz, CDCl$_3$, r.t.): δ=−0.85 (TMS), 52.00 (OCH$_3$), 68.78, 71.74, 73.25, 74.62, 75.04, 75.61, 77.71, 78.66, 79.95, 80.22, 87.40, 127.25-128.49 (aromatic carbons), 138.21, 138.50, 138.51, 138.58, 172.43 (C-1). MS (ES, [M+Na]$^+$); Anal. Calcd for C$_{40}$H$_{48}$NaO$_8$Si: 707.30, Found: 707.42. Anal. Calcd for C$_{40}$H$_{48}$O$_8$Si: C, 70.15; H, 7.06. Found: C, 70.35; H, 7.24.

Example 12

Synthesis of Certain Spirocyclic Sugar-Proline Hybrids of the Present Invention (SProHs)

Figure 4:
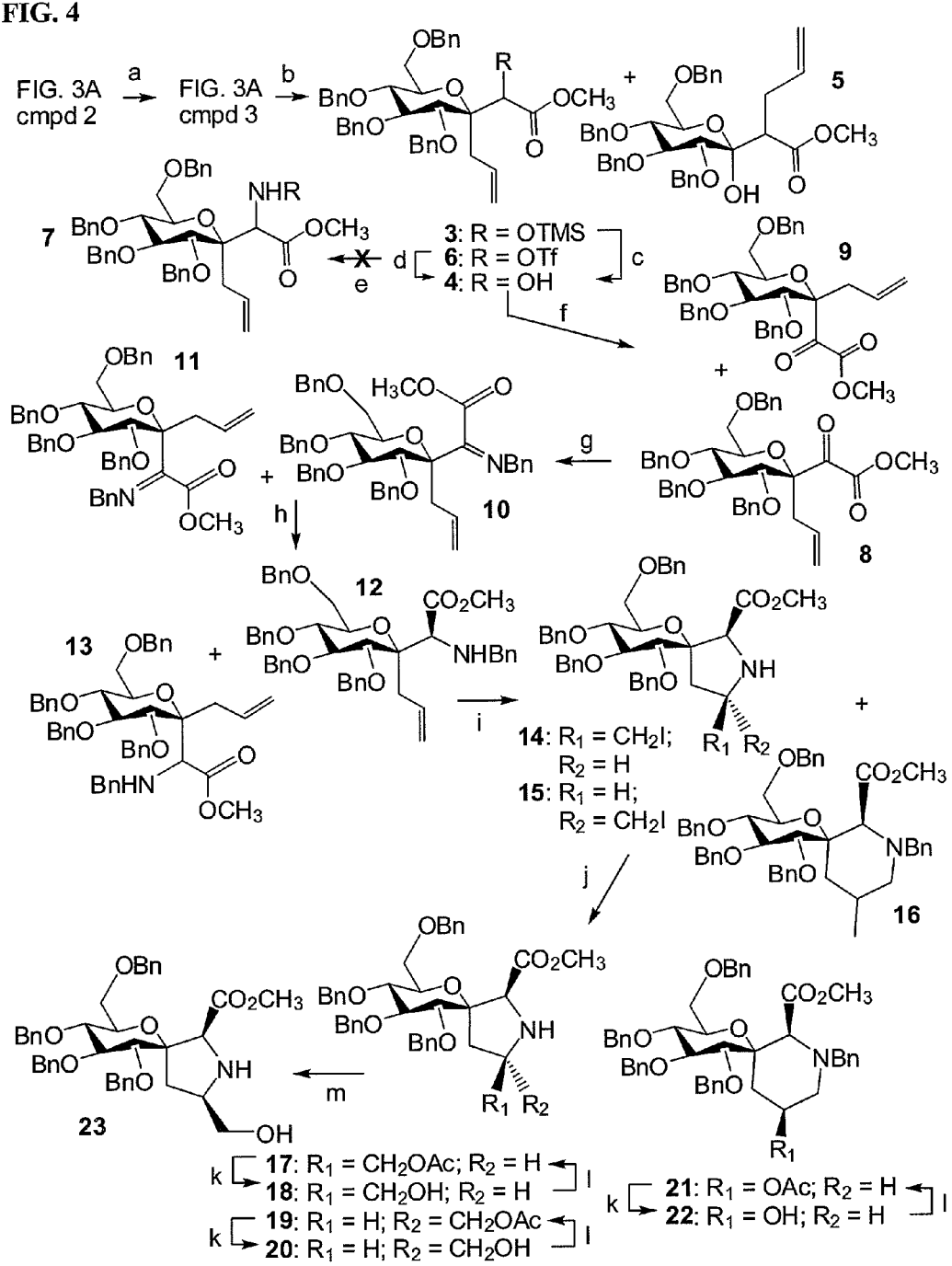
FIG. 4. A non-limiting method of generating a spirocyclic sugar-proline of the present invention. Reagents and conditions: a) $BrCH_2CO_2Me$, LHMDS, THF $-78°$ C., 2 h, 80%; b) $Bu_3SnCH_2CHCH_2$, TMSOTf, $CH_2Cl_2$, $0°$ C., 0.5 h, 70%; c) TFA (5 eq.), THF/$H_2O$ (5/1), r.t., overnight, quant.; d) $Tf_2O$, pyr., $0°$ C., 2 h, 92%; e) $NH_2R'$ (R'=Bn, p-methoxybenzyl, tert-butyl-carbamate), $CH_2ClCH_2Cl$, $50°$ C., 2d; f) DMSO, TFAA, $CH_2Cl_2$, TEA, $-78°$ C., 3 h, 80%; g) $NH_2Bn$, $TiCl_4$, ether $0°$ C. →r.t., 2×4 h, 96%; h) $NaCNBH_3$, AcOH, MeOH, $0°$ C., 3 h, quant.; i) $I_2$, $CH_2Cl_2$/$Et_2O$: 1/1, $0°$ C. →r.t., overnight; j) AgOAc, toluene, r.t., overnight; k) $K_2CO_3$, MeOH, r.t., 1 h, 95% (combined yield); l) pyr. $Ac_2O$, r.t., 1 h, quant.; m) $Pd(OH)_2$, $H_2$, HCl, MeOH, r.t., 6h, quant.

FIG. 4 depicts one method of generating a spirocyclic sugar-proline of the present invention, although variations of this method are possible, as known to those of skill in the art. Examples 12-18 describe the preparations of certain compounds of FIG. 4.

The synthesis started with the readily available D-gluco-based lactone 1 (FIG. 4) (PCC oxidation of commercially available 2,3,4,6-tetra-O-benzyl-D-glucopyranose (Toronto Chemicals) in dichloromethane provides 1 in 95% yield on a multi-gram scale; see: Gueyrard et al., 2005). Compound 1 reacts with the enolate of α-bromo acetic acid methylester generated from lithium bis-(trimethylsilyl)amide (LiN(SiMe$_3$)$_2$) in tetrahydrofuran (THF) at −78° C., to produce the exocyclic epoxide 2 in 80% yield as a single stereoisomer. Trimethylsilyltrifluoromethanesulfonate (TMSOTf)-promoted C-glycosylation of epoxide 2 with allyltributylstannane in dichloromethane at 0° C. afforded a mixture containing silylether 3 and alcohol 4 (ratio: 3:4=7:1) in a combined yield of 70%. Compounds 3 and 4 were obtained as a single diastereoisomer with uncharacterized stereochemistry at C-2. In addition, 20% of the acetal 5 was obtained as a diastereomeric mixture. The silylether 3 was hydrolyzed quantitatively into alcohol 4 by exposure to trifluoroacetic acid-containing wet THF. Compound 4 served as starting material for the installation of the amino function at C-2. Initially, the amino function was introduced by nucleophilic displacement of the triflate 6 prepared by reaction with trifluoromethanesulfonic anhydride in pyridine. However, exposure of the triflate to various nucleophiles including benzylamine, p-methoxybenzylamine and tert-butyl carbamate at low and elevated temperatures resulted only in trace amounts of the desired amine 7. To install the amino function, reductive amination was pursued. Initially, the alcohol 4 was oxidized to ketone 8 at −78° C. using a mixture containing trifluoroacetic anhydride, triethylamine and dimethylsulfoxide in dichloromethane to produce ketone 8 in 80% isolated yield. During this reaction, ketone 9 was observed as a side-product in 10% yield.

Subsequently, the ketones 8 and 9 were converted to the α-amino esters 12 and 13 in a two-step procedure. At first, compounds 8 and 9 were converted to the Schiff bases 10 and 11 using titaniumtetrachloride-promoted imination with benzylamine in ether to afford imines 10 and 11 in 96% and 90% yield, respectively, after chromatographic purification. Both imines were reduced to the corresponding amino esters 12 and 13 in quantitative yield using sodium cyanoborohydride in acetic acid-containing methanol. In both cases, the reduction of the imine produced a single stereoisomer. The absolute stereochemistry at C-2 of amino ester 12 was assigned at a later stage while the stereochemistry at C-2 in compound 13 has yet to be determined.

The pyrrolidine ring was installed by iodocyclization in dichloromethane to produce an inseparable isomeric mixture containing iodo-compounds 14, 15 and 16. To separate the compounds from each other, the compounds were converted into alcohols 18, 20 and 22 by a two-step process. At first, 14, 15 and 16 were exposed to silver acetate in toluene to produce an inseparable mixture of esters 17, 19 and 21 that by treatment with potassium carbonate in methanol afforded the alcohols 18, 20 and 22 in 44%, 45% and 6% yield, respectively, after column chromatography.

Example 13

Synthesis of Compound 2 of Example 12

Methyl bromoacetate (4.1 mmol) was dissolved in dry THF (20 ml) and cooled to −78° C. before lithium bis(trimethylsilyl)-amide (4 ml of a 1 M solution in THF) was slowly added. The reaction mixture was kept at −78° C. for an additional 30 minutes. Subsequently, a THF solution (5 ml) containing the lactone 1 (1 mmol) was added over a period of 10 minutes. After one hour, the temperature was raised to room temperature and stirred for 15 minutes before saturated aq. $NH_4Cl$ solution (20 ml) was added. The reaction mixture was evaporated under reduced pressure and the residue was dissolved in $CH_2Cl_2$ and partioned with water. The organic layer was dried over anhydrous $Na_2SO_4$, concentrated and purified by flash column chromatography (hexane/ethyl acetate:5/1) to get 2 as a solid (488 mg, 80%).

Example 14

Synthesis of Compound 4 of Example 12

To a mixture of epoxide 2 (480 mg, 0.79 mmol) and allyltributylstannane (0.995 ml, 3.15 mmol) in anhydrous $CH_2Cl_2$ (15 ml) was added dropwise trimethylsilyltrifluoromethanesulfonate (TMSOTf, 0.427 ml, 2.36 mmol) at 0° C. The mixture was stirred for 30 minutes at 0° C. before saturated sodium bicarbonate solution (10 ml) was added to quench the reaction. The organic layer was dried ($Na_2SO_4$), concentrated and purified by flash column chromatography using hexane/ethyl acetate 8/1→2/1 to get 3 (449 mg) and 4 (53 mg) as a syrup. The trimethylsilyl ether 3 was converted to 4 (368 mg, quant.) by exposure to TFA (0.196 ml, 5 equiv) in aqueous tetrahydrofuran (THF/$H_2O$: 5/1) overnight.

Example 15

Synthesis of Compound 8 of Example 12

To a solution of dry DMSO (133 μl, 1.88 mmol)) in anhydrous $CH_2Cl_2$ (12 ml) at −78° C. was added trifluoroacetic anhydride (200 μl, 1.41 mmol). After 10 min, a solution of compound 4 (307 mg, 0.47 mmol) dissolved in $CH_2Cl_2$ (8 ml) was added slowly and stirred for 40 min. at −78° C. Then triethylamine (394 μl, 2.82 mmol) was added dropwise and the reaction was kept at −78° C. for 2 hours. The cooling bath was removed and the reaction was quenched with $H_2O$ (10 ml). The organic layer was separated and the aqueous solution was extracted with $CH_2Cl_2$ (2×15 ml). The combined organic solution was dried with anhydrous $Na_2SO_4$, concentrated and purified by flash column chromatography (hexane/ethyl acetate:6/1) to give 8 (244 mg, 80%).

Example 16

Synthesis of Compound 10 of Example 12

To an ice-cooled solution of 8 (296 mg, 0.4 5 mmol) and benzylamine (148 μl, 1.36 mmol) in anhydrous diethyl ether (15 ml) was added dropwise $TiCl_4$ (0.544 ml of a 1 M solution in $CH_2Cl_2$, 0.54 mmol) at 0° C. After complete addition, the ice bath was removed and the reaction mixture was stirred for 4 h. Saturated sodium bicarbonate solution was added. The organic layer was separated and the water layer extracted with dichloromethane (2×15 ml). The combined organic layer was dried ($Na_2SO_4$), concentrated and purified by flash column chromatography (hexane/ethyl acetate:6/1) to provide a mixture of 8 (30%) and 10 (70%). Complete conversion of 8 to 10 was achieved by repetition of the previous imination procedure to provide 10 (323 mg, 96%).96%).

Example 17

Synthesis of Compound 12 of Example 12

To an ice-cooled solution of 10 (240 mg, 0.32 mmol) in methanol (9 ml) was added $NaCNBH_3$ (128 mg, 1.9 5 mmol), followed by 98% AcOH (39 μl, 0.65 mmol). The reaction mixture was stirred for 3 h at 0° C. and then quenched with water (5 ml) and extracted with $CH_2Cl_2$ (3×15 ml). The combined organic extracts were dried ($Na_2SO_4$), concentrated and purified by flash column chromatography (hexane/ethyl acetate:5/1) to afford 12 (239 mg, quant.).

Example 18

Synthesis of Compounds 17, 19 and 21 of Example 12

To a solution of 12 (340 mg, 0.46 mmol) in a 50% mixture of $CH_2Cl_2$ in diethyl ether (12 ml, 1:1) was added iodine (175 mg, 0.69 mmol) at 0° C. After 5 minutes, the ice bath was removed and the reaction was stirred for 12 h. The organic layer was washed with saturated sodium thiosulfate solution, water (2 ml) and dried ($Na_2SO_4$). The crude mixture (396 mg) was dissolved in toluene (15 ml), silver acetate (1.146 g, 6.88 mmol) was added and stirred for 12 hours. Subsequently, the suspension was filtered and the solution was concentrated under reduced pressure to provide an inseparable mixture of 17, 19 and 21 (323 mg). The mixture was dissolved in methanol (8 ml), $K_2CO_3$ (73 mg, 0.53 mmol) was added and stirred for 1 hour before quenching with saturated ammonium chloride solution (1 ml) and water (9 ml). The solvent was removed under reduced pressure and the dry residue was dissolved in $CH_2Cl_2$ (15 ml) and partioned with water (10 ml). The organic layer was concentrated, dried and purified by flash column chromatography (hexane/ethyl acetate: from 4/1 to 2/1) to yield 18 (135 mg, 44%), 20 (138 mg, 45%) and 22 (20 mg, 6.5%). Acetylation with a 1:1 mixture of pyridine:acetic anhydride afforded compounds 17, 19 and 21 in quantitative yield.

17: $^1$H NMR (500 MHz, $C_6D_6$, r. t. TMS): δ=1.76 (s, 3H), 2.20 (dd, H-9a, J=13.7 Hz, J=6.2 Hz), 2.38 (dd, H-9b, J=13.0 Hz, J=10.3 Hz), 3.00 (s, 3H), 3.34 (m, H-10), 3.56-3.70 (m, 5H, H-5, H-6, H-7, H-8a,b), 3.75 (s, H-2), 3.83-3.91 (m, H-4+1H, J=9.0 Hz, J=14.5 Hz), 4.12 (d, 1H, J=13.5 Hz), 4.28 (dd, H-11a, J=10.6 Hz, J=4.6 Hz), 4.44-4.53 (m, 2H+H-11b), 4.54-4.58 (d, 2H, J=11.0 Hz), 4.60 (d, 1H, J=11.2 Hz), 4.80 (d, 2H, J=11.2 Hz), 4.83 (d, 1H, J=11.2 Hz), 5.17 (d, 1H, J=12.4 Hz), 6.98-7.21 (m, 25H) $^{13}$C NMR (300 MHz, $CDCl_3$, r.t.): δ=20.95, 29.99, 51.54, 60.41, 60.84, 67.20, 69.39, 72.48, 72.77, 73.52, 75.05, 75.52, 76.04, 76.69, 78.66, 86.14, 87.48, 126.01-128.79 (aromatic carbons), 138.03, 138.04, 138.35, 138.91, 139.32, 170.99, 171.96. HRMS Calcd for $C_{49}H_{54}NO_9$ [M+H]$^+$:800.3793, found: 800.3794.

19: $^1$H NMR (500 MHz, $C_6D_6$, r. t. TMS): δ=1.68 (s, 3H), 2.14 (dd, H-9a, J=14.2 Hz, J=1.1 Hz), 2.82 (dd, H-9b, J=14.2 Hz, J=9.6 Hz), 3.07 (s, 3H), 3.57 (dd, H-6, J=9.4 Hz, J=9.3 Hz), 3.63 (dd, H-5, J=9.4 Hz, J=9.2 Hz), 3.65-3.72 (m, H-4, H-8a), 3.75 (dd, H-8b, J=11.1 Hz, J=1.6 Hz), 3.77-3.81 (m, H-7, H-10), 3.84 (d, 1H, J=14.4 Hz), 3.92 (s, H-2), 4.11 (d, 1H, J=14.2 Hz), 4.28 (dd, H-11a, J=10.7 Hz, J=7.8 Hz), 4.38 (dd, H-11b, J=10.7 Hz, J=5.4 Hz), 4.47 (d, 1H, J=12.5 Hz), 4.49-4.56 (m, 3H), 4.58 (d, 1H, J=12.4 Hz), 4.76 (d, 1H, J=11.2 Hz), 4.77 (d, 1H, J=11.1 Hz), 5.20 (d, 1H, J=12.4 Hz), 7.0-7.28 (m, 25H) $^{13}$C NMR (300 MHz, CDCl$_3$, r.t.): δ=20.99, 27.69, 51.14, 53.04, 59.97, 67.23, 69.04, 72.86, 73.04, 73.21, 73.71, 75.12, 75.63 (two carbons), 78.74, 85.88, 86.94, 126.03-128.49 (aromatic carbons), 137.00 (2 carbons), 138.50, 138.90, 139.47, 170.91, 170.93. HRMS Calcd for $C_{49}H_{54}NO_9$ [M+H]$^+$:800.3793, found: 800.3793.

21: $^1$H NMR (500 MHz, $C_6D_6$, r. t. TMS): δ=1.66 (s, 3H), 2.67 (dd, 1H, J=13.6 Hz, J=11.6 Hz), 2.81 (dd, J=13.6 Hz, J=4.1 Hz), 3.04 (s, 3H), 3.10 (dd, H-11a, J=10.2 Hz, J=5.6 Hz), 3.41 (d, H-4, J=9.1 Hz), 3.63 (s, H-2), 3.64-3.74 (m, H-11b, 2H(NBn), H-6), 3.79 (dd, H-8a, J=11.2 Hz, J=4.4 Hz), 3.84-3.91 (m, H-5, H-8b), 4.07 (m, H-7,), 4.38 (d, 1H, J=12.5 Hz), 4.44 (d, 1H, J=12.0 Hz), 4.59 (d, 1H, J=12.0 Hz), 4.63 (d, 1H, J=11.4 Hz), 4.69 (d, 1H, J=12.0 Hz), 4.76 (d, 1H, J=1.11 Hz), 4.77 (d, 1H, J=11.4 Hz), 5.14 (d, 1H, J=12.5 Hz), 5.49 (m, H-10), 6.99-7.16 (m, 25H) $^{13}$C NMR (300 MHz, $C_6D_6$, r.t.) δ=21.56, 26.39, 50.15, 50.44, 59.47, 69.73, 72.78, 73.44, 74.35 (2 carbons), 75.38 (2 carbons), 75.82, 78.74, 79.36, 80.95, 85.26, 126.50-128.90 (aromatic carbons), 138.78 (3 carbons), 139.24, 139.38, 170.71 (2 carbons). HRMS Calcd for $C_{49}H_{54}NO_9$ [M+H]$^+$:800.3793, found: 800.3791.

Example 19

Figure 5:
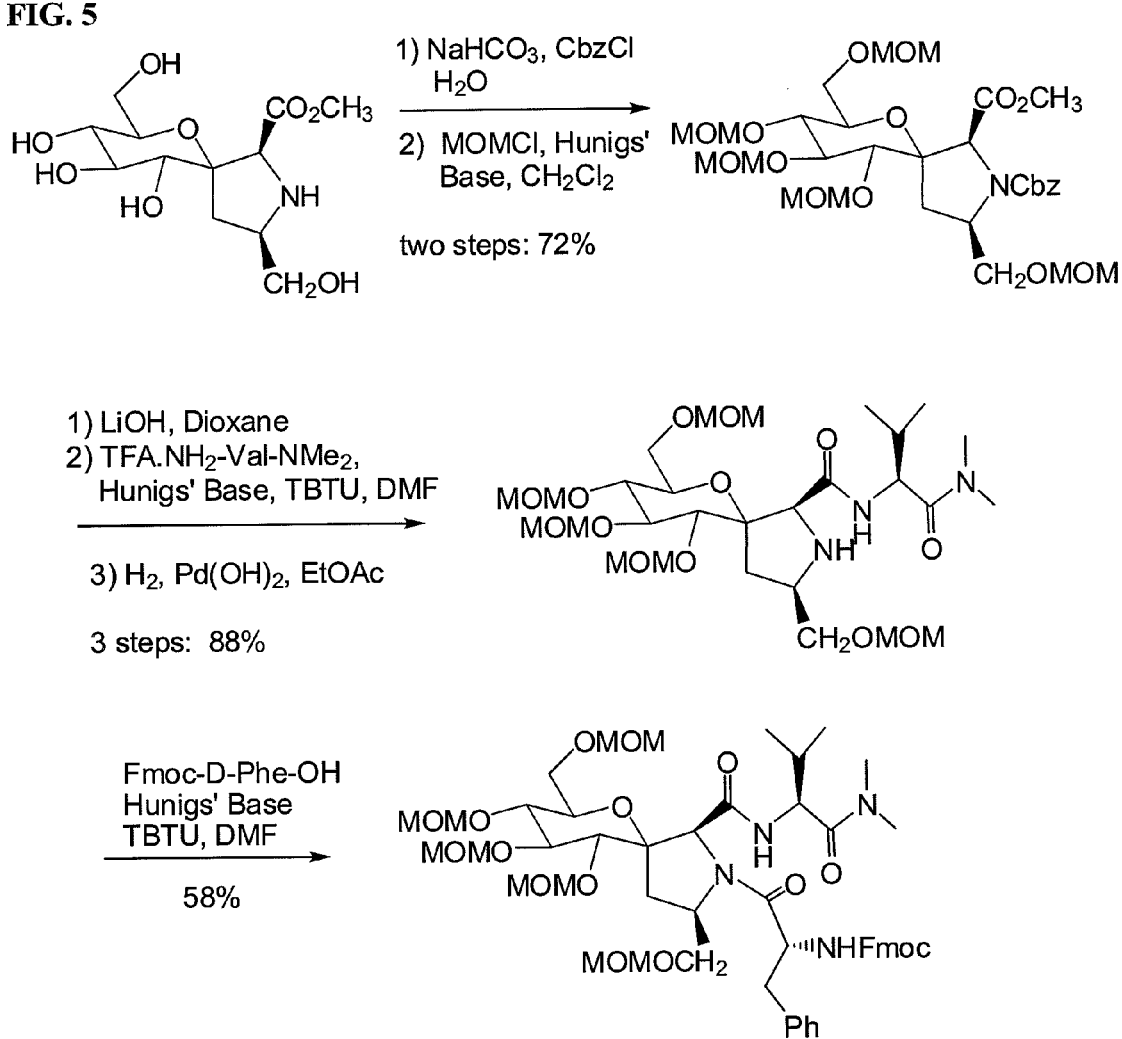
FIG. 5. A non-limiting method of generating a spirocyclic sugar-proline of the present invention.

Incorporation of a Spirocyclic Sugar-Proline of the Present Invention Into a Peptide FIG. 5 depicts one method of incorporating a spirocyclic sugar-proline of the present invention into a peptide, although variations of this method are possible, as known to those of skill in the art.

Synthesis of MOM-protected glucose-based proline analogue 2 (FIG. 5): To a mixture of sodium bicarbonate (55 mg, 0.6515 mmol) and compound 1 (40 mg, 0.1303 mmol) in water (1 ml) was added benzyl chloroformate (58 μl, 0.3909 mmol) and stirred for 6 hours at room temperature. The mixture was extracted with ethyl acetate (5×6 ml) and the combined organic layer was dried over anhydrous sodium sulfate and concentrated to afford the crude product, which was dissolved in a mixture of anhydrous N,N-diisopropylethylamine (2 ml) and dichloromethane (1 ml) and treated with chloromethyl methyl ether (395 μl, 5.212 mmol). The reaction was stirred for 24 hours under nitrogen at room temperature before the saturated NaHCO$_3$ solution (3 ml) was added. The mixture was extracted with ethyl acetate (3×6 ml) and the combined organic layer was dried with Na$_2$SO$_4$, concentrated and purified by flash column chromatography (hexanes/ethyl acetate: 1/2) to arrive at compound 2 (62 mg, 72%). $^1$H NMR (300 MHz, CDCl$_3$, r.t., TMS): δ=2.16 (m, 1H), 2.51 (m, 1H), 3.21-3.85 (m, 25H), 4.0-5.2 (m, 15H), 7.19-7.44 (m, 5H). $^{13}$C NMR (two isomers, 75 MHz, CDCl$_3$, r.t.): δ=31.62, 31.98, 52.20, 52.30, 55.06-56.64 (12 carbons), 66.71-85.37 (18 carbons), 96.44-98.17 (10 carbons), 127.33-128.48 (10 aromatic carbons), 136.24, 136.50, 154.45, 155.25, 169.92, 170.11. MS (ES, [M+Na]$^+$); $C_{30}H_{47}NNaO_{15}$ m/z calc. 684.28, found 684.36.

Synthesis of dipeptide NH-GlcPro-Val-NMe$_2$ 3: Compound 2 (40 mg, 0.0605 mmol) was treated with 2 N lithium hydroxide (0.3 ml, 0.605 mmol) in dioxane at 60° C. for 15 hours before the Amberlite IRC-50S ion-exchange resin (H$^+$) was added. The resin was removed through the filtration and the resulted acid was dissolved in DMF (1 ml) and treated with N,N-diisopropylethylamine (63 μl, 0.363 mmol), CF$_3$COOH.NH$_2$-Val-NMe$_2$ (47 mg, 0.181 mmol) and O-(Benzotriazol-1-yl)-N,N,N',N'-tetramethyluronium tetrafluoroborate (TBTU, 39 mg, 0.121 mmol). The mixture was stirred for 2 hours at room temperature and quenched with H$_2$O and extracted with ethyl acetate (3×6 ml). The combined organic layer was dried over anhydrous Na$_2$SO$_4$, concentrated and purified by flash column chromatography (ethyl acetate) to afford the Cbz-GlcPro-Val-NMe$_2$, which was dissolved in ethyl acetate (5 ml) and exposed to hydrogenation condition (10 psi H$_2$, catalytic Pd(OH)$_2$) for 1 hour to yield the dipeptide 3 (34 mg, 88%). $^1$H NMR (300 MHz, CD$_3$OD, r.t., TMS): δ=0.82-1.11 (m, 7H), 1.93-2.16 (m, 2H), 2.98 (s, 3H), 3.22 (s, 3H), 3.36-3.48 (m, 15H), 3.53-3.92 (m, 11H), 4.55-4.85 (m, 10H, partially overlap with solvent). $^{13}$C NMR (75 MHz, CD$_3$OD, r.t.): δ=18.75, 19.44, 19.56, 31.90, 36.12, 38.10, 38.17, 55.58–56.72 (5 carbons), 57.04, 68.47, 70.20, 70.79, 74.38, 77.43, 78.20, 83.19, 88.90, 97.68–99.98 (5 carbons) 171.75, 173.87 MS (ES, [M+H]$^+$); $C_{28}H_{54}N_3O_{13}$ m/z calc. 640.36, found 640.12.

Synthesis of tripeptide Fmoc-(D)-Phe-GlcPro-Val-NMe$_2$ 4: To a mixture of the compound 3 (30 mg, 0.0469 mmol), N,N-diisopropylethylamine (49 ul, 0.2814 mmol) and Fmoc-D-Phe-OH (73 mg, 0.1876 mmol) in DMF (1 ml) was added O-(Benzotriazol-1-yl)-N,N,N',N'-tetramethyluronium tetrafluoroborate (TBTU, 30 mg, 0.0938 mmol). The mixture was stirred for 6 hours at room temperature and quenched with saturated NaHCO$_3$ (3 ml) and extracted with ethyl acetate (4×6 ml). The combined organic layer was dried with sodium sulfate, concentrated and purified by flash column chromatography (ethyl acetate) to get tripeptide 4 (27 mg, 58%). $^1$H NMR (300 MHz, CDCl$_3$, r.t., TMS): δ=0.77-1.46 (m, 7H), 1.91-2.37 (m, 2H), 2.34-5.66 (m, 47H), 7.02-7.79 (m, 16H), MS (ES, [M+Na]$^+$); $C_{52}H_{72}N_4NaO_{16}$ m/z calc. 1031.48, found 1031.32.

Example 20

Synthesis of Certain Fused Bicyclic Sugar-Prolines of the Present Invention and Peptide Synthesis Incorporating Same Schemes 1-3 below depict non-limiting methods of generating certain fused bicyclic sugar-prolines of the present invention, although variations of these methods are possible, as known to those of skill in the art. Examples 20-35 describe the preparations of certain compounds of Schemes 1-3.

Scheme 1.
Synthesis of N-Boc-GlcPro-Carboxylic Acid 1

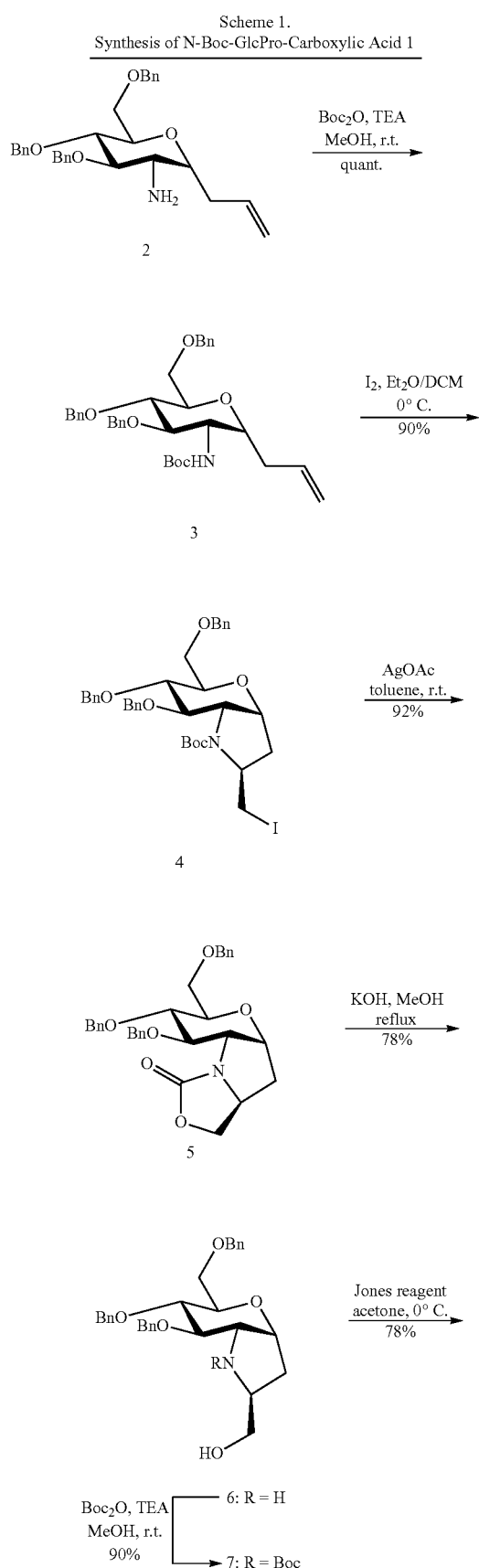

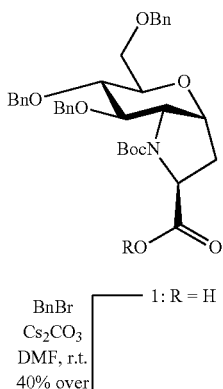

The synthesis of GlcProH 1 (Scheme 1) started from known amine 2 (Cipolla et al., 1997) which was synthesized in seven steps from commercially available 2,3,4,6 tetra-O-benzyl-D-glucopyranose in an overall yield of 40%. Protection of the amino function as tert-butyloxycarbamate (Boc) afforded 3 in quantitative yield. Installation of the pyrrolidine ring was achieved via amino-iodocyclization in 50% $CH_2Cl_2$/ether to afford the bicyclic iodo-derivative 4 in 90% yield as a single stereoisomer together with 5% unreacted 3. Attempts to substitute the iodo-function in 4 by hydroxide ion (KOH) or acetate failed, and produced complex mixtures containing tricyclic carbamate 5. However, high yields (92%) of 5 could be obtained by exposure of 4 to silver acetate in toluene (see Davies et al., 2004). Hydrolysis of 5 using potassium hydroxide in methanol at elevated temperature provided the amino alcohol 6 in 78% isolated yield. Protection of the amino function in 6 was accomplished using di-tert-butyl dicarbonate to yield the Boc-protected proline analogue 7 in 90% yield. Subsequently, the alcohol 7 was subjected to Jones oxidation to afford protected GlcProH 1 in 78% yield. To assign the stereochemistry of 1, esterification using benzyl bromide and cesium carbonate in DMF afforded the protected GlcProH 8 in 40% yield from 7.

Scheme 2.
Synthesis of N-Acetyl-GlcPro-N'-Methylamides 11-13

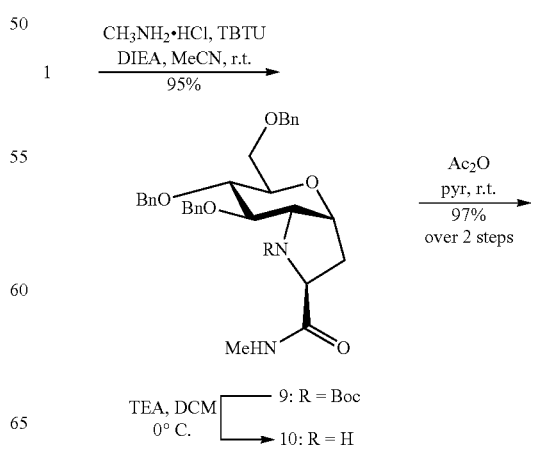

41
-continued

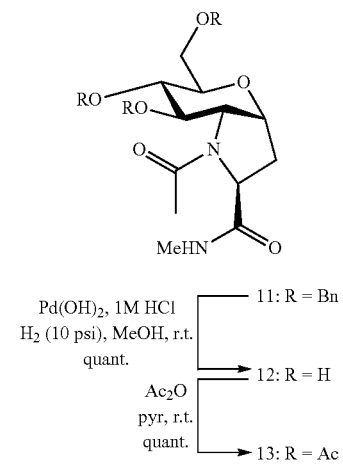

For each of 11-13, the ratio of trans/cis isomers was calculated by integrating as many well-resolved peaks as possible for each isomer, and taking the average of over all peaks for respective isomers (Taylor et al., 2003). The assignment of N-terminal amide geometry for both major and minor isomers of 11-16 was based on multiple GOESY experiments (Stronehouse et al., 1994). While it would be most desirable to study the GlcProHs in water, these results represent a proof of concept, and there is precedence for studying modifications of prolyl isomerization in non-aqueous environments (Petter, 1989; Trabocchi et al., 2004).

Scheme 3.
Synthesis of N-Acetyl-Glycyl-GlcPro-N'-Methylamides 14-16

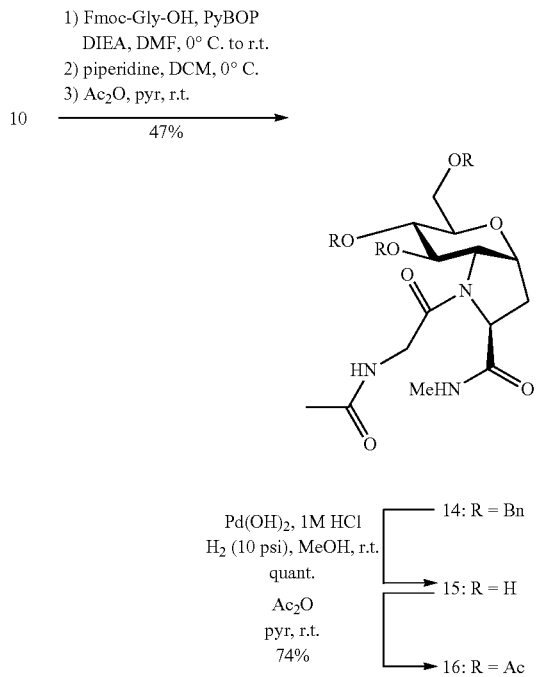

17: Ac-Pro-NHMe

42

Example 21

Synthesis of Compound 1 of Example 20

(2S,3aR,5R,6R,7S,7aS)-1-(tert-Butyloxycarbonyl)-6,7-di-O-benzyl-octahydro-5-(phenylmethyl hydroxymethyl)-pyrano[3,2-b]pyrrole-2-carboxylic acid (1): Compound 7 (0.125 g, 0.21 mmol) was dissolved in 6 mL acetone. The solution was cooled to 0° C. Fresh Jones' reagent (0.75 mL, 6.3 mmol) was prepared, and was added dropwise. The reaction mixture was stirred for 30 minutes, before adding water (5 mL), then aq. saturated sodium bicarbonate (5 mL). The acetone was removed under reduced pressure. The product was extracted into $CH_2Cl_2$ (3×15 mL) then dried ($Na_2SO_4$), concentrated under reduced pressure and was normally used directly in the next reaction. Purification by flash chromatography using 3:1 ethyl acetate/methanol yielded 1 as a clear oil (0.100 g, 0.17 mmol) (78.4%): $[\alpha]^{25}_D=-12.8°$ (c 0.4 $CH_3OH$); $^1H$ NMR (500 MHz, $CD_3OD$, 298K) δ=7.09-7.37 (m, 15H, aromatic), 4.38-4.76 (m, 7H, —$OCH_2Ph$, $H_4$), 4.25 (broad m, 1H, $H_2$, $H_2$ minor), 4.20 (dd apparent t, 0.8H, $H_7$, $J_{7,8}$=6.0 Hz, $J_{6,7}$=6.3 Hz), 4.10 (dd apparent, 1H, $H_8$, $J_{8,9}$=6.6 Hz), [4.06-4.10, m, 0.2H, $H_8$], [4.01, dd apparent t, 0.2H, $H_7$], 3.80-3.89 (m, 1H, $H_5$, $H_5$ minor), 3.71 (dd, 0.8H, $H_{10a}$, $J_{10a,10b}$=10.6 Hz, $J_{5,10a}$=6.0 Hz), [3.67-3.73, m, 0.2H, $H_{10a}$], 3.59 (dd, 0.8H, $H_{10b}$, $J_{5,10b}$=3.4 Hz), [3.57-3.62, m, 0.2H, $H_{10b}$], [3.55, dd apparent t, 0.2H, $H_6$], 3.46 (dd apparent t, 1H, $H_6$, $J_{5,6}$=6.4 Hz), 2.53 (ddd, 1H, $H_{3a}$, $J_{3a,3b}$=12.7 Hz, $H_{3a}$ minor), 1.90-1.97 (m, 1H, $H_{3b}$, $H_{3b}$ minor), 1.40 (s, 7.2H, tert-butyl), [1.32, s, 1.8H, tert-butyl]; $^{13}C$ NMR (75 MHz, $CD_3OD$, 298K) δ=168.7, 156.1, 139.8, 139.7, 139.5, (81.9), 81.5, (79.8), 78.4, (76.9), 76.6, 74.9, 74.7, (74.6), (74.5), 74.3, (74.2), 74.1, (73.9), 72.9, (70.4), 70.2, (59.9), 59.8, 33.9, (28.8), 28.6 ppm; HRMS (ES) calc. for $C_{35}H_{40}NO_8$ $(M-H)^-$: 602.2759. Found $(M-H)^-$: 602.2755.

Example 22

Synthesis of Compound 3 of Example 20

1-(2'-(tert-Butyloxycarbonyl)-amino-3',4',6'-tri-O-benzyl-2'-deoxy-α-D-glucopyranosyl)-2-propene (3): Compound 2 (0.202 g, 0.43 mmol) was dissolved in 4 mL methanol. Addition of triethylamine (0.6 mL, 4.3 mmol) was followed by addition of di-tert-butyl dicarbonate (0.46 g, 2.1 mmol). The reaction mixture was stirred for 16 hours. All reagents and solvent were removed under reduced pressure to provide 3 as a white solid (0.244 g, 0.43 mmol) (quant.): $[\alpha]^{25}_D=+11.4°$ (c 3.7 $CHCl_3$); mp 98-101° C.; $^1H$ NMR (300 MHz, $CDCl_3$, 298K) δ=7.20-7.40 (m, 15H, aromatic), 5.85 (dddd, 1H, —CH=$CH_2$, J=6.9 Hz, J=7.0 Hz, J=10.1 Hz, J=17.0 Hz), 5.61 (d, 1H, NHBoc, J=9.8 Hz), 5.02-5.17 (m, 2H, —CH=$CH_2$), 4.46-4.87 (m, 6H, —$OCH_2Ph$), 4.20 (dd, 1H, $H_5$, J=6.1 Hz, J=6.2 Hz), 3.95 (ddd, 1H, $H_1$, J=2.0 Hz, J=5.6 Hz, J=7.8 Hz), 3.80-3.89 (m, 2H, $H_2$, $H_{6a}$), 3.68-3.79 (m, 2H, $H_3$, $H_{6b}$), 3.55-3.60 (m, 1H, $H_4$), 2.17-2.39 (m, 2H, allylic), 1.45 (s, 9H, tert-butyl); $^{13}C$ NMR (75 MHz, $CDCl_3$, 298K) δ=155.8, 138.3, 137.8, 137.6, 134.6, 127.4–128.6 (aromatic carbons), 117.1, 79.1, 74.9, 74.9, 73.4, 73.2, 72.1, 71.8, 68.3, 68.0, 48.9, 35.5, 28.4 ppm; MS (ES) calc. for $C_{35}H_{43}NO_6$ $(M+Na)^+$: 596.30. Found $(M+Na)^+$: 596.30; Anal. Calcd for $C_{35}H_{43}NO_6$: 73.27 C, 7.55H, 2.44 N. Found: 73.43 C, 7.75H, 2.19 N.

Example 23

Synthesis of Compound 4 of Example 20

(2S,3aR,5R,6R,7S,7aS)-1-(tert-Butyloxycarbonyl)-6,7-di-O-benzyl-octahydro-5-(phenylmethyl hydroxymethyl)- pyrano[3,2-b]pyrrole-2-(iodomethyl) (4): Compound 3 (0.29 g, 0.51 mmol) was dissolved in 10 mL 1:1 $CH_2Cl_2$/diethyl ether. The solution was cooled to 0° C. before addition of iodine (0.39 g, 1.5 mmol). After 1 hour, the reaction mixture was warmed to ambient temperature before being worked-up by the addition of 20 mL saturated aq. sodium thiosulphate. With shaking, the solution became colorless. The product was extracted into $CH_2Cl_2$ (3×20 mL), dried ($Na_2SO_4$), concentrated and purified by flash chromatography using 5:1 hexanes/ethyl acetate. The product 4 was isolated as a single stereoisomer as a pale yellow oil (0.32 g, 0.46 mmol) (89.6%): $[\alpha]^{25}{}_D = -23.9°$ (c 2.5 $CHCl_3$); $^1$H NMR (300 MHz, $CDCl_3$, 298K) δ=7.13-7.40 (m, 15H, aromatic), 4.32-4.78 (broad m, 8H), 3.64-4.08 (broad m's, 5H), 3.55 (broad m, 1H), 3.45 (broad t, 2H), 2.40 (broad m, 1H, $H_{3a}$), 1.9 (m, 1H, $H_{3b}$), 1.5 (s, 9H, tert-butyl); $^{13}$C NMR (75 MHz, $CDCl_3$, 298K) δ=153.8, 138.8, 138.6, 138.4, 127.4-128.7 (aromatic carbons), 80.7, 77.6, 74.2, 74.0, 73.7, 73.5, 72.5, 70.2, 69.4, 59.5, 56.8, 36.5, 28.8, 14.8 ppm; MS (ES) calc. for $C_{35}H_{43}INO_6$ $(M+H)^+$: 700.21. Found $(M+H)^+$: 700.08. Calc. for $C_{35}H_{42}INNaO_6$ $(M+Na)^+$: 722.20. Found $(M+Na)^+$: 722.01; Anal. Calcd for $C_{35}H_{42}INO_6$: 60.09 C, 6.05H, 2.00 N. Found: 60.02 C, 5.74H, 2.39 N.

Example 24

Synthesis of Compound 5 of Example 20

(2S,3aR,5R,6R,7S,7aS)-1-(tert-butyloxycarbonyl)-6,7-di-O-benzyl-octahydro-5-(phenylmethyl hydroxymethyl)-pyrano[3,2-b]pyrrolo[1,2-c]-oxazol-3-one (5): Compound 4 (0.28 g, 0.41 mmol) was dissolved in 6 mL toluene. Addition of silver acetate (0.68 g, 4.1 mmol) made the solution instantly become colorless. The reaction was stirred for 16 hours at ambient temperature. The reaction mixture was diluted with 10 mL ethyl acetate then was filtered through celite. The product was concentrated under reduced pressure then purified using flash chromatography using 1:1 hexanes/ethyl acetate to yield 5 as a white solid (0.19 g, 0.37 mmol) (92.1%): $[\alpha]^{25}{}_D = +21.9°$ (c 2.0 $CHCl_3$); mp 106-111° C.; $^1$H NMR (300 MHz, $CDCl_3$, 298K) δ=7.14-7.48 (m, 15H, aromatic), 4.95 (d, 1H, —OCH$_2$Ph, J=11.1 Hz), 4.88 (d, 1H, —OCH$_2$Ph, J=11.4 Hz), 4.75 (d, 1H, —OCH$_2$Ph, J=11.4 Hz), 4.68 (ddd, 1H, $H_9$, $J_{3a,9}$=1.0 Hz, $J_{3b,9}$=5.7 Hz, $J_{8,9}$=5.7 Hz), 4.42-4.53 (m, 3H, —OCH$_2$Ph, $H_{11a}$), 4.38 (d, 1H, —OCH$_2$Ph, J=12.2 Hz), 4.08-4.20 (m, 2H, $H_{11b}$, $H_2$), 3.95 (dd, 1H, $H_8$, $J_{7,8}$=6.3 Hz), 3.72-3.82 (m, 1H, $H_5$), 3.64-3.72 (m, 2H, $H_6$, $H_7$), 3.53-3.59 (dd, 1H, $H_{10a}$, $J_{10b,10a}$=10.6 Hz, $J_{5,10a}$=4.7 Hz), 3.47-3.53 (dd, 1H, $H_{10b}$, $J_{5,10b}$=2.8 Hz), 2.10 (ddd, 1H, $H_{3a}$, $J_{2,3a}$=5.3 Hz, $J_{3a,3b}$=13.2 Hz), 1.59 (ddd, 1H, $H_{3b}$, $J_{2,3b}$=10.6 Hz); $^{13}$C NMR (75 MHz, $CDCl_3$, 298K) δ=161.1, 138.4, 138.1, 138.0, 127.6-128.4 (aromatic carbons), 80.7, 76.9, 75.4, 74.7, 74.4, 73.5, 73.2, 69.5, 66.8, 65.7, 57.5, 38.1 ppm; MS (ES) calc. for $C_{31}H_{33}NNaO_6$ $(M+Na)^+$: 538.22. Found $(M+Na)^+$: 538.22; Anal. Calcd for $C_{31}H_{33}NO_6$: 72.21 C, 6.45H. 2.72 N. Found: 72.17 C, 6.69H. 2.57 N.

Example 25

Synthesis of Compound 6 of Example 20

(2S,3aR,5R,6R,7S,7aS)-6,7-di-O-Benzyl-octahydro-5-(phenylmethyl hydroxymethyl)-pyrano[3,2-b]pyrrole-2-hydroxymethyl (6): Compound 5 (0.18 g, 0.35 mmol) was dissolved in 8 mL methanol. After addition of potassium hydroxide (1.5 g, 26.2 mmol) the solution was heated to reflux for 4 hours. The reaction mixture was then cooled to 0° C. followed by acidification by addition of 5 mL 3 M aq. HCl. The methanol was removed under reduced pressure. The reaction mixture was brought to pH 9 by addition of 20 mL aq. saturated sodium bicarbonate. The product was extracted into $CH_2Cl_2$ (4×10 mL) then dried ($Na_2SO_4$), concentrated under reduced pressure and purified by flash chromatography using first 1:1 hexanes/ethyl acetate then 5:1 ethyl acetate/methanol to yield 6 as a pale yellow solid (0.15 g, 0.27 mmol) (78.4%): $[\alpha]^{25}{}_D = +38.9°$ (c 2.8 $CHCl_3$); mp 91-94° C.; $^1$H NMR (300 MHz, $CDCl_3$, 298K) δ=7.15-7.42 (m, 15H, aromatic), 4.45-4.65 (m, 6H, —OCH$_2$Ph), 4.25-4.35 (m, 1H, $H_9$), 4.05-4.11 (m, 1H, $H_5$), 3.82 (dd, 1H, $H_{10a}$, $J_{10a,10b}$=10.2 Hz, $J_{5,10a}$=6.7 Hz), 3.77 (dd apparent t, 1H, $H_7$, $J_{7,8}$=4.5 Hz, $J_{6,7}$=4.4 Hz), 3.61 (dd, 1H, $H_{10b}$, $J_{5,10b}$=5.1 Hz), 3.56 (dd apparent t, 1H, $H_6$, $J_{5,6}$=4.2 Hz), 3.41-3.51 (m, 2H, $H_{11a}$, $H_2$), 3.29 (broad s, 0.3H, NH), 3.25 (dd, 1H, $H_{11b}$, $J_{11a,11b}$=12.1 Hz, $J_{11b,2}$=7.3 Hz), 3.09 (dd, 1H, $H_8$, $J_{8,9}$=3.7 Hz), 2.0 (ddd, 1H, $H_{3a}$, J=2.1 Hz, J=8.0 Hz, $J_{3a,3b}$=14.0 Hz), 1.59-1.69 (m, 1H, $H_{3b}$, J=6.0 Hz, J=7.0 Hz); $^{13}$C NMR (75 MHz, $CDCl_3$, 298K) δ=138.1, 137.8, 137.5, 127.7-128.6 (aromatic carbons), 74.4, 73.9, 73.4, 73.3, 72.8, 72.7, 71.8, 67.7, 64.1, 60.2, 57.4, 33.9 ppm; MS (ES) calc. for $C_{30}H_{36}NO_5$ $(M+H)^+$: 490.26. Found $(M+H)^+$: 490.39. Calc. for $C_{30}H_{35}NNaO_5$ $(M+Na)^+$: 512.24. Found $(M+Na)^+$: 512.36; Anal. Calcd for $C_{30}H_{35}NO_5$: 73.59 C, 7.21H, 2.86 N. Found: 73.23 C, 7.52H, 2.86 N.

Example 26

Synthesis of Compound 7 of Example 20

(2S,3aR,5R,6R,7S,7aS)-1-(tert-Butyloxycarbonyl)-6,7-di-O-benzyl-octahydro-5-(phenylmethyl hydroxymethyl)-pyrano[3,2-b]pyrrole-2-hydroxymethyl (7): Compound 6 (0.048 g, 0.098 mmol) was dissolved in 4 mL methanol. Addition of triethylamine (0.68 mL, 4.9 mmol) was followed by addition of di-tert-butyl dicarbonate (0.11 g, 0.49 mmol). The reaction mixture was stirred for 16 hours. All reagents and solvent were removed under reduced pressure to provide 7 as a colorless oil (0.052 g, 0.088 mmol) (89.7%): $[\alpha]^{25}{}_D = -10.4°$ (c 2.0 $CHCl_3$); $^1$H NMR (300 MHz, $CDCl_3$, 313K) δ=7.14-7.41 (m, 15H, aromatic), 4.36-4.90 (m, 8H, —OCH$_2$Ph, $H_2$, $H_{11a}$), 3.95-4.14 (m, 3H, $H_{11b}$, $H_9$, $H_7$), 3.85-3.95 (m, 1H, $H_8$), 3.52-3.88 (m, 4H, $H_5$, $H_6$, $H_{10a}$, $H_{10b}$), 2.31 (broad s, 1H, $H_{3a}$), 1.75 (broad singlet, 1H, $H_{3b}$), 1.45 (s, 9H, tert-butyl); $^{13}$C NMR (75 MHz, $CDCl_3$, 298K) δ=155.8, 138.4, 138.0, 137.9, 126.9-128.7 (aromatic carbons), 80.9, 75.2, 73.4, 73.2, 72.7, 68.9, 66.8, 60.2, 59.8, 32.1, 29.7, 28.4, 22.7, 14.2 ppm; MS (ES) calc. for $C_{35}H_{44}NO_7$ $(M+H)^+$: 590.31. Found $(M+H)^+$: 590.30; Anal. Calcd for $C_{35}H_{43}NO_7$: 71.28 C, 7.35H, 2.38 N. Found: 71.03 C, 7.59H, 2.33 N.

Example 27

Synthesis of Compound 8 of Example 20

(2S,3aR,5R,6R,7S,7aS)-1-(tert-Butyloxycarbonyl)-6,7-di-O-benzyl-octahydro-5-(phenylmethyl hydroxymethyl)-pyrano[3,2-b]pyrrole-2-carboxylic acid benzyl ester (8): Compound 7 (0.018 g, 0.029 mmol) was dissolved in 3 mL DMF. Addition of cesium carbonate (0.015 g, 0.045 mmol) was followed by addition of benzyl bromide (0.011 mL, 0.089 mmol). The reaction mixture was stirred for 1 hour, and then the solvent was removed under reduced pressure. The reaction mixture was diluted with 10 mL water followed by extraction into $CH_2Cl_2$ (3×10 mL), dried over anhydrous $Na_2SO_4$, and concentrated under reduced pressure before being purified by flash chromatography using 4:1 hexanes/ ethyl acetate to yield 8 as a colorless oil (0.11 g, 0.18 mmol) (83.6%): $[\alpha]^{25}{}_D=-14.2°$ (c 0.4 CHCl$_3$); $^1$H NMR (300 MHz, CDCl$_3$, 298K) δ=7.05-7.41 (m, 20H, aromatic), 5.19 (d, 1H, —OCH$_2$Ph, J=12.1 Hz), 5.11 (d, 1H, —OCH$_2$Ph, J=12.3 Hz), 4.35-4.80 (m, 8H, —OCH$_2$Ph, H$_2$, H$_9$), 4.28 (dd apparent t, 1H, H$_7$, $J_{7,8}$=5.6 Hz, $J_{6,7}$=5.7 Hz), 4.17 (dd apparent t, 1H, H$_8$, $J_{8,9}$=5.8 Hz), 3.83-3.93 (m, 1H, H$_5$), 3.70 (dd, 1H, H$_{10a}$, $J_{10a,10b}$=10.4 Hz, $J_{5,10a}$=6.3 Hz), 3.57 (dd, 1H, H$_{10b}$, $J_{5,10b}$=3.4 Hz), 3.48 (dd apparent t, 1H, H$_6$, $J_{5,6}$=5.8 Hz), 2.40-2.55 (m, 1H, H$_{3a}$), 1.80-2.00 (m, 1H, H$_{3b}$), 1.38 (s, 9H, tert-butyl); $^{13}$C NMR (75 MHz, CDCl$_3$, 298K) δ=172.9, 153.6, 138.4, 138.1, 138.1, 135.3, 127.0-128.7 (aromatic carbons), 80.4, 76.0, 74.8, 73.6, 73.5, 73.4, 72.8, 71.2, 69.0, 66.8, 58.8, 58.2, 33.0, 28.1 ppm; MS (ES) calc. for C$_{42}$H$_{47}$NNaO$_8$ (M+Na)$^+$: 716.32. Found (M+Na)$^+$: 716.11; Anal. Calcd for C$_{42}$H$_{47}$NNaO$_8$: 70.37 C, 6.61H, 1.95 N. Found: 70.44 C, 6.71H, 1.88 N.

Example 28

Synthesis of Compound 9 of Example 20

(2S,3aR,5R,6R,7S,7aS)-1-(tert-Butyloxycarbonyl)-6,7-di-O-benzyl-octahydro-5-(phenylmethyl hydroxymethyl)-pyrano[3,2-b]pyrrole-2-carboxamide N'-methylamide (9): Compound 1 (0.10 g, 0.16 mmol) was dissolved in 6 mL acetonitrile. Addition of diisopropylethylamine (0.11 mL, 0.64 mmol) was followed by addition of TBTU (0.10 g, 0.32 mmol) and methylamine hydrochloride (0.02 g, 0.32 mmol). The reaction mixture was stirred at ambient temperature for 4 hours. The reaction mixture was diluted with 15 mL water followed by extraction into CH$_2$Cl$_2$ (3×15 mL), dried (Na$_2$SO$_4$), then concentrated under reduced pressure and purified by flash chromatography using 3:1 ethyl acetate/ hexanes to provide 9 as a clear oil (0.086 g, 0.14 mmol) (84.3%): $[\alpha]^{25}{}_D=-3.5°$ (c 0.4 CHCl$_3$); $^1$H NMR (300 MHz, acetone-D$_6$, 298K) δ=7.15-7.45 (m, 15H, aromatic), 4.45-4.82 (m, 8H, —OCH$_2$Ph, H$_2$, H$_9$), 4.39 (dd apparent t, 1H, H$_7$, $J_{7,8}$=5.3 Hz, $J_{6,7}$=5.3 Hz), 4.28 (dd, 1H, H$_2$, J=5.9 Hz, J=7.9 Hz), 4.11 (dd apparent t, 1H, H$_8$, $J_{8,9}$=5.5 Hz), 3.86-3.95 (m, 1H, H$_5$), 3.78 (dd, 1H, H$_{10a}$, $J_{10a,10b}$=10.5 Hz, $J_{5,10a}$=6.1 Hz), 3.68 (dd, 1H, H$_{10b}$, $J_{5,10b}$=3.8 Hz), 3.55 (dd apparent t, 1H, H$_6$, $J_{5,6}$=5.7 Hz), 2.80 (d, 3H, —NHCH$_3$), 2.42 (ddd, 1H, H$_{3a}$, J=6.3 Hz, J=8.1 Hz, J=13.4 Hz), 1.89 (ddd, 1H, H$_{3b}$, J=5.8 Hz, J=6.2 Hz, J=12.0 Hz), 1.37 (s, 9H, tert-butyl); $^{13}$C NMR (75 MHz, acetone-D$_6$, 298K) δ=173.8, 154.4, 139.7, 139.5 (2), 128.1–129.0 (aromatic carbons), 79.4, 76.5, 75.9, 74.0, 73.4 (2), 72.9, 71.5, 69.9, 60.8, 59.3, 34.6, 28.2, 25.9 ppm; MS (ES) calc. for C$_{36}$H$_{44}$N$_2$NaO$_7$ (M+Na)$^+$: 639.30. Found (M+Na)$^+$: 639.27; Anal. Calcd for C$_{36}$H$_{44}$N$_2$O$_7$: 70.11 C, 7.19H. 4.54 N. Found: 70.19 C, 7.43H. 4.47 N.

Example 29

Synthesis of Compound 10 of Example 20

(2S,3aR,5R,6R,7S,7aS)-6,7-di-O-Benzyl-octahydro-5-(phenylmethyl hydroxymethyl)-pyrano[3,2-b]pyrrole-2-carboxamide N'-methylamide (10): Compound 9 (0.035 g, 0.057 mmol) was dissolved in 1.5 mL CH$_2$Cl$_2$. The reaction mixture was then cooled to 0° C. Trifluoroacetic acid (0.5 mL, 6.73 mmol) was added slowly. After 1 hour the solution was co-distilled with toluene (2×5 mL), and was normally used directly in the next reaction. Purification by flash chromatography using 10:1 ethyl acetate/methanol provided 10 as a clear oil (0.027 g, 0.14 mmol) (93.1%): $[\alpha]^{25}{}_D=-11.2°$ (c 1.0 CHCl$_3$); $^1$H NMR (500 MHz, CDCl$_3$, 298K) δ=7.58 (broad q, 1H, —NHCH$_3$), 7.20-7.38 (m, 15H, aromatic), 4.47-4.62 (m, 6H, —OCH$_2$Ph), 4.18-4.27 (m, 1H, H$_2$), 4.04-4.14 (m, 1H, H$_5$), 3.78-3.91 (m, 2H, H$_9$, H$_{10a}$), 3.73 (broad dd, 1H, H$_7$, $J_{7,8}$=3.9 Hz, $J_{6,7}$=3.8 Hz), 3.65 (dd, H$_{10b}$, $J_{10a,10b}$=10.2 Hz, $J_{5,10b}$=5.6 Hz), 3.59 (broad dd, 1H, H$_6$, $J_{5,6}$=3.8 Hz), 2.89 (broad dd, 1H, —NH, J=3.0 Hz, J=3.3 Hz), 2.78 (d, 3H, —NHCH$_3$, J=5.0 Hz), 2.36 (ddd, 1H, H$_{3a}$, J=1.96 Hz, 9.6 Hz, 14.4 Hz), 1.95 (ddd, 1H, H$_{3b}$, J=5.0 Hz, 7.0 Hz, 14.4 Hz); $^{13}$C NMR (75 MHz, CDCl$_3$, 298K) δ=175.3, 138.1, 137.8, 137.6, 127.6-128.6 (aromatic carbons), 74.2, 73.5, 73.3, 72.8, 72.6, 72.4, 71.6, 67.6, 60.9, 58.8, 36.7, 25.7 ppm; MS (ES) calc. for C$_{31}$H$_{37}$N$_2$O$_5$ (M+H)$^+$: 517.27. Found (M+H)$^+$: 517.30; Anal. Calcd for C$_{31}$H$_{36}$N$_2$O$_5$: 72.07 C, 7.02H, 5.42 N. Found: 72.11 C, 7.13H, 5.36 N.

Example 30

Synthesis of Compound 11 of Example 20

(2S,3aR,5R,6R,7S,7aS)-1-Acetyloctahydro-6,7-di-O-benzyl-5-(phenylmethyl hydroxymethyl)-pyrano[3,2-b]pyrrole-2-carboxamide N'-methylamide (11): Compound 10 (0.029 g, 0.056 mmol) was dissolved in 2 ml pyridine followed by addition of acetic anhydride (0.053 mL, 0.56 mmol). The reaction mixture was stirred for 15 hours, then the solvent and reagents were removed under reduced pressure and the product was purified by flash chromatography using 10:1 ethyl acetate/methanol to provide 11 as a white solid (0.030 g, 0.054 mmol) (97% over 2 steps): $[\alpha]^{25}{}_D=+49.6°$(c 1.0 CHCl$_3$); decomposed at 142-147° C.; $^1$H NMR (500 MHz, CDCl$_3$, 298K, 0.036M) δ=7.23-7.41 (m, 13H, aromatic), 7.11-7.20 (m, 2H, aromatic), 5.97 (broad q, 1H, —NHCH$_3$), 4.98 (ddd, 1H, H$_9$, $J_{3a,9}$=11.7 Hz, $J_{3b,9}$=7.3 Hz, $J_{8,9}$=7.4 Hz), 4.93 (d, 1H, —OCH$_2$Ph, J=11.2 Hz), 4.80 (d, 1H, —OCH$_2$Ph, J=10.8 Hz), 4.52-4.64 (m, 4H, —OCH$_2$Ph), 4.25 (dd apparent d, 1H, H$_2$, $J_{2,3a}$=9.5 Hz, $J_{2,3b}$=0.8 Hz), 4.03 (dd, 1H, H$_8$, $J_{7,8}$=9.2 Hz), 3.63-3.78 (m, 4H, H$_5$, H$_6$, H$_{10a}$, H$_{10b}$), 3.57 (dd apparent t, 1H, H$_7$, $J_{6,7}$=9.0 Hz), 2.82 (d, 3H, —NHCH$_3$, J=4.2 Hz), 2.35 (ddd, 1H, H$_{3a}$, $J_{3a,3b}$=12.3 Hz), 2.15 (s, 3H, —COCH$_3$), 2.05 (ddd, 1H, H$_{3b}$); $^{13}$C NMR (75 MHz, CDCl$_3$, 298K) (major conformer) δ=172.1, 171.6, 137.8, 137.7, 137.5, 127.8-128.5 (aromatic carbons), 83.0, 78.0, 75.9, 74.9, 73.7, 73.6, 73.3, 68.8, 60.1, 57.8, 28.4, 26.4, 22.9 ppm; HRMS (ES) calc. for C$_{33}$H$_{39}$N$_2$O$_6$ (M+H)$^+$: 559.2802. Found (M+H)$^+$: 559.2801.

Example 31

Synthesis of Compound 12 of Example 20

(2S,3aR,5R,6R,7S,7aS)-1-Acetyloctahydro-6,7-dihydroxy-5-(hydroxymethyl)-pyrano[3,2-b]pyrrole-2-carboxamide N'-methylamide (12): Compound 11 (0.027 g, 0.048 mmol) was dissolved in 10 mL methanol. Addition of Pearlman's catalyst (20% palladium hydroxide on carbon) (0.030 g, approx. 0.028 mmol) was followed by addition of 1M aq. HCl (0.072 mL, 0.072 mmol). The reaction mixture was stirred vigorously under hydrogen atmosphere (10 psi) for 4.5 hours, after which it was flushed with nitrogen and filtered. The product was then concentrated under reduced pressure to provide 12 as a clear oil (0.014 g, 0.048 mmol) (quant.): [α]$^{25}_D$=+20.5° (c 1.0 CHCl$_3$); $^1$H NMR (500 MHz, D$_2$O, 298K, 0.035M) δ=4.55-4.64 (m, 0.85H, H$_9$), 4.32 (dd apparent d, 0.85H, H$_2$, J$_{2,3a}$=10.2 Hz, J$_{2,3b}$=1.3 Hz), [4.11, dd, 0.15H, H$_8$, J$_{8,9}$=7.7 Hz, J$_{7,8}$=8.0 Hz], 3.99 (dd, 0.85H, H$_8$, J$_{8,9}$=7.2 Hz, J$_{7,8}$=9.2 Hz), 3.70 (dd, 0.85H, H$_{10a}$, J$_{5,10a}$=2.2 Hz, J$_{10a,10b}$=12.4 Hz), [3.67-3.72, m, 0.15H, H$_{10a}$], 3.62 (dd, 0.85H, H$_{10b}$, J$_{5,10b}$=5.0 Hz), [3.60, dd, 0.15H, H$_{10b}$, J=1.7 Hz, J=12.5 Hz], 3.51-3.56 (m, 0.85H, H$_5$), 3.51 (dd apparent t, 0.85H, H$_7$, J$_{6,7}$=9.9 Hz, H$_7$ minor), [3.45-3.50, m, H$_5$], [3.35, dd, 0.15H, H$_6$, J$_{5,6}$=9.9 Hz], 3.32 (dd apparent t, 0.85H, H$_6$, J$_{5,6}$=9.7 Hz), [2.63, s, 0.45H, —COCH$_3$], 2.58 (s, 2.55H, —COCH$_3$), 2.55 (ddd, 0.85H, H$_{3a}$, J$_{3a,9}$=11.7 Hz, J$_{3b,3a}$=13.5 Hz, H$_{3a}$ minor), 2.10 (s, 2.55H, —NHCH$_3$), [1.93, ddd, 0.15H, H$_{3b}$, J$_{2,3b}$=1.8 Hz, J$_{3b,9}$=6.7 Hz, J$_{3a,3b}$=12.9 Hz], [1.83, s, 0.45H, —COCH$_3$], 1.79 (ddd, 0.85H, H$_{3b}$, J$_{3b,9}$=7.8 Hz, H$_{3b}$ minor); $^{13}$C NMR (75 MHz, D$_2$O, 298K) (major conformer) δ=174.6, 174.4, 74.5, 73.8, 73.3, 68.6, 61.5, 61.0, 58.1, 28.3, 26.1, 22.3 ppm; HRMS (ES) calc. for C$_{12}$H$_{20}$N$_2$O$_6$Na (M+Na)$^+$: 311.1212. Found (M+Na)$^+$: 311.1214.

Example 32

Synthesis of Compound 13 of Example 20

(2S,3aR,5R,6R,7S,7aS)-1-Acetyloctahydro-6,7-O-acetyl-5-(hydroxymethyl-O-acetyl)-pyrano[3,2-b]pyrrole-2-carboxamide N'-methylamide (13): Compound 12 (0.014 g, 0.048 mmol) was dissolved in 1 mL pyridine. Acetic anhydride (0.046 mL, 0.48 mmol) was added and the reaction mixture was stirred at ambient temperature for 15 hours. All solvent and reagent were removed under reduced pressure providing compound 13 as a clear oil (0.020 g, 0.048 mmol) (quant.): [α]$^{25}_D$=+53.3°(c 0.3 CHCl$_3$); $^1$H NMR (500 MHz, CDCl$_3$, 298K, 0.036 M) δ=6.37 (broad q, 0.87H, —NHCH$_3$), [5.97, broad q, 0.13H, —NHCH$_3$], [5.25, dd, 0.13H, H$_7$], 5.22 (dd apparent t, 0.87H, H$_7$, J$_{7,8}$=9.8 Hz, J$_{6,7}$=10.0 Hz), 5.10 (ddd, 0.87H, H$_9$, J$_{3a,9}$=11.8 Hz, J$_{3b,9}$=7.1 Hz, J$_{8,9}$=7.3 Hz), [5.03, dd, 0.13H, H$_6$, J$_{6,7}$=9.5 Hz, J$_{5,6}$=9.2 Hz], 4.99 (dd apparent t, 0.87H, H$_6$, J$_{5,6}$=9.9 Hz), [4.70, ddd, 0.13H, H$_9$, J$_{3a,9}$=11.6 Hz, J$_{3b,9}$=6.8 Hz, J$_{8,9}$=7.0 Hz], [4.54, dd, 0.13H, H$_8$, J$_{7,8}$=7.8 Hz], [4.41, dd, 0.13H, H$_2$, J$_{2,3a}$=9.4 Hz, J$_{2,3b}$=1.5 Hz], 4.27-4.35 (m, 1.87H, H$_2$, H$_{10a}$, H$_{10a}$ minor), 4.19 (dd, 0.87H, H$_8$), 4.08 (dd, 1H, H$_{10b}$, J$_{5,10b}$=2.4 Hz, J$_{10a,10b}$=12.5 Hz, H$_{10b}$ minor), 3.98 (ddd, 0.87H, H$_5$, J$_{5,10a}$=4.3 Hz), [3.89, ddd, 0.13H, H$_5$, J$_{5,10b}$=2.6 Hz, J$_{5,10a}$=4.9 Hz], [2.84, d, 0.39H, —NHCH$_3$, J=4.8 Hz], 2.81 (d, 2.61H, —NHCH$_3$, J=4.8 Hz), [2.73, ddd, 0.13H, H$_{3a}$, J$_{3a,3b}$=12.8 Hz], 2.48 (ddd, 0.87H, H$_{3a}$, J$_{2,3a}$=9.8 Hz, J$_{3a,3b}$=12.3 Hz), 2.13 (s, 2.61H, —COCH$_3$), 2.09, (s, 3H, —COCH$_3$, —COCH$_3$ minor), 2.06 (s, 2.61H, —COCH$_3$), [2.04, s, 0.39H, —COCH$_3$], [2.03, s, 0.39H, —COCH$_3$], [2.02, s, 0.39H, —COCH$_3$], 2.00-2.05 (m, 0.87H, H$_{3b}$), 2.01 (s, 2.61H, —COCH$_3$), [1.86, s, 0.39H, —COCH$_3$]; $^{13}$C NMR (75 MHz, CDCl$_3$, 298K) (major conformer) δ=171.8, 170.7, 170.3, 169.9, 169.5, 73.9, 73.8, 69.7, 68.0, 62.2, 58.6, 58.1, 28.2, 26.4, 22.0, 20.9, 20.7, 20.6 ppm; HRMS (ES) calc. for C$_{18}$H$_{27}$N$_2$O$_9$ (M+H)$^+$: 415.1711. Found (M+H)$^+$: 415.1711.

Example 33

Synthesis of Compound 14 of Example 20

N-Acetyl-glycyl-(2S,3aR,5R,6R,7S,7aS)-6,7-di-O-benzyl-octahydro-5-(phenylmethyl hydroxymethyl)-pyrano[3,2-b]pyrrole-2-carboxamide N'-methylamide (14): Compound 10 (0.105 g, 0.203 mmol) was dissolved in 6 mL N,N dimethylformamide and cooled to 0° C. The reaction was stirred under inert atmosphere. Diisopropylethylamine (0.212 mL, 1.218 mmol) and PyBOP (0.317 g, 0.609 mmol) were added and the solution was stirred for 10 min. Fmoc-Gly-OH (0.181 g, 0.609 mmol) was added and the reaction mixture was stirred for a further 5 min. before being allowed to warm to ambient temperature where it stirred for 18 hours. The red solution was diluted with ethyl acetate, washed with 1 M HCl (10 mL), then brine (10 mL), dried and evaporated giving a red oil. The product was purified by flash chromatography using ethyl acetate, giving a white solid product (0.0 85 g) (53%), along with unreacted starting material (0.025 g) (24%). The coupled product was dissolved in 4 mL dichloromethane, cooled to 0° C., and treated with piperidine (1 mL). The reaction mixture was stirred for 1 hour before the solvent and reagents were removed under reduced pressure, leaving a white solid. The intermediate was dissolved in 4 mL pyridine followed by addition of acetic anhydride (0.5 mL). The reaction mixture was stirred for 15 hours, then the solvent and reagents were removed under reduced pressure and the product was purified by flash chromatography using 10:1 ethyl acetate/methanol to provide 14 as a clear oil (0.059 g, 0.096 mmol) (47.1%) (over 3 steps): [α]$^{25}_D$=+23.5° (c 1.0 CHCl$_3$); $^1$H NMR (500 MHz, CDCl$_3$, 298K, 0.033 M) δ=7.10-7.38 (m, 15H, aromatic), 6.30 (t, 1H, —NH$_{(Gly)}$, —NH$_{(Gly)}$ minor), 6.22 (q, 1H, —NHCH$_3$, —NHCH$_3$ minor), 4.95 (d, 0.95H, —OCH$_2$Ph, J=11.3 Hz), 4.83 (ddd, 0.95H, H$_9$, J$_{3b,9}$=7.6 Hz, J$_{3a,9}$=12.0 Hz, J$_{8,9}$=7.2 Hz), 4.75 (d, 0.95H, —OCH$_2$Ph, J=10.8 Hz), 4.51-4.64 (m, 4.15H, —OCH$_2$Ph, —OCH$_2$Ph minor, H$_9$ minor), [4.22, dd, 0.05H, H$_8$, J$_{8,9}$=6.5 Hz, J$_{7,8}$=8.2 Hz], 4.17 (dd apparent d, 0.95H, H$_2$, J$_{2,3b}$=1.0 Hz, J$_{2,3a}$=9.7 Hz), 4.05-4.13 (m, 1.9H, H$_8$, H$_{α1(Gly)}$, H$_2$ minor), 4.02 (dd, 0.95H, H$_{α2(Gly)}$, J$_{Hα2(Gly),NH}$=4.1 Hz, J$_{Hα1(Gly),Hα2(Gly)}$=17.1 Hz), 3.68-3.76 (m, 2H, H$_7$, H$_{10a}$, H$_7$ minor, H$_{10a}$ minor), 3.61-3.67 (m, 2.1H, H$_5$, H$_{10b}$, H$_5$ minor, H$_{10b}$ minor, H$_{α2(Gly)}$ minor, H$_{α1(Gly)}$ minor), 3.53 (dd apparent t, 0.95H, H$_6$, J$_{6,7}$=9.7 Hz, J$_{5,6}$=9.4 Hz), [3.52-3.58, m, 0.05H, H$_6$], [2.80, d, 0.15H, —NHCH$_3$, J=5.0 Hz], 2.74 (d, 2.85H, —NHCH$_3$, J=5.0 Hz), 2.36 (ddd, 1H, H$_{3a}$, J$_{3a,3b}$=12.5 Hz, H$_{3a}$ minor), 1.99 (ddd, 1H, H$_{3b}$, H$_{3b}$ minor), 1.92 (s, 3H, —COCH$_3$, —COCH$_3$ minor); $^{13}$C NMR (75 MHz, CDCl$_3$, 298K) δ=171.5, 170.5, 169.5, 137.8, 137.6, 137.3, 127.7–128.8 (aromatic carbons), 81.8, 78.2, 75.7, 74.8, 73.8, 73.7, 73.4, 68.7, 59.0, 58.4, 42.9, 28.6, 26.4, 22.7 ppm; HRMS (ES) calc. for C$_{35}$H$_{41}$N$_3$O$_7$Na (M+Na)$^+$: 638.2837. Found (M+Na)$^+$: 638.2841.

Example 34

Synthesis of Compound 15 of Example 20

N-Acetyl-glycyl-(2S,3aR,5R,6R,7S,7aS)-6,7-dihydroxy-5-(hydroxymethyl)-octahydro-pyrano[3,2-b]pyrrole-2-carboxamide N'-methylamide (15): Compound 14 (0.020 g, 0.032 mmol) was dissolved in 5 mL methanol. Addition of Pearlman's catalyst (20% palladium hydroxide on carbon) (0.020 g, approx. 0.019 mmol) was followed by addition of 1 M aq. HCl (0.010 mL, 0.010 mmol). The reaction mixture was stirred vigorously under hydrogen atmosphere (10 psi) for 4.5 hours, after which it was flushed with nitrogen and filtered. The product was then concentrated under reduced pressure to provide 15 as a yellow oil (0.012 g, 0.035 mmol) (quant.): $[\alpha]^{25}_D = -2.5°$ (c 0.6 CHCl$_3$); $^1$H NMR (500 MHz, D$_2$O, 298K, 0.035M) δ=4.57-4.66 (m, 0.9H, H$_9$), 4.47 (d, 0.9H, H$_{\alpha1(Gly)}$, $J_{H\alpha1(Gly),H\alpha2(Gly)}$=17.2 Hz), 4.35 (dd apparent d, 1H, H$_2$, $J_{2,3a}$=10.3 Hz, $J_{2,3b}$=1.0 Hz, H$_2$ minor), [4.14, dd apparent t, 0.1H, H$_8$, $J_{8,9}$=7.2 Hz, $J_{7,8}$=7.7 Hz], 4.01 (dd, 0.9H, H$_8$, $J_{8,9}$=7.2 Hz, $J_{7,8}$=9.0 Hz), 3.97 (d, 0.9H, H$_{\alpha2(Gly)}$), [3.87, d, 0.1H, H$_{\alpha1(Gly)}$, $J_{H\alpha1(Gly),H\alpha2(Gly)}$=17.1 Hz], 3.70 (dd, 1H, H$_{10a}$, $J_{5,10a}$=2.3 Hz, $J_{10a,10b}$=12.2 Hz, H$_{10a}$ minor), 3.62 (dd, 1H, H$_{10b}$, $J_{5,10b}$=5.0 Hz, H$_{10b}$ minor), [3.45-3.51, m, 0.1H, H$_5$], 3.50-3.58 (m, 1.9H, H$_5$, H$_7$, H$_7$ minor), [3.36, dd, 0.1H, H$_6$], 3.32 (dd apparent t, 0.9H, H$_6$, $J_{6,7}$=9.9 Hz, $J_{5,6}$=9.5 Hz), [2.64, s, 0.3H, —NHCH$_3$], 2.58 (s, 2.7H, —NHCH$_3$), 2.54 (ddd, 1H, H$_{3a}$, $J_{3b,9}$=11.2 Hz, $J_{3a,3b}$=12.7 Hz, H$_{3a}$ minor), 1.90 (s, 2.7H, —COCH$_3$), 1.79 (ddd, 1H, H$_{3b}$, $J_{3b,9}$=7.7 Hz, H$_{3a}$ minor); $^{13}$C NMR (75 MHz, D$_2$O, 298K) δ=175.0, 174.4, 171.3, 74.5, 73.8, 73.5, 68.8, 61.1, 60.4, 58.6, 42.4, 27.9, 26.2, 22.0 ppm; HRMS (ES) calc. for C$_{14}$H$_{23}$N$_3$O$_7$Na (M+Na)$^+$: 368.1428. Found (M+Na)$^+$: 368.1427.

Example 35

Synthesis of Compound 16 of Example 20

N-Acetyl-glycyl-(2S,3aR,5R,6R,7S,7aS)-6,7-di-O-acetyl-5-(hydroxymethyl-O-acetyl)-octahydro-pyrano[3,2-b]pyrrole-2-carboxamide N'-methylamide (16): Compound 15 (0.012 g, 0.035 mmol) was dissolved in 1 mL pyridine. Acetic anhydride (0.034 mL, 0.35 mmol) was added and the reaction mixture was stirred at ambient temperature for 15 hours. All solvent and reagent were removed under reduced pressure and the product was purified by flash chromatography using 10:1 ethyl acetate/methanol to provide 16 as a clear oil (0.014 g, 0.030 mmol) (74%): $[\alpha]^{25}_D$=+37.3°(c 0.3 CHCl$_3$); $^1$H NMR (500 MHz, CDCl$_3$, 298K, 0.03 M) δ=6.56 [broad q, 0.2H, —NHCH$_3$, J=4.6 Hz], [6.39, broad dd, 0.2H, —NH$_{(Gly)}$], 6.31 (dd, 0.8H, —NH$_{(Gly)}$), 6.16 (q, 0.8H, —NHCH$_3$, J=4.6 Hz), [5.27, dd, 0.2H, H$_7$, $J_{7,8}$=8.3, $J_{6,7}$=9.1 Hz], 5.19 (dd apparent t, 0.8H, H$_7$, $J_{7,8}$=9.4 Hz, $J_{6,7}$=9.9 Hz), 5.03 (ddd, 0.8H, H$_9$, $J_{3a,9}$=11.8 Hz, $J_{3b,9}$=7.5 Hz, $J_{8,9}$=7.2 Hz), [5.00-5.05, m, 0.2H, H$_6$], 4.99 (dd apparent t, 0.8H, H$_6$, $J_{5,6}$=9.8 Hz), [4.84, ddd, 0.2H, H$_9$, $J_{3a,9}$=10.9 Hz, $J_{3b,9}$=6.7 Hz, $J_{8,9}$=7.3 Hz], [4.52, dd apparent t, 0.2H, H$_8$, J=7.7 Hz], 4.44 (dd, 1H, H$_{\alpha1(Gly)}$, $J_{H\alpha1(Gly),NH}$=6.3 Hz, $J_{H\alpha1(Gly),H\alpha2(Gly)}$=17.4 Hz, H$_2$ minor), 4.26-4.35 (m, 1.8H, H$_2$, H$_{10a}$, H$_{10a}$ minor), 4.23 (dd, 0.8H, H$_8$), 4.08 (dd, 1H, H$_{10b}$, $J_{5,10b}$=2.3 Hz, $J_{10a,10b}$=12.2 Hz, H$_{10b}$ minor), 3.97 (ddd, 0.8H, H$_5$, $J_{5,10a}$=4.2 Hz), [3.86-3.92, m, 0.4H$_5$, H$_{\alpha1(Gly)}$], 3.86 (dd, 0.8H, H$_{\alpha2(Gly)}$, $J_{H\alpha2(Gly),NH}$=3.1 Hz), [3.56, dd, 0.2H, H$_{\alpha2(Gly)}$, $J_{H\alpha2(Gly),NH}$=3.5 Hz, $J_{H\alpha1(Gly),H\alpha2(Gly)}$=16.9 Hz], [2.83, d, 0.6H, —NHCH$_3$, J=4.6 Hz], 2.80 (d, 2.4H, —NHCH$_3$, J=4.6 Hz), [2.68, m, 0.2H, H$_{3a}$, $J_{2,3a}$=9.5 Hz, $J_{3a,3b}$=12.6 Hz], 2.55 (ddd, 0.8H, H$_{3a}$, $J_{2,3a}$=10.0 Hz, $J_{3a,3b}$=12.5 Hz), 2.13 (s, 2.4H, —COCH$_3$), 2.09 (s, 3H, —COCH$_3$), 1.98-2.04 (m, 1H, H$_{3b}$, H$_{3b}$ minor), [2.02, s, 0.6H, —COCH$_3$], 2.01 (s, 3H, —COCH$_3$, —COCH$_3$ minor), 1.99 (s, 3H, —COCH$_3$, —COCH$_3$ minor); $^{13}$C NMR (75 MHz, CDCl$_3$, 298K) δ=(major conformer) 171.4, 170.7, 170.4, 170.4, 169.4, 168.8, 73.6, 73.4, 69.8, 68.1, 62.1, 58.6, 57.1, 41.9, 28.1, 26.5, 22.9, 20.9, 20.7, 20.5 ppm; HRMS (ES) calc. for C$_{20}$H$_{29}$N$_3$O$_{10}$Na (M+Na)$^+$: 494.1745. Found (M+Na)$^+$: 494.1743.

Example 36

Conformational Studies of Certain Fused Bicyclic Sugar-Prolines of the Present Invention Experiments were undertaken to determine the Kt/c effect of certain fused bicyclic sugar-proline-containing peptides. A very similar profile of Kt/c for the Ac-Gly-GlcPro-NHMe model compounds 14-16 compared to the Ac-GlcPro-NHMe model compounds 11-13 (Table 1) was observed. In CD$_3$OD, there was an increase in the cis-content as the sugar substituent changed from benzyl 14 (<3%), to hydroxyl 15 (15%), to acetate 16 (25%). These results confirm that the substituents on the sugar are influencing Kt/c.

TABLE 1

Trans/cis ratio[a] (Kt/c) and % cis isomer of 14-16 in various solvents.

| Compound | Solvent | | |
| --- | --- | --- | --- |
| | CDCl$_3$ | D$_2$O | CD$_3$OD |
| 14 (R = Bn) | 19 (5%) | n.s.[b] | >30 (<3%) |
| 15 (R = H) | n.s.[b] | 9 (10%) | 5.7 (15%) |
| 16 (R = Ac) | 4 (20%) | n.s.[b] | 3 (25%) |

[a]Determined by 500 MHz NMR at 25° C.
[b]not soluble

Analysis of the coupling constants of the pyranose ring showed it exists in a chair conformation. For example, for 12 in CD$_3$OD, $J_{5,6}$ was 9.4 Hz, while $J_{6,7}$ was 9.6 Hz and $J_{7,8}$ was 9.0 Hz (see below for numbering). The average values of each coupling constant in comparison to the literature values match best to a Cγ-endo conformation for the pyrrolidine ring (Table 2).

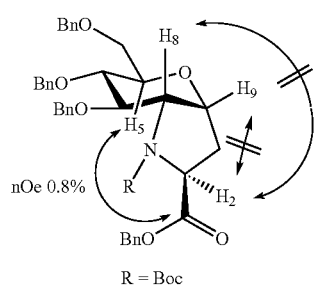

8

R = Boc

Conformationally relevant nOe interactions observed for 8.

TABLE 2

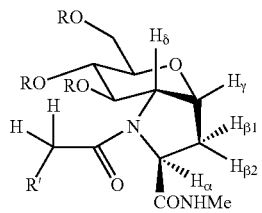

11-13 R = Bn, H, Ac; R' = H
14-16 R = Bn, H, Ac; R' = CH₃CONH

Comparison of Average Coupling Constants (Hz) for 11-16 Major and Minor isomers[a] with Cγ-endo and Cγ-exo puckers of 4-Fluoroproline and L-Proline.

| Compound | $^3J_{\alpha\beta1}$ | $^3J_{\alpha\beta2}$ | $^3J_{\gamma\beta1}$ | $^3J_{\gamma\beta2}$ | $^3J_{\delta\gamma1}$ |
|---|---|---|---|---|---|
| 11-16 Major isomers | 9.9 ± 0.3 | 1.0 ± 0.1 | 11.8 ± 0.3 | 7.4 ± 0.2 | 7.2 ± 0.1 |
| 11-16 Minor isomers | 9.3 ± 0.2 | 1.7 ± 0.3 | 10.9 ± 0.4 | 6.8 ± 0.2 | 7.1 ± 0.3 |
| 4(R)-Fluoroproline[34] (Cγ-endo) | 10 | 3 | 4 | 1 | 4 |
| 4(S)-Fluoroproline[34] (Cγ-exo) | 8 | 10 | 1 | 4 | 3 |
| L-Proline[35] (Cγ-endo) | 6-10 | 2-3 | 5-9 | 8-12 | 6-10 |
| L-Proline[35] (Cγ-exo) | 7-10 | 7-11 | 5-9 | 2-3 | 5-9 |

[a] ± standard error

Also, coupling constants indicate that the prolyl 4-position hydroxyl group (pyrano endocyclic oxygen) is oriented in an equatorial position relative to the pyrrolidine ring, which is not its preferred axial orientation (Jenkins et al., 2004; Bretscher et al., 2001). Perhaps most importantly, all coupling constant values changed very little as the sugar substituents were varied, even as the solvent was varied, and between the major and minor isomers in each case. Together, these results indicate that the rigid pyranose ring is restricting the conformational freedom of the pyrrolidine ring.

Example 37

Synthesis of Certain Sugar-Amino Acid Chimeras of the Present Invention and Peptide Synthesis Incorporating Same: Glycosidic-Lysine Chimera (GlcLysC)

Figure 6:
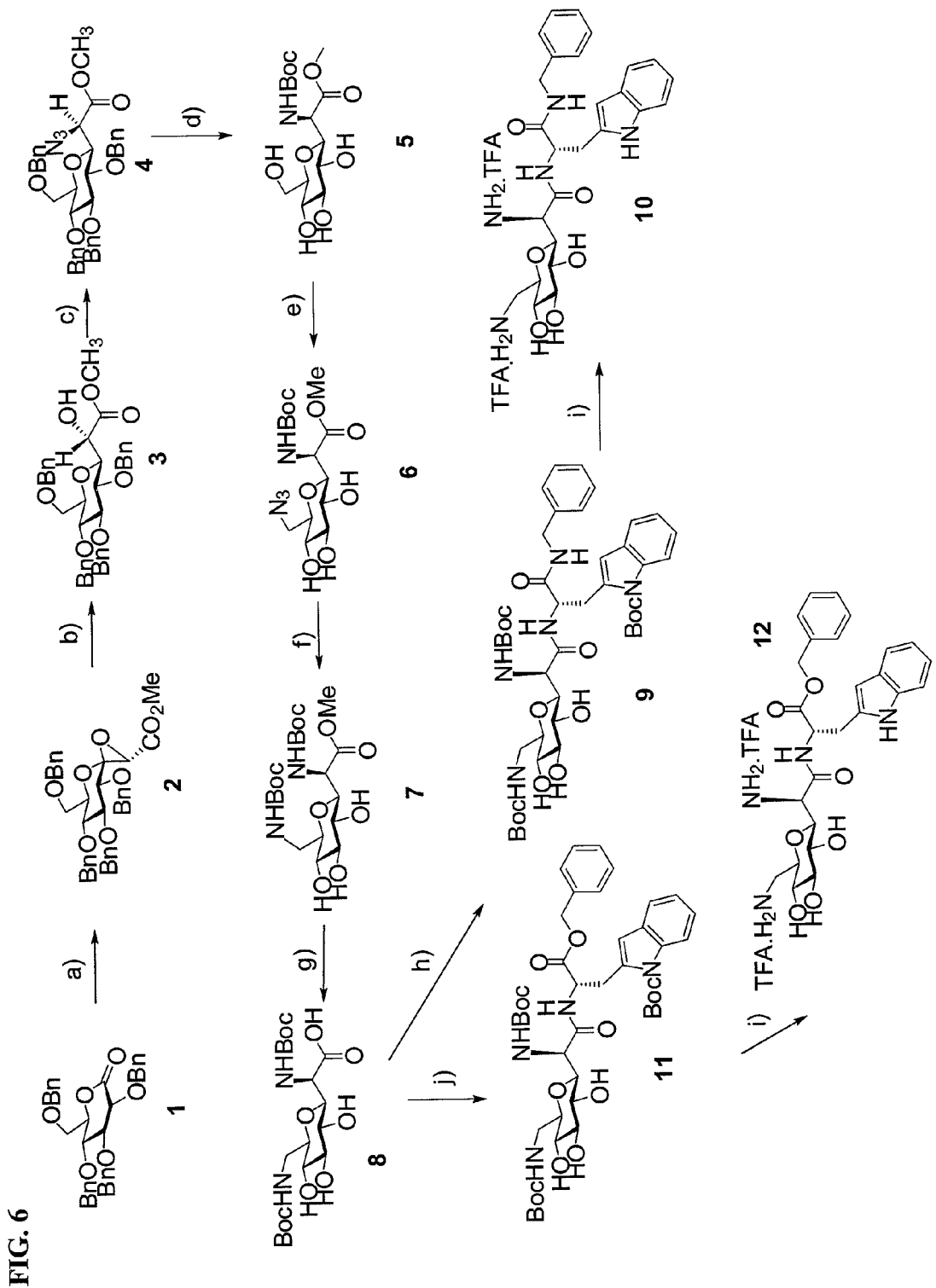
FIG. 6. A non-limiting method of generating a sugar-lysine chimera of the present invention. Reagents and conditions: (a) LiHMDS, $CH_2BrCOOMe$, THF, $-78°$ C.-r.t., 2 h, 80%; (b) $Bu_3SnH$, TMSOTf, $CH_2Cl_2$, $0°$ C., 30 min., 88%; (c) $Tf_2O$, pyridine, $CH_2Cl_2$, $0°$ C. 1 h, quant.; $NaN_3$, $CH_2Cl_2$, 15-crown-5, rt., 24 h, 81%; (d) $Pd(OH)_2$, MeOH, HCl (1.3 eq.), 6 h; then $Boc_2O$ (2.0 eq.), $Et_3N$ (4 eq.), 2 h, 90%; (e) TsCl (2.2 eq.), pyridine, rt, 2 h; $NaN_3$, DMF, $55°$ C., 12 h, 85%; (f) $Pd(OH)_2$, $H_2$, MeOH, 30 min. then $Boc_2O$ (2.0 eq.), $Et_3N$ (4 eq.), 2 h, rt, 78%; (g) LiOH (4 eq.), THF:$H_2O$ (2:1), 2 h, $0°$ C., 92%; (h) TBTU, H-Trp(Boc)-NHBn, DIEA, DMF, 80%; (i) TFA, $CH_2Cl_2$, $0°$ C., 1 h; (j) TBTU, H-Trp(Boc)-OBn, DIEA, DMF, 82%.
Figure 7:
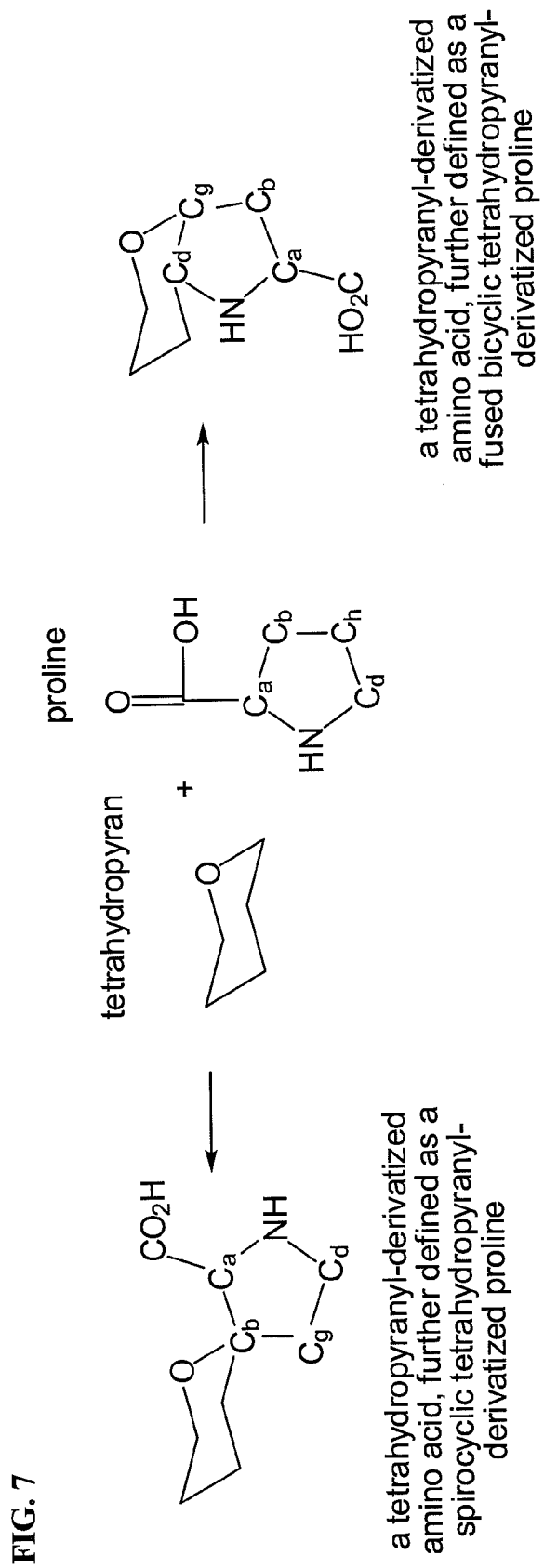
FIG. 7. Non-limiting example of a tetrahydropyranyl-derivatized amino acid (sugar-proline-lysine chimera). The tetrahydropyran may be further defined as a monosaccharide.

FIG. 6 depicts one method of generating a sugar-lysine chimera of the present invention, although variations of this method are possible, as known to those of skill in the art. The sugar-lysine chimera was then incorporated into the amphiphilic antimicrobial dipeptide sequence kW. Certain compounds of FIG. 6 are also described in Examples 1-11. Spectroscopic Data for Compounds 7-12 of FIG. 6:

7: $^1$H NMR (300 MHz, CD₃OD): δ 1.50 (br s, 18H), 3.02 (br t, 1H, J=7.2 Hz), 3.08 (br t, 1H, J=9.3 Hz), 3.24 (m, 1H), 3.36 (m, 1H), 3.50 (dd, 1H, J=1.6, 10.0 Hz), 3.56 (br d, 1H, J=9.0 Hz), 3.64 (m, 1H), 3.78 (s, 3H), 4.69 (br s, 1H); $^{13}$C NMR (75 MHz, CD₃OD): δ 28.86, 28.94, 43.03, 52.79, 55.55, 71.75, 72.90, 79.29, 80.35, 80.88, 80.96, 82.13, 158.13, 158.75, 172.03; MS (ES, [M+Na]⁺): m/z 473.24.

8: $^1$H NMR (300 MHz, CD₃OD): δ 1.44 (2 s, 18H), 1.62-1.84 (m, 2H), 2.96 (br t, 1H, J=7.0 Hz), 3.03 (t, 1H, J=9.1 Hz), 3.08-3.20 (m, 2H), 3.26-3.32 (m, 2H), 3.40 (br d, 1H, J=10.0 Hz), 3.61 (ABq, 2H, J=9.6 Hz), 4.50 (br s, 1H); $^{13}$C NMR (75 MHz, CD₃OD): δ 23.15, 23.79, 28.63, 28.48, 42.97, 45.71, 71.80, 72.95, 79.20, 80.20, 80.64, 80.80, 82.46, 157.92, 158.72, 174.04; MS (ES, [M+Na]⁺): m/z 459.23.

9: $^1$H NMR (300 MHz, CD₃OD) δ 1.38 (s, 9H), 1.42 (s, 9H), 1.69 (s, 9H), 2.88-3.09 (m, 2H), 3.18 (dd, 2H, J=7.6, 14.2 Hz), 3.25-3.33 (m, 2H), 3.33-3.35 (m, 4H), 3.36-3.48 (m, 3H), 4.29-4.40 (m, 2H), 4.44 (br s, 1H), 4.84 (m, 1H), 7.08 (br d, 1H, J=7.0 Hz), 7.20-7.37 (m, 5H), 7.52 (s, 1H), 7.66 (br d, 1H, J=7.6 Hz), 8.13 (br d, 1H, J=8.1 Hz); $^{13}$C NMR (75 MHz, CD₃OD): δ 28.48, 28.63, 28.82, 44.11, 54.77, 72.0, 72.52, 79.0, 81.01, 84.91, 116.22, 117.16, 120.18, 123.75, 125.56, 128.18, 128.32, 129.53, 139.34, 151.02, 172.2, 173.3; MS (ES, [M+Na]⁺): m/z 834.17.

10: $^1$H NMR (300 MHz, D₂O) δ 2.52-2.74 (m, 2H), 2.88-3.04 (m, 2H), 3.28-3.40 (m, 2H), 3.42-3.56 (m, 2H), 3.70-3.77 (m, 1H), 4.32-4.41 (m, 1H), 4.45-4.54 (m, 2H), 5.00-5.11 (m, 1H), 7.16-7.49 (m, 8H), 7.60-7.68 (m, 1H), 7.78 (dd, 1H, J=7.8, 17.8 Hz); $^{13}$C NMR (75 MHz, D₂O): δ 27.94, 38.35, 40.89, 43.41, 53.39, 54.78, 69.45, 70.79, 76.05, 76.58, 77.39, 109.04, 112.57, 118.97, 119.66, 122.34, 125.09, 126.79, 127.45, 127.82, 129.08, 136.80, 137.81, 173.28; MS (ES, [M+Na]⁺); Anal. Calcd for $C_{44}H_{47}NNaO_7$: 724.33. MS (ES, [M+H]⁺): m/z 511.99.

11: $^1$H NMR (300 MHz, CD₃OD) δ 1.38 (br s, 18H), 1.63 (s, 9H), 3.00-3.15 (m, 2H), 3.18 (d, 2H, J=7.0 Hz), 3.24 (br s, 1H), 3.32 (m, 2H), 4.47 (br s, 1H), 4.89 (m, 1H), 5.03 (s, 2H), 7.06-7.12 (m, 2H), 7.15-7.31 (m, 5H), 7.40 (br s, 1H), 7.50 (m, 1H), 8.05 (d, 1H, J=8.2 Hz); $^{13}$C NMR (75 MHz, CD₃OD): δ 26.91, 27.37, 27.65, 40.85, 54.57, 66.74, 69.79, 70.09, 76.83, 77.27, 78.84, 79.03, 79.70, 83.40, 114.71, 114.83, 118.24, 122.16, 123.38, 124.04, 127.78, 127.93, 134.48, 134.87, 149.26, 155.37, 157.08, 171.30; MS (ES, [M+Na]⁺): m/z 835.33.

12: $^1$H NMR (300 MHz, D₂O) δ 2.32-2.42 (m, 2H), 2.70-2.78 (t, 1H, J=9.6 Hz), 3.18 (br d, 1H, J=14.0 Hz), 3.22-3.42 (m, 3H), 3.48-3.60 (m, 2H), 4.30 (br s, 1H), 5.14 (dd, 1H, J=5.7, 10.3 Hz), 5.24 (br s, 2H), 7.17 (t, 1H, J=7.6 Hz), 7.22 (br s, 1H), 7.28 (t, 1H, J=7.6 Hz), 7.36 (dd, 2H, J=3.8, 7.6 Hz), 7.42-7.49 (m, 3H), 7.53 (d, 1H J=8.2 Hz), 7.70 (d, 1H, J=8.2 Hz); $^{13}$C NMR (75 MHz, D₂O): δ 27.22, 40.86, 53.57, 68.43, 69.29, 70.73, 75.97, 76.51, 77.46, 109.13, 112.57, 118.93, 119.69, 122.37, 124.98, 126.72, 128.74, 129.18, 129.21, 135.40, 136.82, 173.32; MS (ES, [M+Na]⁺); Anal. Calcd for $C_{44}H_{47}NNaO_7$: 724.33. MS (ES, [M+H]⁺): m/z 513.23.

Example 38

Bioactivity of Peptides Containing a Sugar-lysine Chimera of the Present Invention Two peptides containing sugar-lysine chimeras (A and B shown below; see Example 1 and 37) were examined in a bioactivity assay to analyze their antimicrobial properties.

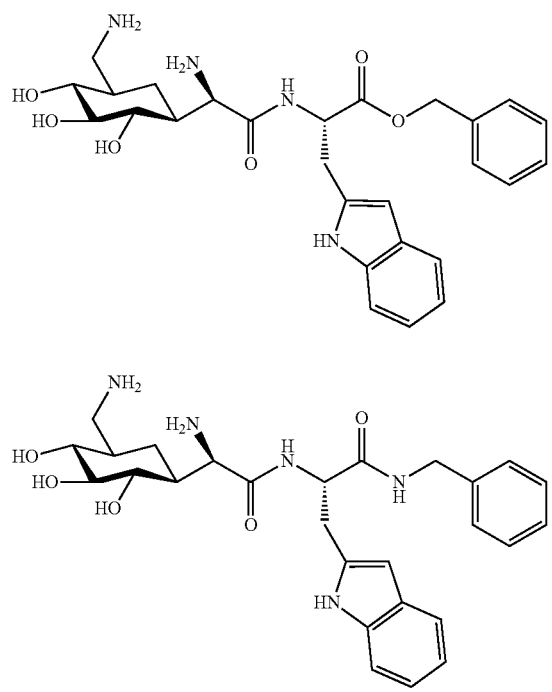

Materials and Methods:
Bacterial Isolates:

Study isolates were obtained as part of the Canadian National Intensive Care Unit (CAN-ICU) Study. The CAN-ICU study included 19 medical centres from all regions of Canada with active ICUs. From September 2005-June 2006, inclusive, each centre collected a maximum of 300 consecutive pathogens isolated from blood, urine, tissue/wound, and respiratory specimens (one pathogen per cultured site per patient) of ICU patients. Participating study sites were requested to only obtain "clinically significant" specimens from patients with a presumed infectious disease. Surveillance swabs, eye, ear, nose and throat swabs were excluded. Anaerobic organisms and fungal organisms were also excluded. Isolates were shipped to the reference laboratory (Health Sciences Centre, Winnipeg, Canada) on Amies charcoal swabs, subcultured onto appropriate media, and stocked in skim milk at −80° C. until minimum inhibitory concentration (MIC) testing was carried out.

Antimicrobial Susceptibilities:

After obtaining two subcultures from frozen stock, the in vitro activities of neomycin as well as compounds A and B were determined by microbroth dilution in accordance with the Clinical Laboratory Standards Institute (CLSI) guidelines (M7-A7, 2006 and M100-S16, 2006). Antimicrobial agents were obtained as laboratory grade powders from their respective manufacturers or from the lab of the inventors. Stock solutions were prepared and dilutions made as described by CLSI (M7-A7, 2006). The MICs of the antimicrobial agents for the isolates were determined using 96-well custom designed microtitre plates. These plates contained doubling antimicrobial dilutions in 100 μl/well of cation adjusted Mueller-Hinton broth and inoculated to achieve a final concentration of approximately $5 \times 10^5$ CFU/ml then incubated in ambient air for 24 hours prior to reading. Colony counts were performed periodically to confirm inocula. Quality control was performed using ATCC QC organisms.

For all antimicrobials tested, MIC interpretive standards were defined according to CLSI breakpoints (M 100-S 16, 2006).

Results:

Both compounds showed the best antimicrobial activity against *S. epidermidis*, as shown in Table 3.

TABLE 3

Antimicrobial activities of compounds A and B.

| Control Organism | A MIC values in microgram/mL | B MIC values in microgram/mL |
| --- | --- | --- |
| *S. aureus* ATCC 29213 | 256 | 256 |
| MRSA ATCC 33592 | 256 | >512 |
| *S. epidermidis* ATC 14990 | 128 | 128 |
| MRSE (CZ >32) CAN-ICU 61589 | 256 | 128 |
| *S. pneumoniae* ATCC 49619 | >512 | >512 |
| *E. coli* ATCC 25922 | 512 | 512 |
| *E. coli* ATCC (Gent-R) CAN-ICU 61714 | 512 | 512 |
| *E. coli* ATCC (Amikacin 32) CAN-ICU 63074 | 256 | not tested |
| *P. aeruginosa* ATCC 27853 | >512 | >512 |

All of the methods and apparatuses disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Baldwin et al., *Tetrahedron Lett.*, 34:5645, 1993.
Beausoleil and Lubell, *J. Am. Chem. Soc.*, 118:12902, 1996.
Blankley et al., *J. Med. Chem.*, 30:992, 1987.
Bretscher et al., *J. Am. Chem. Soc.*, 123:777-778, 2001.
Buku et al., *Proc. Natl. Acad. Sci. USA.*, 77:2370-2371, 1980.
Bulet et al., *Eur. J. Biochem.*, 238:64, 1996.
Bulet et al., *J. Biol. Chem.*, 268:14893, 1993.
Bundgaard, In: *Design of Prodrugs*, Chapter 1:7-9; 21-24, Elsevier Science Publishers, Amsterdam, 1985.
Bundgaard, In: *Novel Chemical Approaches in Prodrug Design*, Drugs of the Future, 16:443-458, 1991.

Cavelier et al., *J. Am. Chem. Soc.*, 124:2917-2923, 2002.
Chakraborty et al., *J. Am. Chem. Soc.*, 120:12962, 1998.
Che and Marshall, *J. Org. Chem.*, 69:9030-9042, 2004.
Cipolla et al., *J. Org. Chem.*, 62:6678-6681, 1997.
Cluzeau and Lubell, *Biopolymers, Peptide Science*, 80:98, 2005.
Davies et al., *Synlett*, 5:901-903, 2004.
Delaney and Madison, *J. Am. Chem. Soc.*, 104:6635, 1982.
Dumy et al., *J. Am. Chem. Soc.*, 119:918, 1997.
Evans et al., *J. Amer. Chem. Soc.*, 112:4011-4030, 1990.
Fischer and Schmid, *Biochemistry*, 29:2205-2212, 1990.
Greene and Wuts, In: *Protective Groups in Organic Synthesis*, 3$^{rd}$ Ed., Wiley-Interscience, New York, 1999.
Grotenbreg et al., *J. Am. Chem. Soc.*, 126:3444, 2004.
Gueyrard et al., *Synlett.*, 520-522, 2005.
Hancock and Lehrer, *Trends Biotech.*, 16:82, 1998.
Hancock and Scott, *Proc. Natl. Acad. Sci. USA*, 97:8856, 2000.
*Handbook of Pharmaceutical Salts: Properties, Selection and Use* (Stahl & Wermuth, Eds., Verlag Helvetica Chimica Acta, 2002.
Jeannotte and Lubell, *J. Org. Chem.*, 69:4656-4662, 2004.
Jenkins et al., *J. Org. Chem.*, 69:8565-85732004
Kakinoki et al., *Polymer Bulletin*, 53:109-115, 2005.
Knorr et al., *Tetrahedron Lett.*, 30:1927, 1989.
Latham, *Nat. Biotechnol.*, 17:755, 1999.
Li and Moeller, *J. Am. Chem. Soc.*, 118:10106, 1996.
Nakajima and Volcani, *Science*, 164:1400-1401, 1969.
Owens et al., *J. Org. Chem.*, 72:4635-4643, 2007.
PCT Appl. entitled, "Synthesis of Carbohydrate-templated amino acids and methods of using same," by Frank Schweizer, Kaidong Zhang, Neil Owens and George Zhanel, filed Sep. 18, 2007.
Petter, *Tetrahedron Lett.*, 30:399-402, 1989.
Postels and Koenig, *Tetrahedron Lett.*, 35:535, 1994.
Pu et al., *J. Org. Chem.*, 56:1280-1283, 1991.
Quancard et al., *J. Org. Chem.*, 69:7940, 2004.
Reddy et al., *Int. J. Antimicrobial Agents*, 24:536-547, 2004.
Reddy et al., *Tetrahedron*, 54:10649, 1998.
Remington's Pharmaceutical Sciences, 18th Ed., Mack Printing Company, 1990.
Samanen et al., *Int. J. Pept. Protein. Res.*, 35:501, 1990.
Sambrook et al., In: *Molecular cloning: a laboratory manual*, 2$^{nd}$ Ed., Cold Spring Harbor Laboratory Press, Cold Spring Harbor, N.Y., 1989.
Schweizer and Inazu, *Org. Lett.*, 3:4115, 2001.
Sharma and Lubell, *J. Org. Chem.*, 61:202-209, 1996.
Stonehouse et al., *J. Am. Chem. Soc.*, 116:6037-6038, 1994.
Strom et al., *J. Med. Chem.*, 46:1567, 2003.
Tam and Miao, *J. Am. Chem. Soc.*, 121:9013-9022, 1999.
Taylor et al., *J. Am. Chem. Soc.*, 116:10803-10804, 1994.
Taylor et al., *J. Biol. Chem.*, 275:38417, 2000.
Taylor et al., *Org. Lett.*, 5:4413-4416, 2003.
Trabocchi et al., *Eur. J. Org. Chem.*, 22:4621-4627, 2004.
Vitagliano et al., *Biopolymers*, 58:459, 2001.
Williams, Synthesis of Optically Active α-Amino Acids, Pergamon Press, 1989.
Williams et al., *J. Amer. Chem. Soc.*, 113:9276-9286, 1991.
Wilmot and Thornton, *J. Mol. Biol.*, 203:221-232, 1988.
Wong et al., *J. Am. Chem. Soc.*, 120:8319, 1998.
Zhang and Schweizer, *Synlett*, no. 20:3111-3115, 2005.
Zhang et al., *Synlett*, no. 2:239-242, 2007.

What is claimed is:

1. A fused bicyclic sugar-proline of formula:

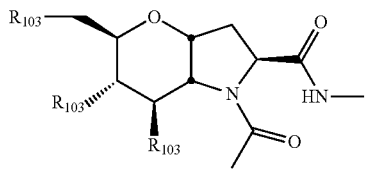

wherein each $R_{103}$ is independently —$OR_{106}$, wherein $R_{106}$ is —H or a hydroxyl protecting group.

2. A method of synthesizing the fused bicyclic sugar-proline of claim 1, comprising:
    a) protecting the $C_2$-amino-substituted function of a fully hydroxy protected, $C_1$-vinyl substituted sugar;
    b) installing a pyrrolidine ring under amino-iodocyclization conditions to form a fused bicyclic sugar-pyrrolidine;
    c) converting the fused bicyclic sugar-pyrrolidine into a fused tricyclic carbamate;
    d) hydrolyzing the carbamate to provide an amino alcohol;
    e) protecting the amino group of the amino alcohol to provide an amino-protected fused bicyclic sugar-proline;
    f) oxidizing the alcohol of the amino alcohol to form a carboxylic acid;
    g) coupling the carboxylic acid with methylamine to form an amide;
    h) deblocking the protected amine; and
    i) coupling the amine with an amine-protected amino acid;
    j) optionally deblocking of the amine-protected amino acid; and
    k) optionally deblocking one or more of the hydroxy groups of the sugar.

3. The method of claim 2, wherein a compound of formula (VII) is formed as an intermediate:

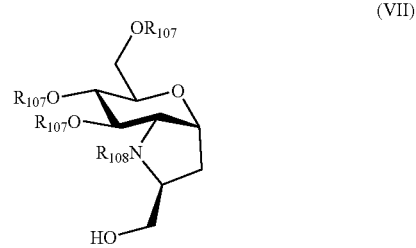

(VII)

wherein:
    $R_{107}$ is a hydroxy protecting group; and
    $R_{108}$ is -H or an amine protecting group.

4. A method of peptide or petidomimetic synthesis comprising incorporating the fused bicyclic sugar-proline of claim 1 into the peptide or peptidomimetic.

5. The method of claim 4, wherein the peptide is an antimicrobial peptide, and wherein the incorporation of the fused bicyclic sugar-proline comprises replacing one or more of the amino acids in the wild-type amino acid sequence of the antimicrobial peptide with the fused bicyclic sugar-proline.

* * * * *